US009475815B2

(12) United States Patent
Lobell et al.

(10) Patent No.: US 9,475,815 B2
(45) **Date of Patent: *Oct. 25, 2016**

(54) SUBSTITUTED BENZOTHIENYL-PYRROLOTRIAZINES AND USES THEREOF

(71) Applicant: Bayer Intellectual Property GmbH, Monheim (DE)

(72) Inventors: Mario Lobell, Wuppertal (DE); Walter Hübsch, Wuppertal (DE); Hartmut Schirok, Langenfeld (DE); Mélanie Héroult, Düsseldorf (DE); Dirk Brohm, Mettmann (DE); Marie-Pierre Collin, Wuppertal (DE); Sylvia Grünewald, Berlin (DE); Klemens Lustig, Wuppertal (DE); Ulf Bömer, Glienicke (DE); Verena Voehringer, Wolfegg (DE); Niels Lindner, Wuppertal (DE)

(73) Assignee: BAYER INTELLETUAL PROPERTY GMBH, Monheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/380,755

(22) PCT Filed: Feb. 20, 2013

(86) PCT No.: PCT/EP2013/053378

§ 371 (c)(1),
(2) Date: Aug. 25, 2014

(87) PCT Pub. No.: WO2013/124316

PCT Pub. Date: Aug. 29, 2013

(65) Prior Publication Data

US 2015/0031676 A1 Jan. 29, 2015

(30) Foreign Application Priority Data

Feb. 23, 2012 (EP) .................................... 12156759

(51) Int. Cl.

| | |
|---|---|
| ***C07D 487/04*** | (2006.01) |
| ***C07D 409/04*** | (2006.01) |
| ***C07D 409/14*** | (2006.01) |
| ***A61K 31/53*** | (2006.01) |
| ***A61K 31/4985*** | (2006.01) |
| ***A61K 31/4427*** | (2006.01) |
| ***A61P 35/00*** | (2006.01) |
| ***A61K 31/5377*** | (2006.01) |
| ***A61K 31/5513*** | (2006.01) |
| ***C07D 519/00*** | (2006.01) |

(52) U.S. Cl.

CPC ............. *C07D 487/04* (2013.01); *A61K 31/53* (2013.01); *A61K 31/5377* (2013.01); *A61K 31/5513* (2013.01); *C07D 409/04* (2013.01); *C07D 409/14* (2013.01); *C07D 519/00* (2013.01)

(58) Field of Classification Search

CPC C07D 487/04; C07D 409/04; C07D 409/14; A61K 31/53; A61K 31/382

USPC .......................................... 544/183; 514/243

See application file for complete search history.

(56) References Cited

FOREIGN PATENT DOCUMENTS

| | | | |
|---|---|---|---|
| WO | 0071129 | A1 | 11/2000 |
| WO | 0119828 | A2 | 3/2001 |
| WO | 2005037836 | A2 | 4/2005 |
| WO | 2005097800 | A1 | 10/2005 |
| WO | 2005121147 | A1 | 12/2005 |
| WO | 2007056170 | A2 | 5/2007 |
| WO | 2007061737 | A2 | 5/2007 |
| WO | 2007061882 | A2 | 5/2007 |
| WO | 2007064883 | A2 | 6/2007 |
| WO | 2007064931 | A2 | 6/2007 |
| WO | 2007064932 | A2 | 6/2007 |
| WO | 2007079164 | A2 | 7/2007 |
| WO | 2009042543 | A1 | 4/2009 |
| WO | 2009136966 | A1 | 11/2009 |
| WO | 2010051043 | A1 | 5/2010 |
| WO | 2010126960 | A1 | 11/2010 |

OTHER PUBLICATIONS

Hynes et al., Cancer Res. Jul. 1, 2010 ;70(13):5199-202.*
Greulich et al.,Trends Mol Med. May 2011;17(5):283-92.*
Cecil Textbook of Medicine, edited by Bennet, J.C., and Plum F., 20th edition,vol. 1, 1004-101 O, 1996.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Barder et al., "Catalysts for Suzuki-Miyaura Coupling Processes: Scope and Studies of the Effect of Ligand Structure," 2005, Journal of Am. Chem. Soc., 127:4685-4696.
Berge et al., "Pharmaceutical Salts," Journal of Pharm. Sciences, Jan. 1977, 66(1):1-19.

(Continued)

*Primary Examiner* — Venkataraman Balasubramanian

(57) ABSTRACT

This invention relates to novel substituted 5-(1-benzothiophen-2-yl)pyrrolo[2,1-f][1,2,4]triazin-4-amine derivatives having protein tyrosine kinase inhibitory activities, to processes for the preparation of such compounds, to pharmaceutical compositions containing such compounds, and to the use of such compounds or compositions for treating proliferative disorders, in particular cancer and tumor diseases.

6 Claims, No Drawings

(56) References Cited

OTHER PUBLICATIONS

Bergers et al., "Modes of resistance to antiangiogenic therapy," Nature Reviews Cancer, Aug. 2008, 8:592-603.
Greene et al., Protective Groups in Organic Synthesis, Third Edition, "The Role of Protective Groups in Organic Synthesis," 1999, John Wiley & Sons, Inc., ISBN 0-471-22057-4 (Electronic) 1-16.
Greulich et al., "Targeting mutant fibroblast growth factor receptors in cancer," Trends in Molecular Medicine, May 2011, 17(5):283-292.
Haugsten et al., "Roles of Fibroblast Growth Factor Receptors in Carcinogenesis," American Association for Cancer Research, Molecular Cancer Research, 2010, 1439-1452.
Heinzle et al., "Targeting fibroblast-growth-factor-receptor-dependent signaling for cancer therapy," Expert Opin. Ther. Targets, 2011, 15(7):830-846.
Itoh et al., "Fibroblast growth factors: from molecular evolution to roles in development, metabolism and disease," JB Journal of Biochemistry, 2011, 149(2):121-130.
Jilek et al., "Potential Metabolites of the Neuroleptic Agent Octoclothepin; Synthesis and Pharmacology of 8-Chloro-6-Hydroxy-10-(4-Methylpiperazino)-10,11-Dihydrodibenzo[b,f]Thiepin and Some Related Compounds," Research Institute for Pharmacy and Biochemistry, 130 00 Prague 3, Collection Czechoslov Chem. Commun., 1978, 43:1747-1759.
Knapp et al., "A General Solution for Unstable Boronic Acids: Slow-Release Cross-Coupling from Air-Stable MIDA Boronates," Journal Am. Chem. Society, 2009, 131:6961-6963.
Kinzel et al., "A New Palladium Precatalyst Allows for the Fast Suzuki-Miyaura Coupling Reactions of Unstable Polyfluorophenyl and 2-Heteroaryl Boronic Acids," Journal Am. Chem. Society, 132:14073-14075.
Korc et al, "The Role of Fibroblast Growth Factors in Tumor Growth," Current Cancer Drug Targets, 2009, 9:639-651.
Kotha et al., "Recent applications of the Suzuki-Miyaura cross-coupling reaction in organic synthesis," Tetrahedron, 2002, 58:9633-9695.
Balkrishna et al, "Oxidation of α, β-Unstaturated Aldehydes," Tetrahedron, 1981, 37:2091-1096.
Plé et al., "Synthesis of Substituted Benzo[b]thiophenes by Acid-Catalyzed Cyclization of Thiophenylacetals and Ketones," J. Heterocyclic Chem., 1988, 25:1271-1272.
"Polanska et al., ""Extracellular Interactome of the FGF Receptor—Ligand System: Complexities and theRelative Simplicity of the Worm,""Development Dynamics, 2009, 238:277-293".
Raach et al., "Sodium Chlorite-Hydrogen Peroxide—A Mild and Selective Reagent for the Oxidation of Aldehydes to Carboxylic Acids," Journal Prakt Chem., 2000, 342(6):605-608.
Swinney et al., "How were new medicines discovered?," Nature Reviews Drug Discovery, Jul. 2011, 10:507-519.
Nooy et al., "On the Use of Stable Organic Nitroxyl Radicals for the Oxidation of Primary and Secondary Alcohols," Synthesis, Oct. 1996, 1153-1174.
Venturelli et al., "Optimizing Cell Permeation of an Antibiotic Resistance Inhibitor for Improved Efficacy," Journal Med. Chem., 2007, 50:5644-5654.
Wesche et al., "Fibroblast growth factors and their receptors in cancer," Biochemical Journal, 2011, 437:199-213. Supplemental Tables S1-S3 and additional references (pp. 1-13 at the end).
Zhao et al., "Oxidation of Primary Alcohols to Carboxylic Acids with Sodium Chlorite Catalyzed by Tempo and Bleach: 4-Methoxyphenylacetic Acid (Benzeneacetic acid, 4-methoxy-," Organic Syntheses, 2005 81:195-204.
Worldwide Health Organization, Fact Sheet No. 297, Feb. 2011 updated Feb. 2014.
S. L. Buchwald et al., J. Am. Chem. Soc. 132 (40), 14073-14075 (2010).
H. W. Pinnick et al. , Tetrahedron 37, 2091-2096 (1981).
Yoshida et al., Chem. Pharm. Bull. 1996, 44 (7), 1376-1386.
International Search Report, PCT/EP2013/053378, dated Mar. 13, 2013.

* cited by examiner

SUBSTITUTED BENZOTHIENYL-PYRROLOTRIAZINES AND USES THEREOF

This invention relates to novel substituted 5-(1-benzothiophen-2-yl)pyrrolo[2,1-f][1,2,4]triazin-4-amine derivatives having protein tyrosine kinase inhibitory activities, to processes for the preparation of such compounds, to pharmaceutical compositions containing such compounds, and to the use of such compounds or compositions for treating proliferative disorders, in particular cancer and tumor diseases.

Cancer is a leading cause of death worldwide and accounted for 7.6 million deaths (around 13% of all deaths) in 2008. Deaths from cancer are projected to continue to rise worldwide to over 11 million in 2030 (WHO source, Fact Sheet No. 297, February 2011).

There are many ways how cancers can arise which is one of the reasons why their therapy is difficult. One way that transformation of cells can occur is following a genetic alteration. The completion of the human genome project showed genomic instability and heterogeneity of human cancer genes. Recent strategies to identify these genetic alterations sped up the process of cancer-gene discovery. Gene abnormality can, for instance, lead to the overexpression of proteins, and hence to a non-physiological activation of these proteins. One family of proteins from which a number of oncoproteins derive are tyrosine kinases and in particular receptor tyrosine kinases (RTKs). In the past two decades, numerous avenues of research have demonstrated the importance of RTK-mediated signalling in adverse cell growth leading to cancer. In recent years, promising results have been achieved in the clinic with selective small-molecule inhibitors of tyrosine kinases as a new class of anti-tumorigenic agents [Swinney and Anthony, *Nature Rev. Drug Disc.* 10 (7), 507-519 (2011)].

Fibroblast growth factors (FGFs) and their receptors (FGFRs) form part of a unique and diverse signalling system which plays a key role in a variety of biological processes which encompass various aspects of embryonic development and adult pathophysiology [Itoh and Ornitz, *J. Biochem.* 149 (2), 121-130 (2011)]. In a spatio-temporal manner, FGFs stimulate through FGFR binding a wide range of cellular functions including migration, proliferation, differentiation, and survival.

The FGF family comprises 18 secreted polypeptidic growth factors that bind to four highly conserved receptor tyrosine kinases (FGFR-1 to −4) expressed at the cell surface. In addition, FGFR-5 can bind to FGFs but does not have a kinase domain, and therefore is devoid of intracellular signalling. The specificity of the ligand/receptor interaction is enhanced by a number of transcriptional and translational processes which give rise to multiple isoforms by alternative transcriptional initiation, alternative splicing, and C-terminal truncations. Various heparan sulfate proteoglycans (e.g. syndecans) can be part of the FGF/FGFR complex and strongly influence the ability of FGFs to induce signalling responses [Polanska et al., *Developmental Dynamics* 238 (2), 277-293 (2009)]. FGFRs are cell surface receptors consisting of three extracellular immunoglobulin-like domains, a single-pass transmembrane domain, and an intracellular dimerized tyrosine kinase domain. Binding of FGF bring the intracellular kinases into close proximity, enabling them to transphosphorylate each other. Seven phosphorylation sites have been identified (e.g., in FGFR-1 Tyr463, Tyr583, Tyr585, Tyr653, Tyr654, Tyr730, and Tyr766).

Some of these phosphotyrosine groups act as docking sites for downstream signalling molecules which themselves may also be directly phosphorylated by FGFR, leading to the activation of multiple signal transduction pathways. Thus, the MAPK signalling cascade is implicated in cell growth and differentiation, the PI3K/Akt signalling cascade is involved in cell survival and cell fate determination, while the PI3K and PKC signalling cascades have a function in the control of cell polarity. Several feedback inhibitors of FGF signalling have now been identified and include members of the Spry (Sprouty) and Sef (similar expression to FGF) families. Additionally, in certain conditions, FGFR is released from pre-Golgi membranes into the cytosol. The receptor and its ligand, FGF-2, are co-transported into the nucleus by a mechanism that involves importin, and are engaged in the CREB-binding protein (CBP) complex, a common and essential transcriptional co-activator that acts as a gene activation gating factor. Multiple correlations between the immunohistochemical expression of FGF-2, FGFR-1 and FGFR-2 and their cytoplasmic and nuclear tumor cell localizations have been observed. For instance, in lung adenocarcinomas this association is also found at the nuclear level, emphasizing an active role of the complex at the nucleus [Korc and Friesel, *Curr. Cancer Drugs Targets* 5, 639-651 (2009)].

FGFs are widely expressed in both developing and adult tissues and play important roles in a variety of normal and pathological processes, including tissue development, tissue regeneration, angiogenesis, neoplastic transformation, cell migration, cellular differentiation, and cell survival. Additionally, FGFs as pro-angiogenic factors have also been implicated in the emerging phenomenon of resistance to vascular endothelial growth factor receptor-2 (VEGFR-2) inhibition [Bergers and Hanahan, *Nat. Rev. Cancer* 8, 592-603 (2008)].

Recent oncogenomic profiles of signalling networks demonstrated an important role for aberrant FGF signalling in the emergence of some common human cancers [Wesche et al., *Biochem. J.* 437 (2), 199-213 (2011)]. Ligand-independent FGFR constitutive signalling has been described in many human cancers, such as brain cancer, head and neck cancer, gastric cancer and ovarian cancer. FGFR-mutated forms as well as FGFR-intragenic translocations have been identified in malignancies such as myeloproliferative diseases. Interestingly, the same mutations discovered to be the cause of many developmental disorders are also found in tumor cells (e.g., the mutations found in achondroplasia and thanatophoric dysplasia, which cause dimerization and thus constitutive activation of FGFR-3, are also frequently found in bladder cancer). A mutation that promotes dimerization is just one mechanism that can increase ligand-independent signalling from FGFRs. Other mutations located inside or outside of the kinase domain of FGFRs can change the conformation of the domain giving rise to permanently active kinases.

Amplification of the chromosomal region 8p11-12, the genomic location of FGFR-1, is a common focal amplification in breast cancer and occurs in approximately 10% of breast cancers, predominantly in oestrogen receptor-positive cancers. FGFR-1 amplifications have also been reported in non-small cell lung squamous carcinoma and are found at a low incidence in ovarian cancer, bladder cancer and rhabdomyosarcoma. Similarly, approximately 10% of gastric cancers show FGFR-2 amplification, which is associated with poor prognosis, diffuse-type cancers. Moreover, multiple single nucleotide polymorphisms (SNPs) located in FGFR-1 to −4 were found to correlate with an increased risk of developing selective cancers, or were reported to be associated with poor prognosis (e.g., FGFR-4 G388R allele in breast cancer, colon cancer and lung adenocarcinoma). The direct role of these SNPs to promote cancer is still controversial.

In summary, a great number of in vitro and in vivo studies have been performed that validate FGFR-1 to -4 as important cancer targets, and comprehensive reviews have summarized these findings [see, for example, Heinzle et al., *Expert Opin. Ther. Targets* 15 (7), 829-846 (2011); Wesche et al., *Biochem. J.* 437 (2), 199-213 (2011); Greulich and Pollock, *Trends in Molecular Medicine* 17 (5), 283-292 (2011); Haugsten et al., *Mol. Cancer Res.* 8 (11), 1439-1452 (2010)]. Several strategies have been followed to attenuate aberrant FGFR-1 to −4 signalling in human tumors including blocking antibodies and small-molecule inhibitors, amongst others. A number of selective small-molecule FGFR inhibitors are currently in clinical development, such as AZD-4547 (AstraZeneca) and BJG-398 (Novartis).

Notwithstanding the significant advancements that have generally been achieved in cancer therapy in recent years, there is a continuing need to identify new anti-cancer compounds with improved properties, such as higher potency, greater selectivity, reduced toxicity and/or better tolerability. Therefore, the technical problem to be solved according to the present invention may be seen in providing alternative compounds having inhibitory activity on the FGFR kinases, thus offering new therapeutic options for the treatment of FGFR-mediated diseases, in particular cancer and other proliferative disorders.

Fused hetero-5,6-bicyclic kinase inhibitors bearing a 9- or a 10-membered bicyclic heteroaryl substituent have been disclosed in WO 2007/061737-A2 and WO 2005/097800-A1, respectively. These compounds were stated to be useful for the treatment of cancer and other diseases owing to their inhibitory action on the mTOR (mammalian target of Rapamycin) and/or IGF-1R (type 1 insulin-like growth factor receptor) kinases. Further hetero-5,6-bicyclic template structures associated with the inhibition of kinases have been described in, inter alia, WO 01/19828-A2, WO 2007/079164-A2 and WO 2010/051043-A1.

4-Aminopyrrolo[2,1-f][1,2,4]triazine derivatives with differing inhibition profiles against a number of protein kinases have been disclosed in, inter alia, WO 00/71129-A1, WO 2007/056170-A2, WO 2007/061882-A2, WO 2007/064932-A2, WO 2009/136966-A1, and WO 2010/126960-A1.

In WO 2005/121147-A1, WO 2007/064883-A2 and WO 2007/064931-A2,4-aminopyrrolo[2,1-f]-[1,2,4]triazine derivatives containing a substituted diarylurea group in 5-position were described as having FGFR-1 inhibiting activity. However, other receptor tyrosine kinases, notably the VEGFR, PDGFR and Tie-2 kinases, are also significantly inhibited by this particular class of compounds. As it was hypothesized that such multi-kinase activity might lead to an augmentation of potential side effects during treatment, it was the aim of the present invention to identify new agents having an improved selectivity for the FGFR kinases, thus providing new options for a more tolerable cancer therapy.

Surprisingly, it has now been found that 4-aminopyrrolo[2,1-f][1,2,4]triazine derivatives bearing a specifically substituted benzothiophen-2-yl residue in 5-position exhibit potent and selective inhibition of FGFR kinases, notably of the FGFR-1 and FGFR-3 kinases, which renders these compounds particularly useful for the treatment of proliferative disorders, such as cancer and tumor diseases.

Thus, in one aspect, the present invention relates to 7-substituted 5-(1-benzothiophen-2-yl)pyrrolo-[2,1-f][1,2,4]triazin-4-amine derivatives of the general formula (I)

(I)

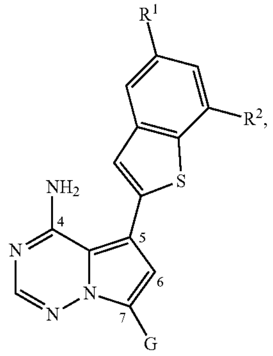

wherein $R^1$ is hydrogen, chloro, methyl or methoxy, $R^2$ is hydrogen or methoxy, with the proviso that at least one of $R^1$ and $R^2$ is other than hydrogen, and G represents the group —$CH_2$—$OR^3$, —$CH_2$—$NR^4R^5$ or —C(═O)—$NR^6R^7$, wherein $R^3$ is ($C_1$-$C_6$)-alkyl substituted with a residue selected from the group consisting of amino, mono-($C_1$-$C_4$)-alkylamino, di-($C_1$-$C_4$)-alkylamino, aminocarbonyl, mono-($C_1$-$C_4$)-alkylaminocarbonyl, di-($C_1$-$C_4$)-alkylaminocarbonyl and 4- to 6-membered heterocycloalkyl, or is 4- to 6-membered heterocycloalkyl, wherein said 4- to 6-membered heterocycloalkyl groups are optionally substituted with one or two residues independently selected from the group consisting of ($C_1$-$C_4$)-alkyl, oxo, hydroxy, amino and aminocarbonyl, $R^4$ is hydrogen or ($C_1$-$C_4$)-alkyl, $R^5$ is ($C_1$-$C_6$)-alkyl substituted with one or two residues independently selected from the group consisting of hydroxy, ($C_1$-$C_4$)-alkoxy, amino, mono-($C_1$-$C_4$)-alkylamino, di-($C_1$-$C_4$)-alkylamino, hydroxycarbonyl, aminocarbonyl, mono-($C_1$-$C_4$)-alkylaminocarbonyl, di-($C_1$-$C_4$)-alkylaminocarbonyl, ($C_1$-$C_4$)-alkylcarbonylamino, aminocarbonylamino and 4- to 6-membered heterocycloalkyl, wherein said 4- to 6-membered heterocycloalkyl is optionally substituted with one or two residues independently selected from the group consisting of ($C_1$-$C_4$)-alkyl, oxo, hydroxy, amino and aminocarbonyl, or is ($C_1$-$C_4$)-alkylcarbonyl optionally substituted with a residue selected from the group consisting of hydroxy, ($C_1$-$C_4$)-alkoxy, amino, mono-($C_1$-$C_4$)-alkylamino and di-($C_1$-$C_4$)-alkylamino, or is ($C_3$-$C_6$)-cycloalkyl optionally substituted with one or two residues independently selected from the group consisting of ($C_1$-$C_4$)-alkyl, hydroxy, ($C_1$-$C_4$)-alkoxy, amino, mono-($C_1$-$C_4$)-alkylamino and di-($C_1$-$C_4$)-alkylamino, or is 4- to 6-membered heterocycloalkyl optionally substituted with one or two residues independently selected from the group consisting of $(C_1-C_4)$-alkyl, oxo, hydroxy, amino and aminocarbonyl, or $R^4$ and $R^5$ are joined and, taken together with the nitrogen atom to which they are attached, form a mono- or bicyclic, saturated, 4- to 10-membered heterocycloalkyl ring which may contain a second ring heteroatom selected from N and O, and which may be substituted with up to three residues independently selected from the group consisting of $(C_1-C_4)$-alkyl, oxo, hydroxy, $(C_1-C_4)$-alkoxy, amino, mono-$(C_1-C_4)$alkylamino, di-$(C_1-C_4)$-alkylamino, azetidino, pyrrolidino, piperidino, $(C_1-C_4)$alkylcarbonyl, $(C_3-C_6)$-cycloalkylcarbonyl, hydroxycarbonyl, aminocarbonyl, mono-$(C_1-C_4)$-alkylaminocarbonyl, di-$(C_1-C_4)$-alkylaminocarbonyl, thienyl and phenyl, wherein the alkyl groups of said $(C_1-C_4)$-alkyl, $(C_1-C_4)$-alkoxy, mono-$(C_1-C_4)$alkylamino, di-$(C_1-C_4)$-alkylamino and $(C_1-C_4)$-alkylcarbonyl residues, for their part, are optionally substituted with a residue selected from the group consisting of hydroxy, amino and aminocarbonyl, and wherein said thienyl and phenyl groups are optionally substituted with one or two residues independently selected from the group consisting of fluoro, chloro, cyano, methyl and trifluoromethyl, or $R^4$ and $R^5$ are joined and, taken together with the nitrogen atom to which they are attached, form an imidazol-1-yl or 1,2,4-triazol-1-yl ring each of which may be substituted with one or two residues independently selected from the group consisting of $(C_1-C_4)$-alkyl and cyano, $R^6$ is hydrogen, $R^7$ is 4- to 6-membered heterocycloalkyl optionally substituted with one or two residues independently selected from the group consisting of $(C_1-C_4)$-alkyl, oxo, hydroxy, amino and aminocarbonyl, or $R^6$ and $R^7$ are joined and, taken together with the nitrogen atom to which they are attached, form a monocyclic, saturated, 4- to 7-membered heterocycloalkyl ring which may contain a second ring heteroatom selected from N and O, and which may be substituted with one or two residues independently selected from the group consisting of $(C_1-C_4)$-alkyl, oxo, hydroxy, amino, mono-$(C_1-C_4)$-alkylamino, di-$(C_1-C_4)$-alkylamino and aminocarbonyl.

The compounds according to this invention can also be present in the form of their salts, solvates and/or solvates of the salts.

Compounds according to the invention are the compounds of the formula (I) and their salts, solvates and solvates of the salts, the compounds included in the formula (I) of the formulae (I-A) to (I-E) mentioned in the following and their salts, solvates and solvates of the salts, and the compounds included in the formula (I) and mentioned in the following as process products and/or embodiment examples and their salts, solvates and solvates of the salts, where the compounds included in the formula (I) and mentioned in the following are not already salts, solvates and solvates of the salts.

Salts for the purposes of the present invention are preferably pharmaceutically acceptable salts of the compounds according to the invention (for example, see S. M. Berge et al., "Pharmaceutical Salts", *J. Pharm. Sci.* 1977, 66, 1-19). Salts which are not themselves suitable for pharmaceutical uses but can be used, for example, for isolation or purification of the compounds according to the invention are also included.

Pharmaceutically acceptable salts include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, formic acid, acetic acid, trifluoroacetic acid, propionic acid, lactic acid, tartaric acid, malic acid, citric acid, fumaric acid, maleic acid, and benzoic acid.

Pharmaceutically acceptable salts also include salts of customary bases, such as for example and preferably alkali metal salts (for example sodium and potassium salts), alkaline earth metal salts (for example calcium and magnesium salts), and ammonium salts derived from ammonia or organic amines, such as illustratively and preferably ethylamine, diethylamine, triethylamine, N,N-diisopropylethylamine, monoethanolamine, diethanolamine, triethanolamine, dimethylaminoethanol, diethylaminoethanol, procaine, dicyclohexylamine, dibenzylamine, N-methylmorpholine, N-methylpiperidine, arginine, lysine, and 1,2-ethylenediamine.

Solvates in the context of the invention are designated as those forms of the compounds according to the invention which form a complex in the solid or liquid state by stoichiometric coordination with solvent molecules. Hydrates are a specific form of solvates, in which the coordination takes place with water. Hydrates are preferred solvates in the context of the present invention.

The compounds of this invention may, either by nature of asymmetric centers or by restricted rotation, be present in the form of isomers (enantiomers, diastereomers). Any isomer may be present in which the asymmetric center is in the (R)-, (S)-, or (R,S)-configuration.

It will also be appreciated that when two or more asymmetric centers are present in the compounds of the invention, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the invention.

Geometric isomers by nature of substituents about a double bond or a ring may be present in cis (=Z-) or trans (=E-) form, and both isomeric forms are encompassed within the scope of this invention.

All isomers, whether separated, pure, partially pure, or in racemic mixture, of the compounds of this invention are encompassed within the scope of this invention. The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by resolution.

In addition, all possible tautomeric forms of the compounds described above are included according to the present invention.

The present invention also encompasses all suitable isotopic variants of the compounds according to the invention. An isotopic variant of a compound according to the invention is understood to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the active compound distribution in the body. Due to comparatively easy preparability and detectability, especially compounds labelled with $^{3}H$ or $^{14}C$ isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required. Such modifications of the compounds according to the invention may therefore in some cases also constitute a preferred embodiment of the present invention. Isotopic variants of the compounds according to the invention can be prepared by processes known to those skilled in the art, for example by the methods described below and the methods described in the working examples, by using corresponding isotopic modifications of the particular reagents and/or starting compounds therein.

In the context of the present invention, the substituents and residues have the following meaning, unless specified otherwise:

($C_1$-$C_6$)-Alkyl, ($C_1$-$C_4$)-alkyl and ($C_2$-$C_4$)-alkyl in the context of the invention represent a straight-chain or branched alkyl radical having 1 to 6, 1 to 4 or, respectively, 2 to 4 carbon atoms. There may be mentioned by way of example and preferably: methyl, ethyl, n-propyl, isopropyl, n-butyl, iso-butyl, sec-butyl, tert-butyl, n-pentyl, iso-pentyl, neo-pentyl, n-hexyl, and iso-hexyl.

($C_1$-$C_4$)-Alkoxy in the context of the invention represents a straight-chain or branched alkoxy radical having 1 to 4 carbon atoms. There may be mentioned by way of example and preferably: methoxy, ethoxy, n-propoxy, isopropoxy, n-butoxy, iso-butoxy, sec-butoxy, and tert-butoxy.

Mono-($C_1$-$C_4$)-alkylamino in the context of the invention represents an amino group with a straight-chain or branched alkyl substituent which contains 1 to 4 carbon atoms. There may be mentioned by way of example and preferably: methylamino, ethylamino, n-propylamino, isopropylamino, n-butylamino, and tert-butylamino.

Di-($C_1$-$C_4$)-alkylamino in the context of the invention represents an amino group with two identical or different straight-chain or branched alkyl substituents which each contain 1 to 4 carbon atoms. There may be mentioned by way of example and preferably: N,N-dimethylamino, N,N-diethylamino, N-ethyl-N-methylamino, N-methyl-N-n-propylamino, N-isopropyl-N-methylamino, N-isopropyl-N-n-propylamino, N,N-diisopropylamino, N-n-butyl-N-methylamino, and N-tert-butyl-N-methylamino.

Mono-($C_1$-$C_4$)-alkylaminocarbonyl in the context of the invention represents an amino group which is bonded to the rest of the molecule via a carbonyl group [—C(═O)—] and which has a straight-chain or branched alkyl substituent having 1 to 4 carbon atoms. There may be mentioned by way of example and preferably: methylaminocarbonyl, ethylaminocarbonyl, n-propylaminocarbonyl, isopropylaminocarbonyl, n-butylaminocarbonyl, and tert-butylaminocarbonyl.

Di-($C_1$-$C_4$)-alkylaminocarbonyl in the context of the invention represents an amino group which is bonded to the rest of the molecule via a carbonyl group [—C(═O)—] and which has two identical or different straight-chain or branched alkyl substituents having in each case 1 to 4 carbon atoms. There may be mentioned by way of example and preferably: N,N-dimethylaminocarbonyl, N,N-diethylaminocarbonyl, N-ethyl-N-methylaminocarbonyl, N-methyl-N-n-propylaminocarbonyl, N-isopropyl-N-methylaminocarbonyl, N,N-diisopropylaminocarbonyl, N-n-butyl-N-methylaminocarbonyl, and N-tert-butyl-N-methylaminocarbonyl.

($C_1$-$C_4$)-Alkylcarbonyl in the context of the invention represents a straight-chain or branched alkyl radical having 1 to 4 carbon atoms which is bonded to the rest of the molecule via a carbonyl group [—C(═O)—]. There may be mentioned by way of example and preferably: acetyl, propionyl, n-butyryl, iso-butyryl, n-pentanoyl, and pivaloyl.

($C_1$-$C_4$)-Alkylcarbonylamino in the context of the invention represents an amino group with a straight-chain or branched alkylcarbonyl substituent which contains 1 to 4 carbon atoms in the alkyl radical and is linked to the N atom via the carbonyl group. There may be mentioned by way of example and preferably: acetylamino, propionylamino, n-butyrylamino, iso-butyrylamino, n-pentanoylamino, and pivaloylamino.

($C_3$-$C_6$)-Cycloalkyl in the context of the invention represents a monocyclic, saturated carbocycle having 3 to 6 ring carbon atoms. There may be mentioned by way of example: cyclopropyl, cyclobutyl, cyclopentyl, and cyclohexyl.

($C_3$-$C_6$)-Cycloalkylcarbonyl in the context of the invention represents a monocyclic, saturated carbocycle having 3 to 6 ring carbon atoms which is bonded to the rest of the molecule via a carbonyl group [—C(═O)—]. There may be mentioned by way of example: cyclopropylcarbonyl, cyclobutylcarbonyl, cyclopentylcarbonyl, and cyclohexylcarbonyl.

4- to 10-membered heterocycloalkyl in the context of the invention represents a mono- or bicyclic, saturated heterocycle with 4 to 10 ring atoms in total, which contains one ring nitrogen atom and optionally one further ring heteroatom from the series N or O, and which is bonded via a ring nitrogen atom. 4- to 7-membered heterocycloalkyl representing a monocyclic, saturated heterocycle with 4 to 7 ring atoms in total, including one ring nitrogen atom and optionally one further ring heteroatom from the series N or O, is preferred. Monocyclic, saturated 5- to 7-membered heterocycloalkyl containing one ring nitrogen atom and optionally one further ring heteroatom from the series N or O is particularly preferred. There may be mentioned by way of example: azetidinyl, pyrrolidinyl, pyrazolidinyl, imidazolidinyl, 1,2-oxazolidinyl, 1,3-oxazolidinyl, piperidinyl, piperazinyl, 1,2-oxazinanyl, morpholinyl, azepanyl, 1,4-diazepanyl, 1,4-oxazepanyl, azocanyl, 1,5-diazocanyl, 1,5-oxazocanyl, octahydropyrrolo[3,4-b]pyrrolyl, octahydropyrrolo[3,4-c]pyrrolyl, octahydroindolyl, octahydroisoindolyl, octahydropyrrolo[3,4-b]pyridyl, octahydropyrrolo[1,2-a]-pyrazinyl, decahydroquinolinyl, decahydroisoquinolinyl, 3-azabicyclo[3.1.0]hexyl, 7-azabicyclo-[2.2.1]heptyl, 3-azabicyclo[3.2.0]heptyl, 7-azabicyclo[4.1.0]heptyl, 2,5-diazabicyclo[2.2.1]heptyl, 2-oxa-5-azabicyclo[2.2.1]heptyl, 2-azabicyclo[2.2.2]octyl, 3-azabicyclo[3.2.1]octyl, 8-azabicyclo-[3.2.1]octyl, 8-oxa-3-azabicyclo[3.2.1]octyl, and 3-oxa-9-azabicyclo[3.3.1]nonyl. Preferred are azetidinyl, pyrrolidinyl, pyrazolidinyl, imidazolidinyl, 1,2-oxazolidinyl, 1,3-oxazolidinyl, piperidinyl, piperazinyl, 1,2-oxazinanyl, morpholinyl, azepanyl, 1,4-diazepanyl, and 1,4-oxazepanyl. Particularly preferred are pyrrolidinyl, pyrazolidinyl, imidazolidinyl, 1,2-oxazolidinyl, 1,3-oxazolidinyl, piperidinyl, piperazinyl, 1,2-oxazinanyl, morpholinyl, azepanyl, 1,4-diazepanyl, and 1,4-oxazepanyl.

4- to 6-membered heterocycloalkyl in the context of the invention represents a monocyclic, saturated heterocycle with 4 to 6 ring atoms in total, which contains one or two identical or different ring heteroatoms from the series N, O and S, and which can be bonded via a ring carbon atom or via a ring nitrogen atom (if present). 4- to 6-membered heterocycloalkyl containing one ring nitrogen atom and optionally one further ring heteroatom from the series N, O or S is preferred. 5- or 6-membered heterocycloalkyl containing one ring nitrogen atom and optionally one further ring heteroatom from the series N or O is particularly preferred. There may be mentioned by way of example: azetidinyl, oxetanyl, thietanyl, pyrrolidinyl, pyrazolidinyl, imidazolidinyl, tetrahydrofuranyl, thiolanyl, 1,2-oxazolidinyl, 1,3-oxazolidinyl, 1,3-thiazolidinyl, piperidinyl, piperazinyl, tetrahydropyranyl, tetrahydrothiopyranyl, 1,3-dioxanyl, 1,4-dioxanyl, 1,2-oxazinanyl, morpholinyl, and thiomorpholinyl. Preferred are azetidinyl, pyrrolidinyl, pyrazolidinyl, imidazolidinyl, 1,2-oxazolidinyl, 1,3-oxazolidinyl, 1,3-thiazolidinyl, piperidinyl, piperazinyl, 1,2-oxazinanyl, morpholinyl, and thiomorpholinyl. Particularly preferred are pyrrolidinyl, piperidinyl, piperazinyl, and morpholinyl.

Azetidino, pyrrolidino and piperidino in the context of the invention specifically refer to an N-bonded azetidin-1-yl, pyrrolidin-1-yl and piperidin-1-yl ring, respectively.

An oxo substituent in the context of the invention represents an oxygen atom, which is bonded to a carbon or sulfur atom via a double bond.

In the context of the present invention, for all the radicals which occur several times, the meaning thereof is independent of each other. If radicals in the compounds according to the invention are substituted, the radicals can be mono- or polysubstituted, unless specified otherwise. Substitution by one or by two or three identical or different substituents is preferred. Substitution by one or by two identical or different substituents is particularly preferred.

In a preferred embodiment, the present invention relates to compounds of general formula (I), wherein $R^1$ is chloro or methyl, $R^2$ is methoxy, and G represents the group —$CH_2$—$OR^3$, —$CH_2$—$NR^4R^5$ or —C(=O)—$NR^6R^7$, wherein $R^3$ is ($C_2$-$C_4$)-alkyl substituted with a residue selected from the group consisting of amino, mono-($C_1$-$C_4$)-alkylamino and pyrrolidin-1-yl, or is pyrrolidin-3-yl, $R^4$ is hydrogen or methyl, $R^5$ is ($C_1$-$C_4$)-alkyl substituted with a residue selected from the group consisting of hydroxy, amino, mono-($C_1$-$C_4$)-alkylamino, di-($C_1$-$C_4$)-alkylamino, aminocarbonyl and mono-($C_1$-$C_4$)-alkylaminocarbonyl, or is ($C_1$-$C_4$)-alkylcarbonyl optionally substituted with amino, or is ($C_3$-$C_6$)-cycloalkyl optionally substituted with a residue selected from the group consisting of hydroxy, amino, mono-($C_1$-$C_4$)-alkylamino and di-($C_1$-$C_4$)-alkylamino, or is 5- or 6-membered heterocycloalkyl optionally substituted with one or two residues independently selected from the group consisting of ($C_1$-$C_4$)-alkyl, oxo and amino, or $R^4$ and $R^5$ are joined and, taken together with the nitrogen atom to which they are attached, form a monocyclic, saturated, 4- to 7-membered heterocycloalkyl ring which may contain a second ring heteroatom selected from N and O, and which may be substituted with up to three residues independently selected from the group consisting of ($C_1$-$C_4$)-alkyl, oxo, hydroxy, amino, mono-($C_1$-$C_4$)-alkylamino, di-($C_1$-$C_4$)-alkylamino, ($C_1$-$C_4$)-alkylcarbonyl, ($C_3$-$C_6$)-cycloalkylcarbonyl, aminocarbonyl and mono-($C_1$-$C_4$)-alkylaminocarbonyl, wherein the alkyl groups of said ($C_1$-$C_4$)-alkyl, mono-($C_1$-$C_4$)-alkylamino, di-($C_1$-$C_4$)-alkylamino and ($C_1$-$C_4$)-alkylcarbonyl residues, for their part, are optionally substituted with hydroxy, $R^6$ is hydrogen, $R^7$ is 5- or 6-membered heterocycloalkyl optionally substituted with one or two residues independently selected from the group consisting of ($C_1$-$C_4$)-alkyl, oxo and amino, or $R^6$ and $R^7$ are joined and, taken together with the nitrogen atom to which they are attached, form a monocyclic, saturated, 5- to 7-membered heterocycloalkyl ring which may contain a second ring heteroatom selected from N and O, and which may be substituted with one or two residues independently selected from the group consisting of ($C_1$-$C_4$)-alkyl, oxo, hydroxy, amino, mono-($C_1$-$C_4$)-alkylamino, di-($C_1$-$C_4$)-alkylamino and aminocarbonyl.

In a distinct embodiment, the present invention relates to compounds of general formula (I), wherein $R^1$ is methyl, and $R^2$ is methoxy.

In a further distinct embodiment, the present invention relates to compounds of general formula (I), wherein G represents the group —$CH_2$—$NR^4R^5$, wherein $R^4$ is hydrogen, and $R^5$ is 5- or 6-membered heterocycloalkyl optionally substituted with one or two residues independently selected from the group consisting of ($C_1$-$C_4$)-alkyl and oxo.

In another distinct embodiment, the present invention relates to compounds of general formula (I), wherein G represents the group —$CH_2$—$NR^4R^5$, wherein $R^4$ and $R^5$ are joined and, taken together with the nitrogen atom to which they are attached, form a monocyclic, saturated, 5- to 7-membered heterocycloalkyl ring which may contain a second ring heteroatom selected from N and O, and which may be substituted with up to three residues independently selected from the group consisting of ($C_1$-$C_4$)-alkyl, oxo, hydroxy, amino, mono-($C_1$-$C_4$)-alkylamino, di-($C_1$-$C_4$)-alkylamino and aminocarbonyl.

In yet another distinct embodiment, the present invention relates to compounds of general formula (I), wherein G represents the group —C(═O)—$NR^6R^7$, wherein $R^6$ is hydrogen, and $R^7$ is 5- or 6-membered heterocycloalkyl optionally substituted with one or two residues independently selected from the group consisting of ($C_1$-$C_4$)-alkyl and oxo.

In yet another distinct embodiment, the present invention relates to compounds of general formula (I), wherein G represents the group —C(═O)—$NR^6R^7$, wherein $R^6$ and $R^7$ are joined and, taken together with the nitrogen atom to which they are attached, form a monocyclic, saturated, 5- to 7-membered heterocycloalkyl ring which may contain a second ring nitrogen atom, and which may be substituted with one or two residues independently selected from the group consisting of ($C_1$-$C_4$)-alkyl, oxo, hydroxy, amino, mono-($C_1$-$C_4$)-alkylamino, di-($C_1$-$C_4$)-alkylamino and aminocarbonyl.

In a particularly preferred embodiment, the present invention relates to compounds of general formula (I), wherein $R^1$ is methyl, $R^2$ is methoxy, and G represents the group —$CH_2$—$NR^4R^5$ or —C(═O)—$NR^6R^7$, wherein $R^4$ is hydrogen, $R^5$ is ($C_1$-$C_4$)-alkyl substituted with amino, methylamino or aminocarbonyl, or is ($C_1$-$C_4$)-alkylcarbonyl substituted with amino, or is 2-oxopyrrolidin-3-yl or 2-oxopiperidin-3-yl, or $R^4$ and $R^5$ are joined and, taken together with the nitrogen atom to which they are attached, form a pyrrolidin-1-yl, piperidin-1-yl or piperazin-1-yl ring each of which may be substituted with one or two residues independently selected from the group consisting of methyl, oxo, hydroxy, amino, methylamino, dimethylamino and aminocarbonyl, $R^6$ is hydrogen, $R^7$ is 2-oxopyrrolidin-3-yl or 2-oxopiperidin-3-yl, or $R^6$ and $R^7$ are joined and, taken together with the nitrogen atom to which they are attached, form a pyrrolidin-1-yl, piperidin-1-yl or piperazin-1-yl ring each of which may be substituted with one or two residues independently selected from the group consisting of methyl, oxo, hydroxy, amino, methylamino, dimethylamino and aminocarbonyl.

The definitions of residues indicated specifically in the respective combinations or preferred combinations of residues are also replaced as desired by definitions of residues of other combinations, irrespective of the particular combinations indicated for the residues. Combinations of two or more of the abovementioned preferred ranges are particularly preferred.

The compounds of the general formula (I) can be prepared by various synthetic routes which are primarily governed by the nature of the particular G group chosen (see definitions above).

Thus, in another embodiment, the present invention relates to a process for preparing the compounds of the general formula (I), characterized in that 4-aminopyrrolo[2,1-f][1,2,4]triazine of formula (II)

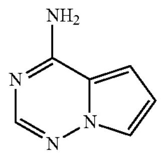

(II)

is either

[A] reacted with formaldehyde and an amine of formula (III)

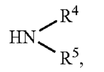

(III)

wherein $R^4$ and $R^5$ have the meanings described above, in the presence of an acid to give a compound of formula (IV)

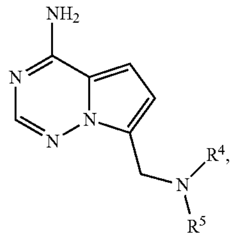

(IV)

wherein $R^4$ and $R^5$ have the meanings described above, then brominated to a compound of formula (V)

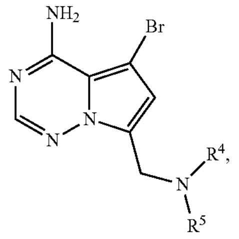

(V)

wherein $R^4$ and $R^5$ have the meanings described above, and subsequently coupled with a benzothiophen-2-yl boronate of formula (VI)

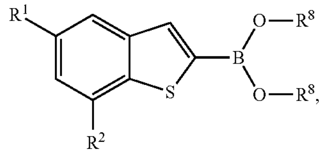

(VI)

wherein $R^1$ and $R^2$ have the meanings described above, and $R^8$ represents hydrogen or ($C_1$-$C_4$)-alkyl, or both $R^8$ residues are linked together to form a —$(CH_2)_2$—, $-C(CH_3)_2-C(CH_3)_2-$, $-(CH_2)_3-$, $-CH_2-C(CH_3)_2-CH_2-$ or $-C(=O)-CH_2-N(CH_3)-CH_2-C(=O)-$ bridge, in the presence of a palladium catalyst and a base to yield the target compound of formula (I-A)

(I-A)

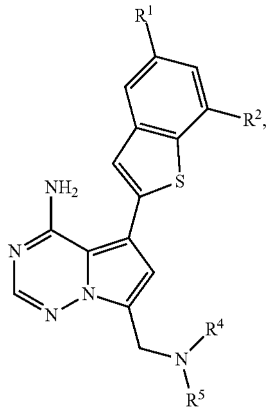

wherein $R^1$, $R^2$, $R^4$ and $R^5$ have the meanings described above, or

[B] treated with N,N-dimethylformamide in the presence of phosphoryl chloride to give the formyl compound of formula (VII)

(VII)

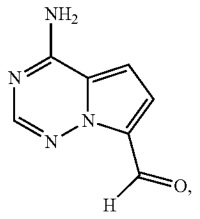

then brominated to the compound of formula (VIII)

(VIII)

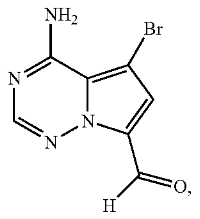

and subsequently coupled with a benzothiophen-2-yl boronate of formula (VI)

(VI)

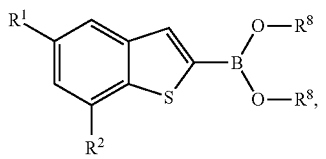

wherein $R^1$, $R^2$ and $R^8$ have the meanings described above, in the presence of a palladium catalyst and a base to give a compound of formula (IX)

(IX)

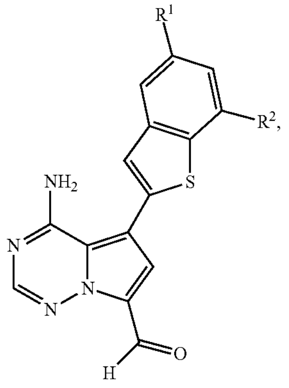

wherein $R^1$ and $R^2$ have the meanings described above, which then is either

[B-1] reacted with an amine of formula (III)

(III)

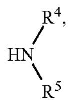

wherein $R^4$ and $R^5$ have the meanings described above, in the presence of an acid and a reducing agent to yield the target compound of formula (I-A)

(I-A)

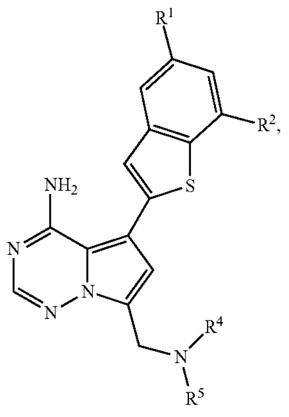

wherein $R^1$, $R^2$, $R^4$ and $R^5$ have the meanings described above, or

[B-2] oxidized to a carboxylic acid of formula (X)

(X)

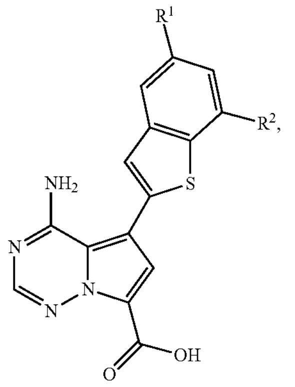

wherein $R^1$ and $R^2$ have the meanings described above, and finally coupled with an amine of formula (XI)

(XI)

wherein $R^6$ and $R^7$ have the meanings described above, in the presence of a condensing agent to yield the target compound of formula (I-B)

(I-B)

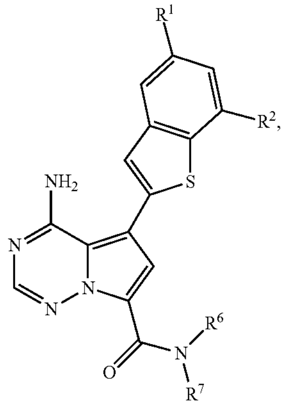

wherein $R^1$, $R^2$, $R^6$ and $R^7$ have the meanings described above, or

[B-3] reduced to an alcohol of formula (XII)

(XII)

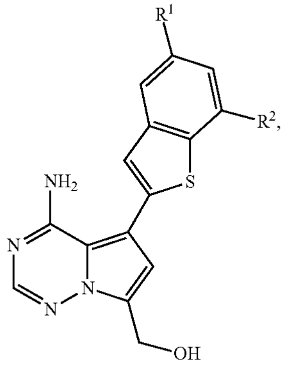

wherein $R^1$ and $R^2$ have the meanings described above, converted into the corresponding halomethyl derivative of formula (XIII)

(XIII)

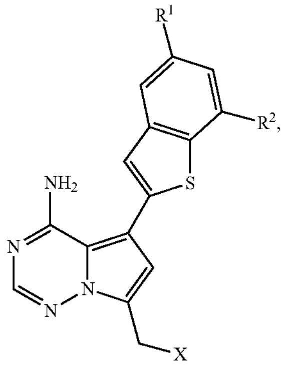

wherein $R^1$ and $R^2$ have the meanings described above, and

X is chloro, bromo or iodo, and finally treated with an alcohol of formula (XIV)

$R^3$—OH (XIV), wherein $R^3$ has the meaning described above, in the optional presence of a base to yield the target compound of formula (I-C)

(I-C)

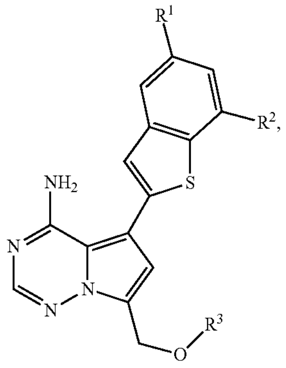

wherein $R^1$, $R^2$ and $R^3$ have the meanings described above, optionally followed, where appropriate, by (i) separating the compounds of formula (I) thus obtained into their respective enantiomers and/or diastereomers, preferably using chromatographic methods, and/or (ii) converting the compounds of formula (I) into their respective hydrates, solvates, salts and/or hydrates or solvates of the salts by treatment with the corresponding solvents and/or acids or bases.

Compounds of the invention having the formula (I-D)

(I-D)

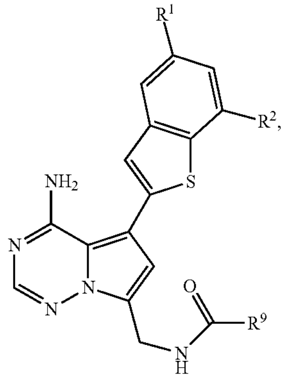

wherein $R^1$ and $R^2$ have the meanings described above, and $R^9$ is optionally substituted ($C_1$-$C_4$)-alkyl [i.e., $R^9$—C(═O)— represents optionally substituted ($C_1$-$C_4$)-alkylcarbonyl], can be prepared by converting the aforementioned aldehyde intermediate of formula (IX)

(IX)

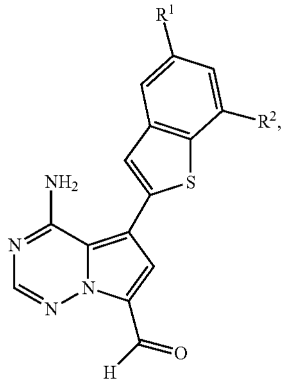

wherein $R^1$ and $R^2$ have the meanings described above, into the corresponding oxime of formula (XV)

(XV)

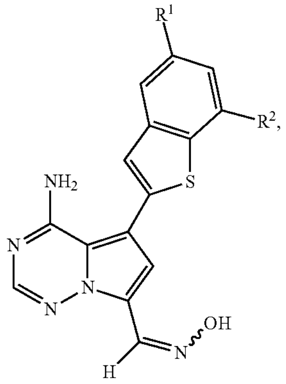

wherein $R^1$ and $R^2$ have the meanings described above, which is then reduced to the aminomethyl compound of formula (XVI)

(XVI)

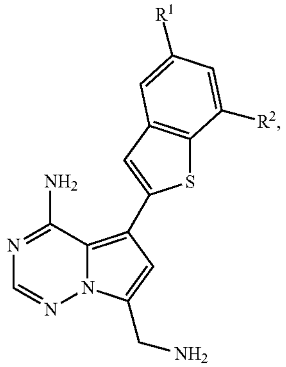

wherein $R^1$ and $R^2$ have the meanings described above, and subsequently coupled in the presence of a condensing agent with a carboxylic acid of formula (XVII)

(XVII)

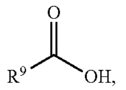

wherein $R^9$ has the meaning described above.

Compounds of the invention having the formula (I-E)

(I-E)

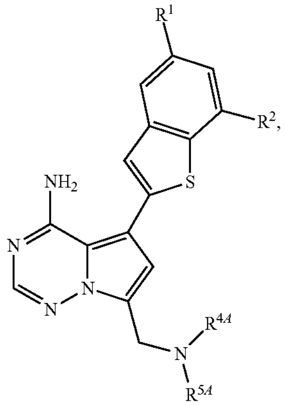

wherein $R^1$ and $R^2$ have the meanings described above, and $R^{4A}$ and $R^{5A}$ are joined and, taken together with the nitrogen atom to which they are attached, form an optionally substituted imidazol-1-yl or 1,2,4-triazol-1-yl ring, can be prepared by reacting the aforementioned halomethyl intermediate of formula (XIII)

(XIII)

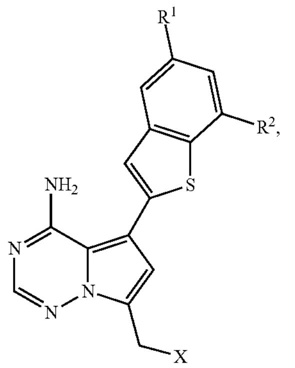

wherein $R^1$ and $R^2$ have the meanings described above, and

X is chloro, bromo or iodo, with an appropriate 1H-imidazole or 1H-1,2,4-triazole derivative generalized by formula (XVIII)

(XVIII)

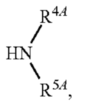

wherein $R^{4A}$ and $R^{5A}$ have the meanings described above.

The compounds of the formulae (I-A), (I-B), (I-C), (I-D) and (I-E), which can be prepared by the processes described above, each represent a particular subset of the compounds of the general formula (I).

Process step [A] (II)→(IV), representing a Mannich-type aminomethylation reaction, is carried out in the usual way by treating the pyrrolotriazine (II) with a mixture of aqueous formaldehyde and amine (III) in the presence of an acid catalyst such as formic acid or acetic acid. Preferably, acetic acid is used both as catalyst and solvent. The reaction is usually performed at a temperature ranging from +20° C. to +80° C. [see also preparation methods described in Int. Pat. Appl. WO 2007/064931-A2].

As the brominating agent for process steps [A] (IV)→(V) and [B] (VII)→(VIII), preferably N-bromosuccinimide (NBS),1,3-dibromo-5,5-dimethylhydantoin (DBDMH) or elemental bromine are used. The reactions are generally carried out in an inert solvent, such as dichloromethane, chloroform, tetrahydrofuran, acetonitrile or N,N-dimethylformamide (DMF), within a temperature range from −78° C. to +25° C.

The coupling reactions [A] (V)+(VI)→(I-A) and [B] (VIII)+(VI)→(IX) ["Suzuki-Miyaura coupling"] are generally carried out in an inert solvent with the aid of a palladium catalyst and an aqueous base. Palladium catalysts suitable for this purpose include, for example, palladium(II) acetate, palladium(H) chloride, bis(triphenylphosphine)palladium (H) chloride, bis(acetonitrile)palladium(II) chloride, [1,1'-bis(diphenylphosphino)ferrocene]palladium(II) chloride, tetrakis(triphenylphosphine)palladium(0), bis(dibenzylideneacetone)palladium(0), and tris(dibenzylideneacetone)dipalladium(0), optionally in combination with other phosphine ligands such as, for example, 2-dicyclohexylphosphino-2',4',6'-triisopropylbiphenyl (X-Phos), 2-dicyclohexylphosphino-2',6'-dimethoxybiphenyl (S-Phos), 4,5-bis(diphenylphosphino)-9,9-dimethylxanthene (Xantphos), or 4-(di-tert-butylphosphino)-N,N-dimethylaniline. Also, palladium pre-catalysts from which the catalytically active species is generated under the reaction conditions, such as (2'-aminobiphenyl-2-yl)(chloro)palladium-dicyclohexyl(2',4',6'-triisopropylbiphenyl-2-yl)phosphine, can be used [see, for example, S. Kotha et al., *Tetrahedron* 58, 9633-9695 (2002); T. E. Barder et al., *J. Am. Chem. Soc.* 127 (13), 4685-4696 (2005); S. L. Buchwald et al., *J. Am. Chem. Soc.* 132 (40), 14073-14075 (2010), and further references cited therein].

Suitable bases for these coupling reactions are in particular alkali bicarbonates, such as sodium or potassium bicarbonate, alkali carbonates, such as sodium, potassium or caesium carbonate, alkali phosphates, such as sodium or potassium phosphate, or alkali fluorides, such as potassium or caesium fluoride. Usually, these bases are employed as aqueous solutions. The reactions are carried out in organic solvents that are inert under the reaction conditions. Preferably, water-miscible organic solvents, such as 1,2-dimethoxyethane, tetrahydrofuran, 1,4-dioxane, acetonitrile, N,N-dimethylformamide (DMF) or dimethylsulfoxide (DMSO), are employed but other inert solvents, such as dichloromethane or toluene, may also be used. The coupling reactions are usually performed at a temperature ranging from +40° C. to +120° C.

Process step [B] (II)→(VII) ["Vilsmeier-Haack formylation"] is carried out in the usual manner by treating the pyrrolotriazine (II) in N,N-dimethylformamide (DMF) solvent with phosphoryl chloride. The reaction is usually performed at a temperature from 0° C. to +80° C.

Reducing agents suitable for the reductive amination reaction [B-1] (IX)+(III)→(I-A) are customary alkali borohydrides, such as lithium borohydride, sodium borohydride, potassium borohydride, sodium cyanoborohydride or sodium triacetoxyborohydride. These transformations are generally carried out in the presence of an acid, preferably acetic acid, in an alcohol or ether solvent, such as methanol, ethanol, isopropanol, tetrahydrofuran or 1,4-dioxane, within a temperature range from 0° C. to +80° C., depending on the reactivity of the amine component (III) and/or the particular borohydride used.

For the oxidation reaction in process step [B-2] (IX)→(X), oxidation with sodium chlorite in the presence of a hypochlorite scavenger such as 2-methyl-2-butene represents the method of choice [cf. H. W. Pinnick et al., *Tetrahedron* 37, 2091-2096 (1981); A. Raach and O. Reiser, *J. Prakt. Chem.* 342 (6), 605-608 (2000), and references cited therein]. The reaction is usually carried out in a tetrahydrofuran/water mixture at a temperature between 0° C. and ambient temperature.

Condensing agents suitable for process step [B-2] (X)+(XI)→(I-B) [amide formation] include, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide (EDC), phosgene derivatives such as N,N'-carbonyldiimidazole (CDI) or isobutyl chloroformate, α-chloroenamines such as 1-chloro-2-methyl-1-dimethylamino-1-propene, phosphorus compounds such as propanephosphonic anhydride, diethyl cyanophosphonate, bis(2-oxo-3-oxazolidinyl)phosphoryl chloride, benzotriazol-1-yloxy-tris(dimethylamino)phosphonium hexafluorophosphate (BOP) or benzotriazol-1-yloxy-tris(pyrrolidino)phosphonium hexafluorophosphate (PyBOP), and uronium compounds such as O-(benzotriazol- 1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)N,N,N',N'-tetramethyluronium hexafluorophosphate (HATU) or O-(1H-6-chlorobenzotriazol-1-yl)-1,1,3,3-tetramethyluronium tetrafluoroborate (TCTU), if appropriate in combination with further auxiliaries, such as 1-hydroxybenzotriazole (HOBt) or N-hydroxysuccinimide (HOSu), and/or bases such as alkali carbonates, for example sodium or potassium carbonate, or organic amine bases, such as triethylamine, N-methylpiperidine, N-methylmorpholine (NMM), N,N-diisopropylethylamine (DIPEA), pyridine or 4-N,N-dimethylaminopyridine (DMAP). Preference is given to using O-(7-azabenzotriazol-1-yl)-N,N,N',N'-tetramethyluronium hexafluorophosphate (HATU) or O-(benzotriazol-1-yl)-N,N,N',N'-tetramethyluronium tetrafluoroborate (TBTU) in combination with N,N-diisopropylethylamine (DIPEA) and optionally 1-hydroxybenzotriazole (HOBt).

Inert solvents for process step [B-2] (X)+(XI)→(I-B) are, for example, ethers such as diethyl ether, tert-butyl methyl ether, tetrahydrofuran, 1,4-dioxane or 1,2-dimethoxyethane, hydrocarbons such as benzene, toluene, xylene, hexane or cyclohexane, halogenated hydrocarbons such as dichloromethane, trichloromethane, carbon tetrachloride, 1,2-dichloroethane, trichloroethylene or chlorobenzene, or other solvents such as acetone, acetonitrile, ethyl acetate, pyridine, dimethylsulfoxide (DMSO), N,N-dimethylformamide (DMF), N,N'-dimethylpropylene urea (DMPU) or N-methylpyrrolidinone (NMP). It is also possible to use mixtures of these solvents. Preference is given to using dichloromethane, tetrahydrofuran, N,N-dimethylformamide or mixtures thereof. The reactions are generally carried out at a temperature ranging from 0° C. to +60° C., preferably at +10° C. to +40° C.

The aldehyde-to-alcohol conversion in process step [B-3] (IX)→(XII) may be accomplished by several customary reduction methods. Preferably, sodium borohydride in an alcoholic solvent, such as methanol or ethanol, is used.

For the hydroxy-to-halogen transformation in process step [B-3] (XII)→(XIII), various standard methods and reagents that are well known in the art may be employed. Reagents of choice are thionyl chloride [for X═Cl], tetrabromomethane/triphenylphosphine [for X═Br], and iodine/triphenylphosphine [for X═I]. The preparation of 7-(chloromethyl) derivatives (XIII) [X═Cl] is preferred for reasons of convenience of work-up and compound stability.

Bases suitable for the process step [B-3] (XIII)+(XIV)→(I-C) [ether formation] are in particular alkali carbonates such as lithium, sodium, potassium or caesium carbonate, alkali acetates such as sodium or potassium acetate, or customary tertiary amine bases such as triethylamine, N-methylmorpholine, N-methylpiperidine, N,N-diisopropylethylamine or pyridine. Preference is given to N,N-diisopropylethylamine (DIPEA).

The reaction (XIII)+(XIV)→(I-C) is performed in an inert solvent, such as dichloromethane, 1,2-dichloroethane, tetrahydrofuran or N,N-dimethylformamide (DMF), or without solvent, using an excess of alcohol (XIV), at a temperature ranging from +20° C. to +150° C. Advantageously, the conversion is carried out by means of a microwave reactor device. Addition of a quaternary ammonium bromide as alkylation catalyst, such as tetra-n-butylammonium bromide, N-benzyltriethylammonium bromide or N,N,N-trimethylhexadecan-1-ammonium bromide, may also be beneficial.

The reaction sequence (XII)→(XIII)→(I-C) may be carried out in two separate steps, i.e. with isolation and purification of the intermediate compound (XIII), or it may be performed using a one-pot procedure, i.e. employing the crude intermediate (XIII) as obtained in the preparation reaction.

The aldoxime (XV) is readily available from the aldehyde intermediate (IX) by condensation with hydroxylamine in an alcohol/water mixture. Subsequent reduction to the primary amine (XVI) is effected by treatment with zinc powder in methanolic hydrochloric acid, and amide formation (XVI)+(XVII)→(I-D) is performed under similar conditions as described above for process step [B-2] (X)+(XI)→(I-B).

The reaction (XIII)+(XVIII)→(I-E) is usually carried out in an inert solvent, such as dichloromethane, 1,2-dichloroethane, tetrahydrofuran or N,N-dimethylformamide (DMF), at a temperature ranging from +20° C. to +100° C. The conversion can be accomplished in the presence of an auxiliary base [cf. reaction (XIII)+(XIV)→(I-C)], or it may proceed without a separate base, using an excess of the azole component (XVIII).

In cases where a primary or secondary amine moiety forms part of the G group in the target compounds of formula (I), it may sometimes be appropriate in the preparation reactions described above to use a protected derivative of this amine as reaction component instead of the free amine. For this purpose, conventional temporary amino-protecting groups, such as acyl groups (e.g., acetyl or trifluoroacetyl) or carbamate-type protecting groups (e.g., a Boc-, Cbz- or Fmoc-group), may be employed. A Boc (tert-butoxycarbonyl) group is preferably used. Similarly, a hydroxy function being part of the G group may temporarily be blocked in precursor compounds and process intermediates, for example as a tetrahydropyranyl (THP) ether or as a silyl ether derivative, such as a trimethylsilyl or tert-butyldimethylsilyl ether.

These protecting groups may then be cleaved off concomitantly during aqueous work-up and purification procedures, or they are removed in a subsequent, separate reaction step using standard methods well known in the art. The preparation of such protected intermediates from the corresponding free amines or alcohols is likewise readily accomplished following general procedures described in the literature [see, for example, T. W. Greene and P. Wuts, *Protective Groups in Organic Synthesis*, Wiley, New York, 1999].

Certain types of protected (i.e. acylated) amine derivatives exert significant FGFR-inhibiting activity by their own. Accordingly, such compounds are also encompassed by the general formula (I) as defined above.

The preparation of the compounds of the invention may be illustrated by means of the following synthesis schemes:

Scheme 1

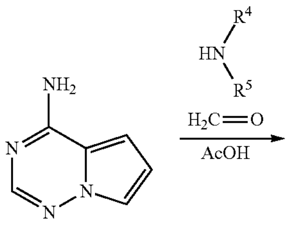

-continued
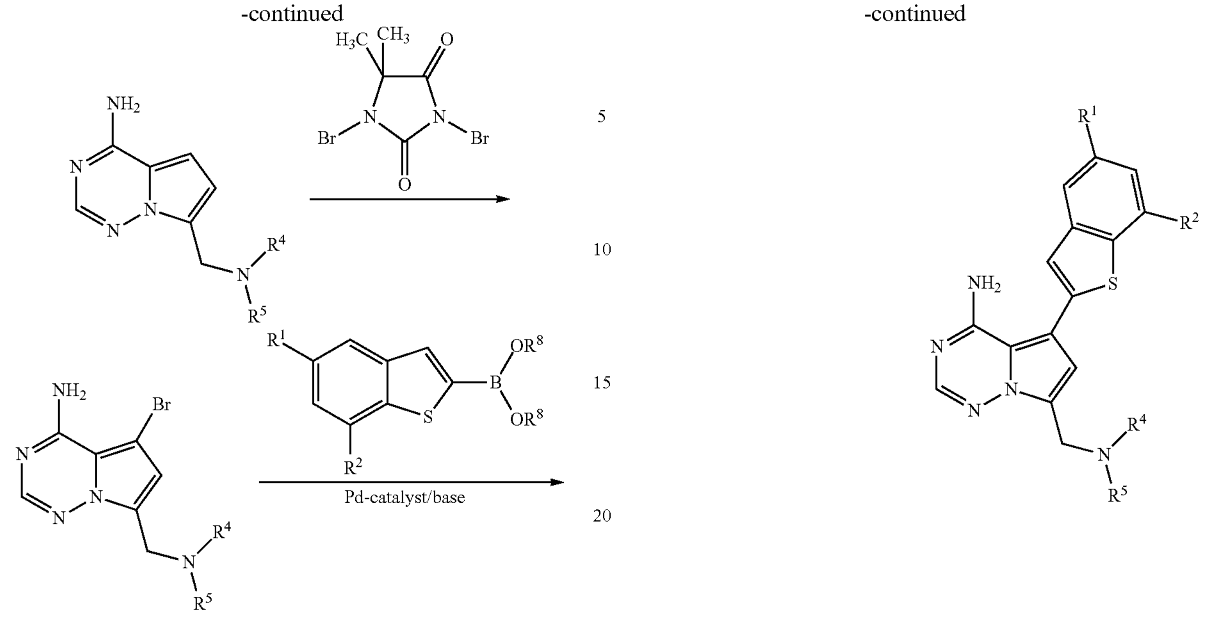
-continued
Scheme 2
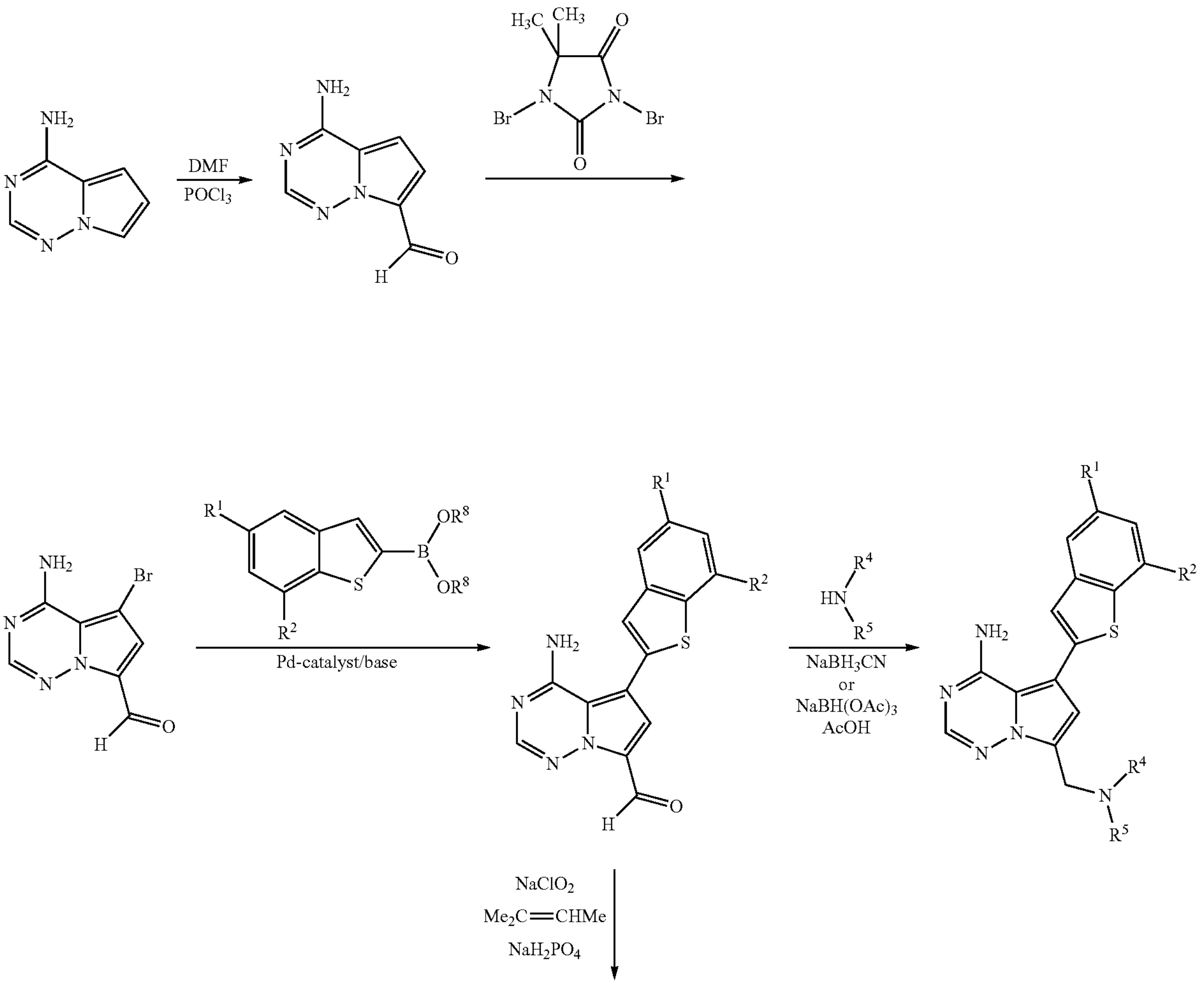

-continued
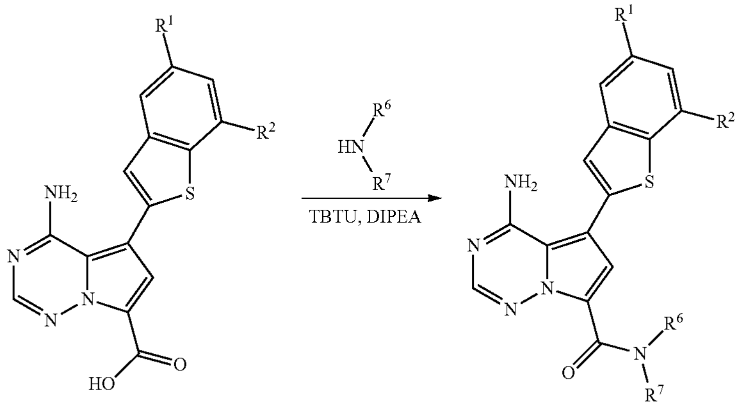
Scheme 3
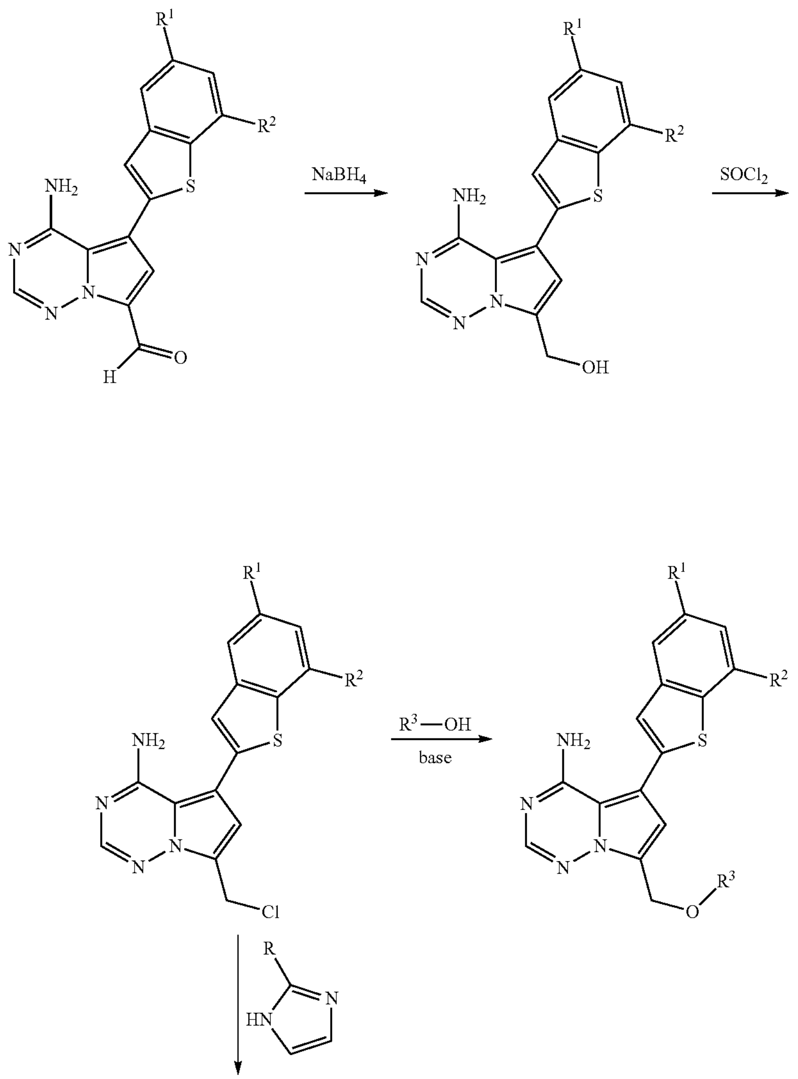

-continued
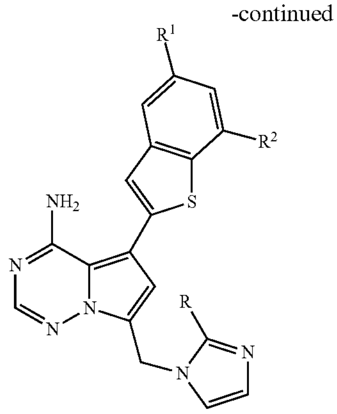
[R = hydrogen, ($C_1$—$C_4$)-alkyl or cyano].
Scheme 4
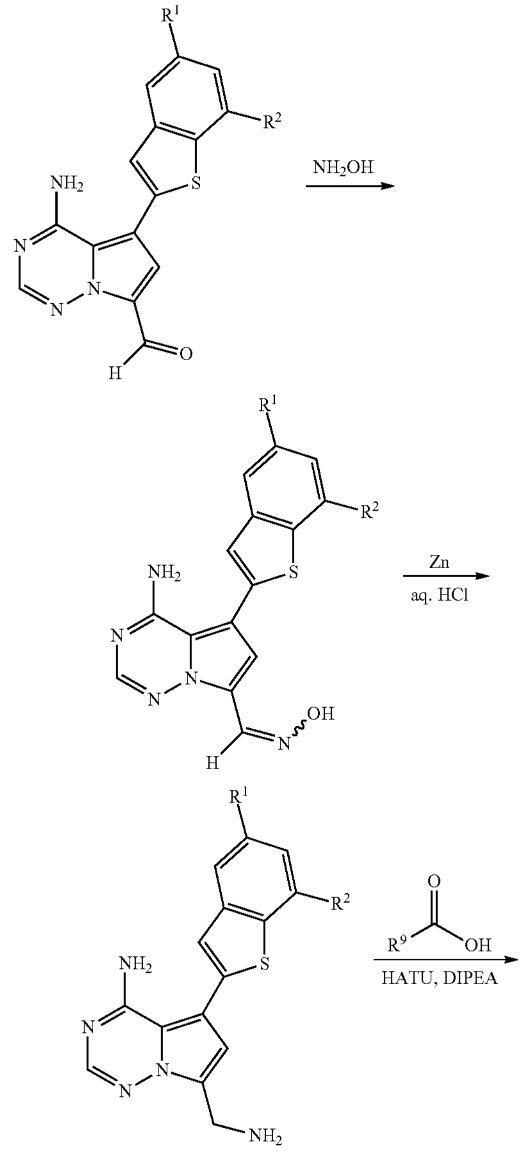
-continued
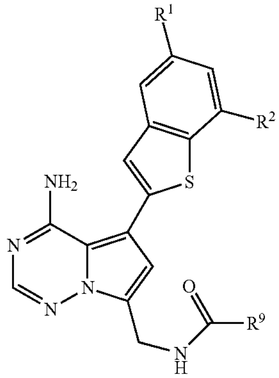
The starting compound 4-aminopyrrolo[2,1-f][1,2,4]triazine of formula (II) is readily available by a four-step reaction sequence that has been described previously [Scheme 5; see Int. Pat. Appl. WO 2007/064931-A2 (Intermediate A)]:
Scheme 5
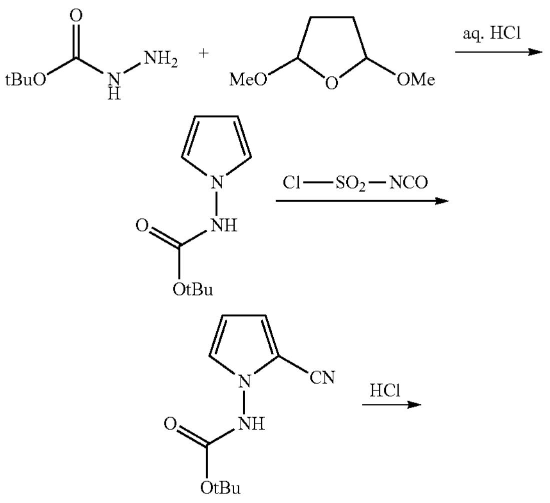

-continued

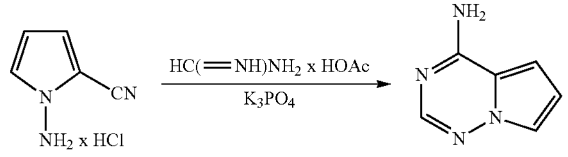

(II)

The benzothiophen-2-yl boronates of formula (VI) can conveniently be prepared starting from the substituted thiophenol derivatives of formula (XIX) (see Scheme 6 below). Alkylation with bromoacetal (XX) and subsequent polyphosphoric acid-mediated cyclization provides the benzothiophene intermediates of formula (XXII) which are then metalated in 2-position and reacted with a trialkyl borate. Alkaline work-up affords the free (benzothiophen-2-yl)boronic acids of formula (VIa) which may be transformed, if desired, into cyclic boronates, e.g. so-called MIDA boronates of formula (VIb), by standard procedures known in the art [see, for example, D. M. Knapp et al., *J. Am. Chem. Soc.* 131 (20), 6961-6963 (2009)].

Scheme 6

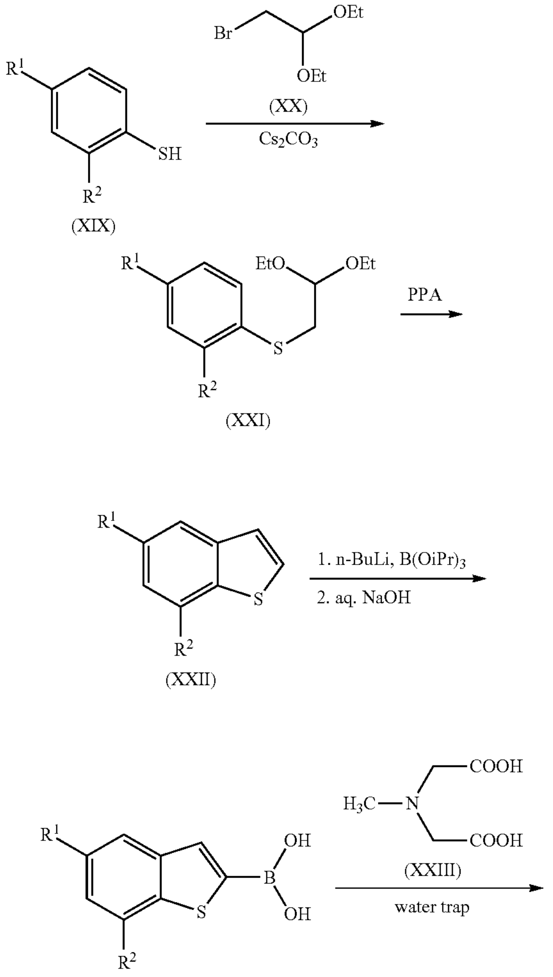

(XX)

(XIX)

(XXI)

(XXII)

(XXIII)

(VIa)

-continued

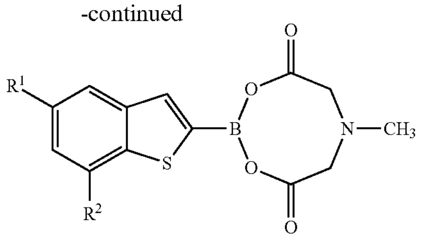

(VIb)

[cf. P.A. Plé and L.J. Marnett, *J. Heterocyclic Chem.* 25 (4), 1271-1272 (1988); A. Venturelli et al., *J. Med. Chem.* 50 (23), 5644-5654 (2007)].

The compounds of the formulae (III), (XI), (XIV), (XVII), (XVIII), (XIX), (XX) and (XXIII) are either commercially available, known from the literature, or can be prepared from readily available starting materials by adaptation of standard methods described in the literature. Detailed procedures and literature references for preparing the starting materials can also be found in the Experimental Part in the section on the preparation of the starting materials and intermediates.

The compounds of the present invention have valuable pharmacological properties and can be used for the prevention and treatment of disorders in humans and other mammals.

The compounds of the present invention are potent inhibitors of the activity or expression of receptor tyrosine kinases, particularly of the FGFR kinases, and most notably of the FGFR-1 and FGFR-3 kinases. Accordingly, in another embodiment, the present invention provides a method of treating disorders relating to or mediated by the activity of FGFR kinases in a patient in need of such treatment, comprising administering to the patient an effective amount of a compound of formula (I) as defined above. In certain embodiments, the disorders relating to the activity of FGFR kinases are proliferative disorders, in particular cancer and tumor diseases.

In the context of the present invention, the term "treatment" or "treating" includes inhibiting, delaying, relieving, mitigating, arresting, reducing, or causing the regression of a disease, disorder, condition, or state, the development and/or progression thereof, and/or the symptoms thereof. The term "prevention" or "preventing" includes reducing the risk of having, contracting, or experiencing a disease, disorder, condition, or state, the development and/or progression thereof, and/or the symptoms thereof. The term prevention includes prophylaxis. Treatment or prevention of a disorder, disease, condition, or state may be partial or complete.

The term "proliferative disorder" includes disorders involving the undesired or uncontrolled proliferation of a cell. The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, isomer, polymorph, metabolite, hydrate or solvate thereof which is effective to treat or prevent the disorder.

Throughout this document, for the sake of simplicity, the use of singular language is given preference over plural language, but is generally meant to include the plural language if not otherwise stated. For example, the expression "A method of treating a disease in a patient, comprising administering to a patient an effective amount of a compound of formula (I)" is meant to include the simultaneous treatment of more than one disease as well as the administration of more than one compound of formula (I).

Proliferative disorders that can be treated and/or prevented with the compounds of the present invention particularly include, but are not limited to, the group of cancer and tumor diseases. These are understood as meaning, in particular, the following diseases, but without being limited to them: mammary carcinomas and mammary tumors (ductal and lobular forms, also in situ), tumors of the respiratory tract (small cell and non-small cell lung carcinoma, parvicellular and non-parvicellular carcinoma, bronchial carcinoma, bronchial adenoma, pleuropulmonary blastoma), cerebral tumors (e.g. of the brain stem and of the hypothalamus, astrocytoma, glioblastoma, medulloblastoma, ependymoma, and neuro-ectodermal and pineal tumors), tumors of the digestive organs (oesophagus, stomach, gall bladder, small intestine, large intestine, rectum, anus), liver tumors (inter alia hepatocellular carcinoma, cholangiocellular carcinoma and mixed hepatocellular and cholangiocellular carcinoma), tumors of the head and neck region (larynx, hypopharynx, nasopharynx, oropharynx, lips and oral cavity), skin tumors (squamous epithelial carcinoma, Kaposi sarcoma, malignant melanoma, Merkel cell skin cancer and non-melanomatous skin cancer), tumors of soft tissue (inter alia soft tissue sarcomas, osteosarcomas, malignant fibrous histiocytomas, lymphosarcomas and rhabdomyosarcomas), tumors of the eyes (inter alia intraocular melanoma, uveal melanoma and retinoblastoma), tumors of the endocrine and exocrine glands (e.g. thyroid and parathyroid glands, pancreas and salivary gland), tumors of the urinary tract (tumors of the bladder, penis, kidney, renal pelvis and ureter), tumors of the reproductive organs (carcinomas of the endometrium, cervix, ovary, vagina, vulva and uterus in women, and carcinomas of the prostate and testicles in men), as well as distant metastases thereof. These disorders also include proliferative blood diseases in solid form and as circulating blood cells, such as lymphomas, leukaemias and myeloproliferative diseases, e.g. acute myeloid, acute lymphoblastic, chronic lymphocytic, chronic myelogenic and hairy cell leukaemia, and AIDS-related lymphomas, Hodgkin's lymphomas, non-Hodgkin's lymphomas, cutaneous T-cell lymphomas, Burkitt's lymphomas, and lymphomas in the central nervous system.

Due to their activity and selectivity profile, the compounds of the present invention are believed to be particularly suitable for the treatment of breast (mammary), lung, stomach (gastric), bladder and ovary cancer and tumor diseases. Furthermore, the compounds of the present invention may be especially suited for the prevention or suppression of tumor metastasis in general.

Other proliferative disorders that can be treated and/or prevented with the compounds and methods of the present invention include psoriasis, keloids and other hyperplasias affecting the skin, bullous disorders associated with subepidermal blister formation including bullous pemphigoid, erythema multiforme and dermatitis herpetiformis, fibrotic disorders such as lung fibrosis, atherosclerosis, restenosis and hepatic cirrhosis, renal diseases including mesangial cell proliferative disorders, glomerulopathies, glomerulonephritis, diabetic nephropathy, malignant nephrosclerosis and polycystic kidney disease, benign prostate hyperplasia (BPH), angiogenic or blood vessel proliferative disorders, and thrombotic microangiopathy syndromes.

The compounds of the present invention are also useful for the treatment and/or prevention of ophthalmological diseases such as, for example, age-related macular degeneration (AMD), dry macular degeneration, ischemic retinal vein occlusion, diabetic macula edema, diabetic retinopathy, retinopathy of prematurity, and other retinopathies.

Other conditions that may be treated and/or prevented by administering a compound of the present invention include gynaecological diseases such as endometriosis, myoma and ovarian cysts, metabolic disorders related to adipogenesis, bile metabolism, phosphate metabolism, calcium metabolism and/or bone mineralization, skeletal disorders such as, for example, dwarfism, achondrodysplasia and Pfeiffer syndrome, cartilage diseases such as osteoarthritis and polyarthritis, rheumatoid arthritis, calvities, and transplant rejection.

The diseases mentioned above have been well characterized in humans, but also exist with a comparable aetiology in other mammals, and can be treated in those with the compounds and methods of the present invention.

Thus, the present invention further relates to the use of the compounds according to the invention for the treatment and/or prevention of disorders, especially of the aforementioned disorders.

The present invention further relates to the use of the compounds according to the invention for preparing a pharmaceutical composition for the treatment and/or prevention of disorders, especially of the aforementioned disorders.

The present invention further relates to the use of the compounds according to the invention in a method for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

Compounds of the present invention may be administered as the sole pharmaceutical agent or in combination with one or more additional therapeutic agents as long as this combination does not lead to undesirable and/or unacceptable side effects. Such combination therapy includes administration of a single pharmaceutical dosage formulation which contains a compound of formula (I), as defined above, and one or more additional therapeutic agents, as well as administration of a compound of formula (I) and each additional therapeutic agent in its own separate pharmaceutical dosage formulation. For example, a compound of formula (I) and a therapeutic agent may be administered to the patient together in a single (fixed) oral dosage composition such as a tablet or capsule, or each agent may be administered in separate dosage formulations.

Where separate dosage formulations are used, the compound of formula (I) and one or more additional therapeutic agents may be administered at essentially the same time (i.e., concurrently) or at separately staggered times (i.e., sequentially).

In particular, the compounds of the present invention may be used in fixed or separate combination with other anti-cancer agents such as alkylating agents, anti-metabolites, plant-derived anti-tumor agents, hormonal therapy agents, topoisomerase inhibitors, tubulin inhibitors, kinase inhibitors, targeted drugs, antibodies, antibody-drug conjugates (ADCs), immunologicals, biological response modifiers, anti-angiogenic compounds, and other anti-proliferative, cytostatic and/or cytotoxic substances. In this regard, the following is a non-limiting list of examples of secondary agents that may be used in combination with the compounds of the present invention: Abarelix, abiraterone, aclarubicin, afatinib, aflibercept, aldesleukin, alemtuzumab, alitretinoin, alpharadin, altretamine, aminoglutethimide, amonafide, amrubicin, amsacrine, anastrozole, andromustine, arglabin, asparaginase, axitinib, 5-azacitidine, basiliximab, belotecan, bendamustine, bevacizumab, bexarotene, bicalutamide, bisantrene, bleomycin, bortezomib, bosutinib, brivanib alaninate, buserelin, busulfan, cabazitaxel, CAL-101, calcium folinate, calcium levofolinate, camptothecin, capecitabine, carboplatin, carmofur, carmustine, catumaxomab, cediranib, celmoleukin, cetuximab, chlorambucil, chlormadinone, chlormethine, cidofovir, cisplatin, cladribine, clodronic acid, clofarabine, combretastatin, crisantaspase, crizotinib, cyclophosphamide, cyproterone, cytarabine, dacarbazine, dactinomycin, darbepoetin alfa, darinaparsin, dasatinib, daunorubicin, decitabine, degarelix, denileukin diftitox, denosumab, deslorelin, dibrospidium chloride, docetaxel, dovitinib, doxifluridine, doxorubicin, dutasteride, eculizumab, edrecolomab, eflornithine, elliptinium acetate, eltrombopag, endostatin, enocitabine, epimbicin, epirubicin, epitiostanol, epoetin alfa, epoetin beta, epothilone, eptaplatin, eribulin, erlotinib, estradiol, estramustine, etoposide, everolimus, exatecan, exemestane, exisulind, fadrozole, fenretinide, filgrastim, finasteride, flavopiridol, fludarabine, 5-fluorouracil, fluoxymesterone, flutamide, foretinib, formestane, fotemustine, fulvestrant, ganirelix, gefitinib, gemcitabine, gemtuzumab, gimatecan, gimeracil, glufosfamide, glutoxim, goserelin, histrelin, hydroxyurea, ibandronic acid, ibritumomab tiuxetan, idarubicin, ifosfamide, imatinib, imiquimod, improsulfan, intedanib, interferon alpha, interferon alpha-2a, interferon alpha-2b, interferon beta, interferon gamma, interleukin-2, ipilimumab, irinotecan, ixabepilone, lanreotide, lapatinib, lasofoxifene, lenalidomide, lenograstim, lentinan, lenvatinib, lestaurtinib, letrozole, leuprorelin, levamisole, linifanib, linsitinib, lisuride, lobaplatin, lomustine, lonidamine, lurtotecan, mafosfamide, mapatumumab, masitinib, masoprocol, medroxyprogesterone, megestrol, melarsoprol, melphalan, mepitiostane, mercaptopurine, methotrexate, methyl aminolevulinate, methyltestosterone, mifamurtide, mifepristone, miltefosine, miriplatin, mitobronitol, mitoguazone, mitolactol, mitomycin, mitotane, mitoxantrone, molgramostim, motesanib, nandrolone, nedaplatin, nelarabine, neratinib, nilotinib, nilutamide, nimotuzumab, nimustine, nitracrine, nolatrexed, ofatumumab, oprelvekin, oxaliplatin, paclitaxel, palifermin, pamidronic acid, panitumumab, pazopanib, pegaspargase, peg-epoetin beta, pegfilgastrim, peginterferon alpha-2b, pelitrexol, pemetrexed, pemtumomab, pentostatin, peplomycin, perfosfamide, perifosine, pertuzumab, picibanil, pirambicin, pirarubicin, plerixafor, plicamycin, poliglusam, polyestradiol phosphate, ponatinib, porfimer sodium, pralatrexate, prednimustine, procarbazine, procodazole, PX-866, quinagolide, raloxifene, raltitrexed, ranibizumab, ranimustine, razoxane, regorafenib, risedronic acid, rituximab, romidepsin, romiplostim, rubitecan, saracatinib, sargramostim, satraplatin, selumetinib, sipuleucel-T, sirolimus, sizofuran, sobuzoxane, sorafenib, streptozocin, sunitinib, talaporfin, tamibarotene, tamoxifen, tandutinib, tasonermin, teceleukin, tegafur, telatinib, temoporfin, temozolomide, temsirolimus, teniposide, testolactone, testosterone, tetrofosmin, thalidomide, thiotepa, thymalfasin, tioguanine, tipifarnib, tivozanib, toceranib, tocilizumab, topotecan, toremifene, tositumomab, trabectedin, trastuzumab, treosulfan, tretinoin, triapine, trilostane, trimetrexate, triptorelin, trofosfamide, ubenimex, valrubicin, vandetanib, vapreotide, varlitinib, vatalanib, vemurafenib, vidarabine, vinblastine, vincristine, vindesine, vinflunine, vinorelbine, volociximab, vorinostat, zinostatin, zoledronic acid, and zorubicin.

Generally, the following aims may be pursued with the combination of compounds of the present invention with other anti-cancer agents:

- improved activity in slowing down the growth of a tumor, in reducing its size or even in its complete elimination compared with treatment with a single active compound;
- possibility of employing the chemotherapeutics used in a lower dosage than in monotherapy;
- possibility of a more tolerable therapy with few side effects compared with individual administration;
- possibility of treatment of a broader spectrum of cancer and tumor diseases;
- achievement of a higher rate of response to therapy;
- longer survival time of the patient compared with standard therapy.

Thus, in a further embodiment, the present invention relates to pharmaceutical compositions comprising at least one of the compounds according to the invention and one or more additional therapeutic agents for the treatment and/or prevention of disorders, especially of the aforementioned disorders.

In cancer treatment, the compounds of the present invention may also be employed in conjunction with radiation therapy and/or surgical intervention.

Furthermore, the compounds of formula (I) may be utilized, as such or in compositions, in research and diagnostics, or as analytical reference standards, and the like, which are well known in the art.

When the compounds of the present invention are administered as pharmaceuticals, to humans and other mammals, they can be given per se or as a pharmaceutical composition containing, for example, 0.1% to 99.5% (more preferably, 0.5% to 90%) of active ingredient in combination with one or more pharmaceutically acceptable excipients.

Thus, in another aspect, the present invention relates to pharmaceutical compositions comprising at least one of the compounds according to the invention, conventionally together with one or more inert, non-toxic, pharmaceutically suitable excipients, and to the use thereof for the treatment and/or prevention of disorders, especially of the aforementioned disorders.

The compounds according to the invention can act systemically and/or locally. For this purpose, they can be administered in a suitable way such as, for example, by the oral, parenteral, pulmonary, nasal, lingual, sublingual, buccal, rectal, dermal, transdermal, conjunctival, otic or topical route, or as an implant or stent.

For these application routes, the compounds of the invention can be administered in suitable application forms.

Suitable for oral administration are application forms which function according to the prior art and deliver the compounds according to the invention rapidly and/or in modified fashion, and which contain the compounds according to the invention in crystalline, amorphous and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilisates, capsules (e.g. hard or soft gelatin capsules), sugar-coated tablets, granules, pellets, powders, emulsions, suspensions, aerosols or solutions.

Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Useful parenteral application forms include injection and infusion preparations in the form of solutions, suspensions, emulsions, lyophilisates and sterile powders.

Forms suitable for other application routes include, for example, inhalatory pharmaceutical forms (e.g. powder inhalers, nebulizers), nasal drops, solutions or sprays, tablets or capsules to be administered lingually, sublingually or buccally (e.g. troches, lozenges), suppositories, ear and eye preparations (e.g. drops, ointments), vaginal capsules, aqueous suspensions (lotions, shaking mixtures), lipophilic suspensions, ointments, creams, milks, pastes, foams, dusting powders, transdermal therapeutic systems (e.g. patches), implants and stents.

In a preferred embodiment, the pharmaceutical composition comprising a compound of formula (I) as defined above is provided in a form suitable for oral administration. In another preferred embodiment, the pharmaceutical composition comprising a compound of formula (I) as defined above is provided in a form suitable for intravenous administration.

The compounds according to the invention can be converted into the recited application forms in a manner known per se by mixing with inert, non-toxic, pharmaceutically suitable excipients. These excipients include, inter alia, carriers (e.g. microcrystalline cellulose, lactose, mannitol), solvents (e.g. liquid polyethylene glycols), emulsifiers (e.g. sodium dodecyl sulfate), surfactants (e.g. polyoxysorbitan oleate), dispersants (e.g. polyvinylpyrrolidone), synthetic and natural polymers (e.g. albumin), stabilizers (e.g. antioxidants such as, for example, ascorbic acid), colorants (e.g. inorganic pigments such as, for example, iron oxides), and taste and/or odour masking agents.

A preferred dose of the compound of the present invention is the maximum that a patient can tolerate and not develop serious side effects. Illustratively, the compound of the present invention may be administered parenterally at a dose of about 0.001 mg/kg to about 1 mg/kg, preferably of about 0.01 mg/kg to about 0.5 mg/kg of body weight. On oral administration, an exemplary dose range is about 0.01 to 100 mg/kg, preferably about 0.01 to 20 mg/kg, and more preferably about 0.1 to 10 mg/kg of body weight. Ranges intermediate to the above-recited values are also intended to be part of the invention.

Nevertheless, actual dosage levels and time course of administration of the active ingredients in the pharmaceutical compositions of the invention may be varied so as to obtain an amount of the active ingredient which is effective to achieve the desired therapeutic response for a particular patient, composition and mode of administration, without being toxic to the patient. It may therefore be necessary where appropriate to deviate from the stated amounts, in particular as a function of age, gender, body weight, diet and general health status of the patient, the bioavailability and pharmacodynamic characteristics of the particular compound and its mode and route of administration, the time or interval over which administration takes place, the dose regimen selected, the response of the individual patient to the active ingredient, the specific disease involved, the degree of or the involvement or severity of the disease, the kind of concurrent treatment (i.e., the interaction of the compound of the invention with other co-administered therapeutics), and other relevant circumstances.

Thus, it may be satisfactory in some cases to manage with less than the aforementioned minimum amount, whereas in other cases the stated upper limit must be exceeded. Treatment can be initiated with smaller dosages, which are less than the optimum dose of the compound. Thereafter, the dosage may be increased by small increments until the optimum effect under the circumstances is reached. For convenience, the total daily dosage may be divided and administered in individual portions spread over the day.

The following exemplary embodiments illustrate the invention. The invention is not restricted to the examples.

The percentages in the following tests and examples are, unless stated otherwise, by weight; parts are by weight. Solvent ratios, dilution ratios and concentrations reported for liquid/liquid solutions are each based on volume.

A. EXAMPLES

Abbreviations and Acronyms

Ac acetyl
$Ac_2O$ acetic anhydride
AcOH acetic acid
aq. aqueous (solution)
Boc tert-butoxycarbonyl
br. broad ($^1$H-NMR signal)
cat. catalytic
conc. concentrated
d doublet ($^1$H-NMR signal)
DCI direct chemical ionization (MS)
DCM dichloromethane
DIPEA N,N-diisopropylethylamine
DMF N,N-dimethylformamide
DMSO dimethylsulfoxide
EI electron impact ionization (MS)
eq. equivalent(s)
ESI electro-spray ionization (MS)
Et ethyl
EtOAc ethyl acetate
EtOH ethanol
GC-MS gas chromatography-coupled mass spectroscopy
h hour(s)
Hal halogen
HATU O-(7-azabenzotriazol-1-yl)-N,N,N',N'-tetramethyluronium hexafluorophosphate
$^1$H-NMR proton nuclear magnetic resonance spectroscopy
HPLC high performance liquid chromatography
iPr isopropyl
LC-MS liquid chromatography-coupled mass spectroscopy
Me methyl
MeOH methanol
min minute(s)
MS mass spectroscopy
m/z mass-to-charge ratio (MS)
n-Bu n-butyl
of th. of theory (chemical yield)
Pd/C palladium on charcoal
$PdCl_2$(dppf) [1,1'-bis(diphenylphosphino)ferrocene]dichloropalladium(II)
Ph phenyl
PPA polyphosphoric acid
q quartet ($^1$H-NMR signal)
quant. quantitative (yield)
rac racemic
$R_f$ TLC retention factor
RP reverse phase (HPLC)
rt room temperature
$R_t$ retention time (HPLC)
s singlet ($^1$H-NMR signal)
sat. saturated (solution)
t triplet ($^1$H-NMR signal)

TBME tert-butyl methyl ether

TBTU N-[(1H-benzotriazol-1-yloxy)(dimethylamino)methylene]-N-methylmethanaminium tetrafluoroborate tBu tert-butyl tert tertiary TFA trifluoroacetic acid THF tetrahydrofuran TLC thin layer chromatography LC-MS and GC-MS Methods:

Method 1 (LC-MS):

Instrument: Micromass Quattro Premier with Waters UPLC Acquity; column: Thermo Hypersil GOLD 1.9μ, 50 mm×1 mm; eluent A: 1 L water+0.5 mL 50% aq. formic acid, eluent B: 1 L acetonitrile+0.5 ml 50% aq. formic acid; gradient: 0.0 min 90% A→0.1 min 90% A→1.5 min 10% A→2.2 min 10% A; temperature: 50° C.; flow rate: 0.33 mL/min; UV detection: 210 nm.

Method 2 (LC-MS):

Instrument: Waters Acquity SQD UPLC System; column: Waters Acquity UPLC HSS T3 1.8μ, 50 mm×1 mm; eluent A: 1 L water+0.25 mL 99% formic acid, eluent B: 1 L acetonitrile+0.25 mL 99% formic acid; gradient: 0.0 min 90% A→1.2 min 5% A→2.0 min 5% A; oven: 50° C.; flow rate: 0.40 mL/min; UV detection: 210-400 nm.

Method 3 (LC-MS):

Instrument: Micromass Quattro Micro with HPLC Agilent 1100 Series; column: YMC-Triart C18 3μ, 50 mm×3 mm; eluent A: 1 L water+0.01 mol ammonium carbonate, eluent B: 1 L acetonitrile; gradient: 0.0 min 100% A→2.75 min 5% A→4.5 min 5% A; oven: 40° C.; flow rate: 1.25 mL/min; UV detection: 210 nm.

Method 4 (LC-MS):

Instrument: Waters Acquity SQD UPLC System; column: Waters Acquity UPLC HSS T3 1.8μ, 30 mm×2 mm; eluent A: 1 L water+0.25 mL 99% formic acid, eluent B: 1 L acetonitrile+0.25 mL 99% formic acid; gradient: 0.0 min 90% A→1.2 min 5% A→2.0 min 5% A; oven: 50° C.; flow rate: 0.60 mL/min; UV detection: 208-400 nm.

Method 5 (LC-MS):

Instrument: Micromass Quattro Premier with Waters UPLC Acquity; column: Thermo Hypersil GOLD 1.9μ, 50 mm×1 mm; eluent A: 1 L water+0.5 mL 50% aq. formic acid, eluent B: 1 L acetonitrile+0.5 ml 50% aq. formic acid; gradient: 0.0 min 97% A→0.5 min 97% A→3 2 min 5% A→4.0 min 5% A; temperature: 50° C.; flow rate: 0.3 mL/min; UV detection: 210 nm.

Method 6 (LC-MS):

Instrument MS: Waters ZQ 2000; Instrument HPLC: Agilent 1100, 2-column-switch, autosampler HTC PAL; column: YMC-ODS-AQ 3.0 μm, 50 mm×4.6 mm; eluent A: water+0.1% formic acid, eluent B: acetonitrile+0.1% formic acid; gradient: 0.0 min 100% A→0.2 min 95% A 1.8 min 25% A→1.9 min 10% A→2.0 min 5% A→3.2 min 5% A→3.21 min 100% A→3.35 min 100% A; oven: 40° C.; flow rate: 3.0 mL/min; UV detection: 210 nm.

Method 7 (LC-MS):

Instrument MS: Waters SQD; Instrument HPLC: Waters UPLC; column: Zorbax SB-Aq (Agilent) 1.8 μm, 50 mm×2.1 mm; eluent A: water+0.025% formic acid, eluent B: acetonitrile+0.025% formic acid; gradient: 0.0 min 98% A→0.9 min 25% A→1.0 min 5% A→1.4 min 5% A→1.41 min 98% A→1.5 min 98% A; oven: 40° C.; flow rate: 0.60 mL/min; UV detection: DAD, 210 nm.

Method 8 (GC-MS):

Instrument: Micromass GCT, GC6890; column: Restek RTX-35, 15 m×200 μm×0.33 μm; constant flow with helium: 0.88 mL/min; oven: 70° C.; inlet: 250° C.; gradient: 70° C., 30° C./min→310° C. (maintain for 3 min).

General Work-Up and Purification Methods (See Tables I-V Below):

Method P1:

The precipitated solid was filtered off, washed with a methanol/water mixture and dried in vacuo.

Method P2:

Preparative RP-HPLC (Reprosil C18, gradient acetonitrile/0.2% aq. trifluoroacetic acid).

Method P3:

Preparative RP-HPLC (Reprosil C18, gradient acetonitrile/0.1% aq. formic acid).

Method P4:

1 M hydrochloric acid was added to the collected HPLC-fractions, and the resulting solution was evaporated to dryness.

Method P5:

The precipitated solid was filtered off, and the filtrate was purified by RP-HPLC.

Method P6:

Preparative RP-HPLC (XBridge C18, gradient acetonitrile/water+0.05% aq. ammonia).

Method P7:

Preparative RP-HPLC-MS: Instrument MS: Waters; Instrument HPLC: Waters; column: Waters XBridge C18, 18 mm×50 mm, 5 μm; eluent A: water+0.05% triethylamine, eluent B: acetonitrile or methanol+0.05% triethylamine, gradient elution; flow rate: 40 ml/min; UV detection: DAD, 210-400 nm.

Method P8:

Preparative RP-HPLC-MS: Instrument MS: Waters; Instrument HPLC: Waters; column: Phenomenex Luna 5μ C18(2) 100A, AXIA Tech., 50 mm×21.2 mm; eluent A: water+0.05% formic acid, eluent B: acetonitrile or methanol+0.05% formic acid, gradient elution; flow rate: 40 ml/min; UV detection: DAD, 210-400 nm.

Starting Materials and Intermediates:

Intermediate 1A

2-Methoxy-4-methylaniline

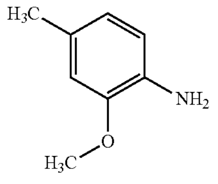

A mixture of 5-methyl-2-nitroanisol (265 g, 1.58 mol) and 10% Pd/C (39.75 g) in THF (1.32 L) was stirred overnight at rt under 1 atm of hydrogen. Filtration over kieselguhr and evaporation afforded 216 g of the crude product which was used in the next step without further purification.

LC-MS (method 3): $R_t$=2.39 min; MS (ESIpos): m/z=138 $(M+H)^+$ $^1$H-NMR (400 MHz, DMSO-$d_6$): δ=6.45-6.63 (m, 3H), 4.46 (s, 2H), 3.72 (s, 3H), 2.16 (s, 3H) ppm.

Intermediate 2A

2-Methoxy-4-methylbenzenethiol

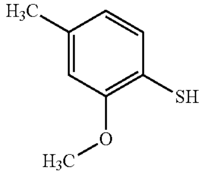

Method 1:

A solution of sodium nitrite (7 g, 101.4 mmol) in water (25 ml) was added dropwise to a cooled (0°-5° C.) solution of Intermediate 1A (13.7 g, 100 mmol) in concentrated hydrochloric acid (30 ml) and water (85 ml). After stirring at 0° C. for 10 min, sodium acetate (15 g, 182.8 mmol) was added. The resulting mixture was added dropwise to a hot solution (70°-80° C.) of potassium O-ethyl dithiocarbonate (30 g, 187.1 mmol) in water (140 ml), stirred between 70° C. and 80° C. for 1 h and then cooled to rt. The mixture was extracted twice with ethyl acetate, and the combined organic extracts were dried over sodium sulfate and evaporated. The residue was taken up in a 1.3 M solution of potassium hydroxide in ethanol (300 ml). Glucose (8 g) was added, and the resulting mixture was refluxed for 3 h. Then, the ethanol solvent was evaporated, and the residue was diluted with water and acidified with 6 N aqueous sulfuric acid. Zinc powder (15 g) was added carefully, and the resulting mixture was heated to 50° C. for 30 min. The mixture was then cooled to rt, diluted with dichloromethane and filtered. The filtrate was extracted twice with dichloromethane, and the combined organic extracts were dried over sodium sulfate and evaporated affording 14.3 g of the crude product which was used in the next step without further purification.

Method 2:

To 2.9 L of THF was added a warm solution of 355 ml (6.67 mol) concentrated sulfuric acid in 1.1 L of water. At 50° C., 293 g (1.33 mol) 2-methoxy-4-methylbenzenesulfonyl chloride were added under stirring. Then, 521 g (7.97 mol) of zinc powder were added carefully in portions (foaming), and the slightly exothermic reaction was cooled in a water bath to maintain a temperature of 50°-55° C. The mixture was subsequently stirred at 55° C. for 3 h. The progress of the reaction was monitored by TLC (silica gel, petrolether/ethyl acetate 95:5). The reaction mixture was poured into 13.6 L of water, 6.8 L dichloromethane were added, and the mixture was stirred for 5 min. After decanting from remaining zinc and phase separation, the aqueous phase was extracted once more with 6.8 L dichloromethane. The combined organic phases were washed with 10% brine, dried and evaporated at 40° C. under reduced pressure yielding 237 g of crude product. This material was used in the next step without further purification. An analytical sample was obtained by silica gel chromatography with petrolether/ethyl acetate (97:3) as eluent.

LC-MS (method 1): $R_t$=1.21 min; MS (ESIneg): m/z=153 $(M-H)^-$ $^1$H-NMR (400 MHz, DMSO-$d_6$): δ=7.17 (d, 1H), 6.81 (s, 1H), 6.66 (d, 1H), 4.63 (br. s, 1H), 3.80 (s, 3H), 2.26 (s, 3H) ppm.

Intermediate 3A

1-[(2,2-Diethoxyethyl)sulfanyl]-2-methoxy-4-methylbenzene

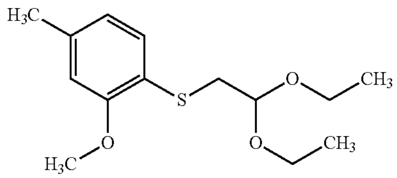 [SMILES: CCOC(CSc1ccc(C)cc1OC)OCC]

237 g crude material from Intermediate 2A, 287 g (1.46 mol) bromoacetaldehyde-diethylacetal and 862 g (2.65 mol) caesium carbonate were suspended in 2 L DMF. The reaction temperature increased initially to 40° C., then stirring was continued overnight at ambient temperature. The reaction mixture was partitioned between 10 L of water and 2.7 L of ethyl acetate. The aqueous phase was extracted with another portion of 2.7 L ethyl acetate. The combined organic phases were washed with 10% brine, dried and evaporated. The resulting oily residue was purified by silica gel chromatography with petrolether/ethyl acetate (95:5) as eluent.

Yield: 236 g of an oil (66% of th.)

GC-MS (method 8): $R_t$=6.03 min; MS (EIpos): m/z=270 $(M)^+$ $^1$H-NMR (400 MHz, DMSO-$d_6$): δ=7.16 (d, 1H), 6.82 (s, 1H), 6.73 (d, 1H), 4.55 (t, 1H), 3.80 (s, 3H), 3.52-3.64 (m, 2H), 3.39-3.51 (m, 2H), 2.96 (d, 2H), 2.33 (s, 3H), 1.09 (t, 6H) ppm.

Intermediate 4A

7-Methoxy-5-methyl-1-benzothiophene

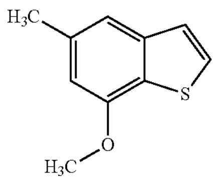

To a refluxing mixture of 13 g polyphosphoric acid and 150 ml chlorobenzene was added dropwise a solution of 5.2 g (19.2 mmol) of Intermediate 3A, and refluxing was continued overnight. After cooling, the organic layer was decanted, and the residue and flask were rinsed twice with DCM. The combined organic phases were evaporated at reduced pressure. The residue (3.76 g) was chromatographed on silica gel with isohexane/0-10% ethyl acetate as eluent.

Yield: 1.69 g of an oil (49% of th.)

GC-MS (method 8): $R_t$=5.20 min; MS (EIpos): m/z=178 $(M)^+$ $^1$H-NMR (400 MHz, DMSO-$d_6$): δ=7.68 (d, 1H), 7.34 (d, 1H), 7.28 (s, 1H), 6.78 (s, 1H), 3.93 (s, 3H), 2.43 (s, 3H) ppm.

Intermediate 5A (7-Methoxy-5-methyl-1-benzothiophen-2-yl)boronic acid

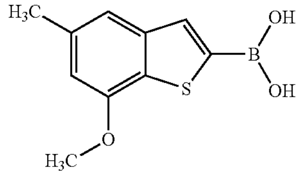

Under argon atmosphere, 26.7 g (150 mmol) of Intermediate 4A were dissolved in 270 ml of THF and cooled to −70° C. Between −70° C. and -65° C., 66 ml (165 mmol) of a 2.5 N solution of n-butyllithium in hexane were added dropwise within 20 min, resulting in formation of a white precipitate. After stirring for 1 h at −70° C., 41.5 ml (180 mmol) triisopropyl borate were added at this temperature within 10 min (resulting in a thick suspension). Stirring was continued for 1 h at −70° C., before the reaction mixture was allowed to warm up to rt overnight. Then, 400 ml of saturated aq. ammonium chloride solution were added, the layers were separated, and the aqueous layer was extracted once more with THF. The combined organic phases were evaporated under reduced pressure. To the residue thus obtained, 200 ml of water and 86 ml of 2 N aq. sodium hydroxide solution were added. The solution was washed twice with DCM, then acidified with 35 ml of 3 M sulfuric acid, and the resulting suspension was stirred vigorously for 1 h. The precipitate was filtered off by suction and dried overnight at 45° C. in vacuo.

Yield: 28.25 g of a colorless solid (94% pure by LC-MS, 80% of th.)

LC-MS (method 2): $R_t$=0.87 min; MS (ESIpos): m/z=223 $(M+H)^+$ $^1$H-NMR (400 MHz, DMSO-$d_6$): δ=7.17 (d, 1H), 6.81 (s, 1H), 6.66 (d, 1H), 4.63 (br. s, 1H), 3.80 (s, 3H), 2.26 (s, 3H) ppm.

Intermediate 6A 2-(7-Methoxy-5-methyl-1-benzothiophen-2-yl)-6-methyl-1,3,6,2-dioxazaborocane-4,8-dione

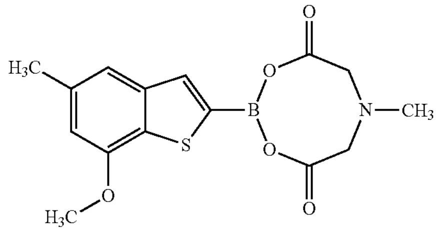

6.3 g (28.4 mmol) of Intermediate 5A and 4.2 g (28.4 mmol) 2,2'-(methylimino)diacetic acid were dissolved in a mixture of 45 ml DMSO and 400 ml toluene and refluxed for 16 h using a Dean-Stark trap. After evaporation, the residue was taken up in ethyl acetate and washed three times with water and once with brine. The organic phase was dried over magnesium sulfate and evaporated to a volume of about 200 ml. A white solid precipitated which was filtered, washed with ethyl acetate and dried in vacuo to give a first crop (5.52 g) of the title compound. A second crop (3.32 g) was obtained after evaporation of the mother liquor and flash-chromatography over a layer of silica gel using cyclohexane/0-100% ethyl acetate as the eluent.

Yield: 8.84 g (overall purity 92.5% by LC-MS, 87% of th.)

LC-MS (method 2): $R_t$=0.93 min; MS (ESIpos): m/z=334 $(M+H)^+$ $^1$H-NMR (400 MHz, DMSO-$d_6$): δ=7.42 (s, 1H), 7.26 (s, 1H), 6.76 (s, 1H), 4.40 (d, 2H), 4.17 (d, 2H), 3.92 (s, 3H), 2.63 (s, 3H), 2.42 (s, 3H) ppm.

Intermediate 7A 2-(5-Chloro-7-methoxy-1-benzothiophen-2-yl)-6-methyl-1,3,6,2-dioxazaborocane-4,8-dione

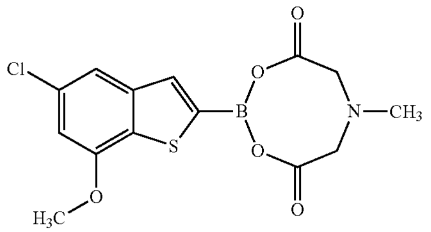 [SMILES: COc1cc(Cl)cc2cc(B3OC(=O)CN(C)CC(=O)O3)sc12]

The title compound was prepared from 4-chloro-2-methoxybenzenethiol [J. O. Jilek et al., *Collection of Czechoslovak Chemical Communications*, Vol. 43, 1978, p. 1747-1759] following the procedures described for Intermediates 3A, 4A, 5A and 6A.

LC-MS (method 2): $R_t$=0.96 min; MS (ESIpos): m/z=354 $(M+H)^+$ $^1$H-NMR (400 MHz, DMSO-$d_6$): δ=7.58 (d, 1H), 7.51 (s, 1H), 6.98 (d, 1H), 4.42 (d, 2H), 4.19 (d, 2H), 3.97 (s, 3H), 2.65 (s, 3H) ppm.

Intermediate 8A

4-Aminopyrrolo[2,1-f][1,2,4]triazine-7-carbaldehyde

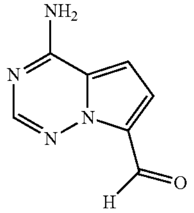 [SMILES: Nc1ncnn2c(C=O)ccc12]

Phosphoryl chloride (104 ml) was added dropwise at 0° C. to a solution of pyrrolo[2,1-f][1,2,4]-triazin-4-amine (30 g, 24.5 mmol; preparation described in Int. Pat. Appl. WO 2007/064931, Intermediate A) in DMF (500 ml). The resulting mixture was stirred at 60° C. for 25 h, then poured onto an ice-water mixture and stirred at rt for further 16 h. The mixture was adjusted to pH 8-10 by addition of 3.5 M aq. sodium hydroxide solution. The precipitated solid was filtered off and washed with water affording 28.8 g (73% of th.) of the title compound.

LC-MS (method 2): $R_t$=0.32 min; MS (ESIpos): m/z=163 $(M+H)^+$ $^1$H-NMR (400 MHz, DMSO-$d_6$): δ=10.26 (s, 1H), 8.26 (br. s, 1H), 8.21 (br. s, 1H), 8.09 (s, 1H), 7.27 (d, 1H), 7.02 (d, 1H) ppm.

Intermediate 9A

4-Amino-5-bromopyrrolo[2,1-f][1,2,4]triazine-7-carbaldehyde

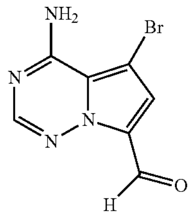 [SMILES: Nc1ncnn2c(C=O)cc(Br)c12]

A suspension of Intermediate 8A (28.16 g, 174 mmol) in THF (800 ml) was treated with 1,3-dibromo-5,5-dimethylhydantoin (29.8 g, 104 mmol) and stirred at rt for 7 h. The resulting solid was filtered off and washed with methanol affording 32.61 g (74% of th.) of the title compound.

LC-MS (method 5): $R_t$=1.40 min; MS (ESIpos): m/z=240/242 $(M+H)^+$ $^1$H-NMR (400 MHz, DMSO-$d_6$): δ=10.22 (s, 1H), 8.59 (br. s, 1H), 8.12 (s, 1H), 7.42 (s, 1H), 7.17 (br. s, 1H) ppm.

Intermediate 10A

4-Amino-5-(7-methoxy-5-methyl-1-benzothiophen-2-yl)pyrrolo[2,1-f][1,2,4]triazine-7-carbaldehyde

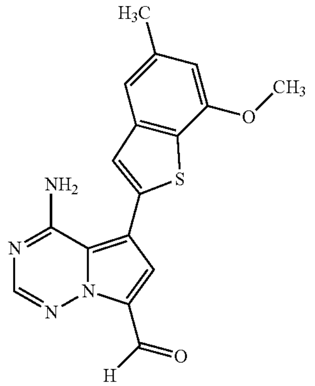 [SMILES: COc1cc(C)cc2cc(-c3cc(C=O)n4ncnc(N)c34)sc12]

Under argon, a suspension of Intermediate 9A (5.00 g, 20.7 mmol), Intermediate 5A (8.29 g, 24.9 mmol) and caesium fluoride (15.7 g, 103.7 mmol) in THF/water (10:1, 250 ml) was degassed, and 4-(di-tert-butylphosphino)-N,N-dimethylaniline-dichloropalladium (2:1; 441 mg, 0.622 mmol) was added. The mixture was degassed again and stirred at 50° C. for 16 h. The resulting solid was filtered off and washed with water/methanol (1:1) affording 5.00 g (71% of th.) of the title compound.

LC-MS (method 2): $R_t$=1.07 min; MS (ESIpos): m/z=339 $(M+H)^+$ $^1$H-NMR (400 MHz, DMSO-$d_6$): δ=10.35 (s, 1H), 8.46 (br. s, 1H), 8.21 (s, 1H), 7.43 (s, 1H), 7.38 (s, 1H), 7.30 (s, 1H), 6.85 (s, 1H), 6.53 (br. s, 1H), 3.96 (s, 3H), 2.45 (s, 3H) ppm.

Intermediate 11A

[4-Amino-5-(7-methoxy-5-methyl-1-benzothiophen-2-yl)pyrrolo[2,1-f][1,2,4]triazin-7-yl]methanol

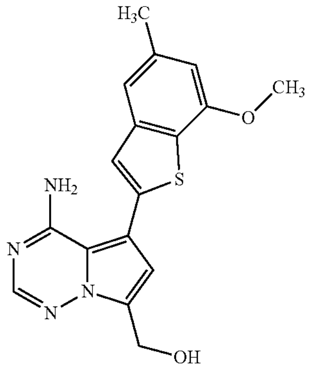 [SMILES: COc1cc(C)cc2cc(-c3cc(CO)n4ncnc(N)c34)sc12]

A suspension of Intermediate 10A (500 mg, 1.48 mmol) in ethanol (20 ml) was treated with sodium borohydride (391 mg, 10.34 mmol). The mixture was stirred at rt for 20 h, then quenched with water and acidified with 1 M hydrochloric acid. After stirring for 20 min, the mixture was filtered, water and ethyl acetate were added, and the phases were separated. The aqueous phase was saturated with sodium chloride and extracted three times with ethyl acetate. The combined organic phases were dried over magnesium sulfate, filtered and evaporated affording 316 mg (63% of th.) of the title compound.

LC-MS (method 2): $R_t$=0.91 min; MS (ESIpos): m/z=341 $(M+H)^+$ $^1$H-NMR (400 MHz, DMSO-$d_6$): δ=7.97 (s, 1H), 7.33 (s, 1H), 7.29 (s, 1H), 6.82 (s, 1H), 6.78 (s, 1H), 5.26 (t, 1H), 4.76 (d, 2H), 3.95 (s, 3H), 2.44 (s, 3H) ppm.

Intermediate 12A 7-(Chloromethyl)-5-(7-methoxy-5-methyl-1-benzothiophen-2-yl)pyrrolo[2,1-f][1,2,4]triazin-4-amine hydrochloride

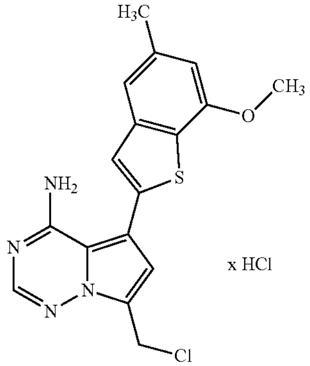 [SMILES: COc1cc(C)cc2cc(-c3cc(CCl)n4ncnc(N)c34)sc12]

A solution of Intermediate 11A (3.77 g, 11.07 mmol) in toluene (150 ml) was treated with thionyl chloride (8.1 ml, 110.7 mmol). The mixture was stirred at rt for 20 h and then evaporated. The residue was repeatedly (three times) co-evaporated with toluene leaving 4.30 g of the crude product which was used in the next step without further purification.

$^1$H-NMR (400 MHz, DMSO-$d_6$): δ=8.19 (s, 1H), 7.40 (s, 1H), 7.30 (s, 1H), 7.06 (s, 1H), 6.84 (s, 1H), 5.10 (s, 2H), 3.96 (s, 3H), 2.45 (s, 3H) ppm.

Intermediate 13A

7-[(E/Z)-(Hydroxyimino)methyl]-5-(7-methoxy-5-methyl-1-benzothiophen-2-yl)pyrrolo[2,1-f]-[1,2,4]triazin-4-amine

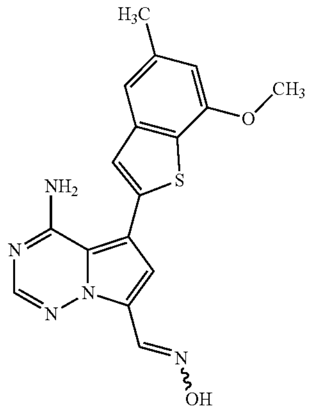 [SMILES: COc1cc(C)cc2cc(-c3cc(C=NO)n4ncnc(N)c34)sc12]

A solution of Intermediate 10A (250 mg, 0.74 mmol), hydroxylamine hydrochloride (78 mg, 1.12 mmol) and sodium acetate (182 mg, 2.22 mmol) in an ethanol/water mixture (3:1, 3 ml) was stirred at rt overnight. Further portions of hydroxylamine hydrochloride (50 mg, 0.72 mmol) and sodium acetate (90 mg, 1.10 mmol) were added, and stirring was continued for another night. Then, the major part of the ethanol solvent was evaporated under reduced pressure, water was added, and the precipitate was filtered off. The solid was dried in vacuo at 45° C. yielding 237 mg (89% of th.) of the title compound.

LC-MS (method 4): $R_t$=0.97 min; MS (ESIpos): m/z=354 $(M+H)^+$ $^1$H-NMR (400 MHz, DMSO-$d_6$): δ=11.93 (s, 0.3H), 11.49 (s, 0.7H), 8.50 (s, 0.8H), 7.91-8.17 (m, 1.4H), 7.59 (s, 0.4H), 7.39 (s, 1H), 7.30 (s, 1H), 7.06 (s, 0.8H), 6.83 (s, 1H), 3.96 (s, 3H), 2.44 (s, 3H) ppm [E/Z-mixture of isomers].

Intermediate 14A 7-(Aminomethyl)-5-(7-methoxy-5-methyl-1-benzothiophen-2-yl)pyrrolo[2,1-f][1,2,4]triazin-4-amine

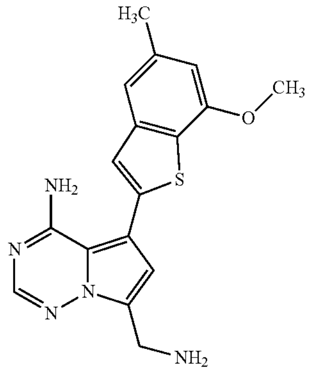 [SMILES: COc1cc(C)cc2cc(-c3cc(CN)n4ncnc(N)c34)sc12]

Zinc powder (390 mg, 6 mmol) was added to a solution of Intermediate 13A (78 mg, 0.22 mmol) in methanol (30 ml). Then, a mixture of 0.3 ml conc. hydrochloric acid and 2 ml methanol was added dropwise at rt under stirring, followed by another portion of 0.5 ml conc. hydrochloric acid in 2 ml methanol until a pH of 0-1 was reached. The mixture was subsequently stirred at rt for 1 h. After this, the precipitate was filtered off and discarded. The filtrate was concentrated in vacuo to a small volume and purified by preparative RP-HPLC (Reprosil C18, gradient 5-95% acetonitrile/0.1% aq. formic acid) to yield 20.5 mg (23% of th.) of the title compound.

LC-MS (method 2): $R_t$=0.72 min; MS (ESIneg): m/z=338 $(M-H)^-$ $^1$H-NMR (400 MHz, DMSO-$d_6$): δ=8.26 (br. s, 1H), 8.00 (s, 1H), 7.32 (s, 1H), 7.29 (s, 1H), 6.84 (s, 1H), 6.82 (s, 1H), 4.11 (br. s, 2H), 3.95 (s, 3H), 2.44 (s, 3H) ppm.

Intermediate 15A

4-Amino-5-(7-methoxy-5-methyl-1-benzothiophen-2-yl)pyrrolo[2,1-f][1,2,4]triazine-7-carboxylic acid

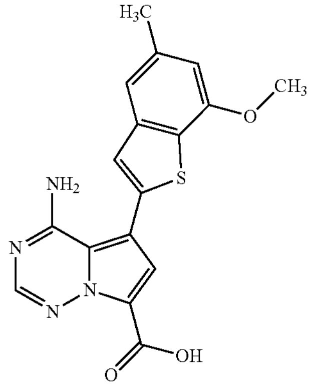 [SMILES: COc1cc(C)cc2cc(-c3cc(C(=O)O)n4ncnc(N)c34)sc12]

A solution of Intermediate 10A (4.1 g, 7.27 mmol) in THF/water (10:1, 216.5 ml) was treated with a 2 M solution of 2-methyl-2-butene in THF (18.2 ml, 36.3 mmol) and with sodium dihydrogenphosphate (4.01 g, 29.08 mmol). After stirring at rt for 5 min, sodium chlorite (2.63 g, 29.08 mmol) was added, and the resulting mixture was stirred at rt overnight. After dilution with water, the aqueous phase was extracted three times with ethyl acetate. The combined organic phases were extracted with 1 M aq. sodium hydroxide solution and then discarded. The aqueous phase was adjusted to pH 3 with 1 M hydrochloric acid and extracted several times with ethyl acetate. The combined organic layers were washed with sat. aq. iron(II) sulfate solution, dried over magnesium sulfate and evaporated. Purification of the residue by preparative RP-HPLC (Sunfire C18, 70% methanol/30% 0.2% aq. TFA) afforded 1.58 g (58% of th.) of the title compound.

LC-MS (method 5): $R_t$=2.11 min; MS (ESIpos): m/z=355 $(M+H)^+$ $^1$H-NMR (400 MHz, DMSO-$d_6$): δ=12.94 (br. s, 1H), 8.58-7.88 (m, 3H), 7.41 (s, 1H), 7.33 (s, 1H), 7.30 (s, 1H), 6.84 (s, 1H), 3.96 (s, 3H), 2.44 (s, 3H) ppm.

Intermediate 16A tert-Butyl 4-{[4-amino-5-(7-methoxy-5-methyl-1-benzothiophen-2-yl)pyrrolo[2,1-f][1,2,4]triazin-7-yl]methyl}piperazine-1-carboxylate

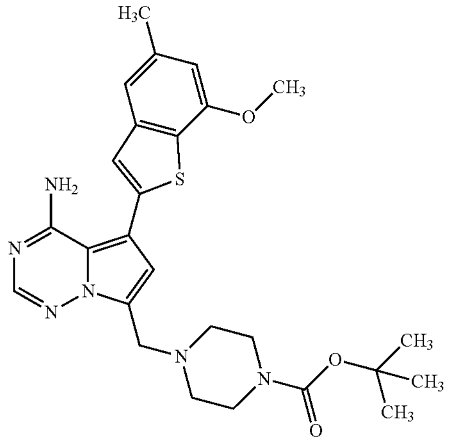 [SMILES: COc1cc(C)cc2cc(-c3cc(CN4CCN(C(=O)OC(C)(C)C)CC4)n4ncnc(N)c34)sc12]

A solution of tert-butyl 4-[(4-amino-5-bromopyrrolo[2,1-f][1,2,4]triazin-7-yl)methyl]piperazine-1-carboxylate (8 g, 19.45 mmol; preparation described in Int. Pat. Appl. WO 2007/064931, Intermediate I/Step 2) in THF (250 ml) was degassed under argon. Intermediate 6A (8.42 g, 25.29 mmol) and a solution of caesium fluoride (14.77 g, 97.2 mmol) in water (25 ml) were added, and the mixture was degassed again. Then, 4-(di-tert-butylphosphino)-N,N-dimethylaniline-dichloropalladium (2:1; 0.41 g, 0.58 mmol) was added, and the mixture was stirred under argon at 50° C. for 16h. The resulting solution was washed with brine, dried over magnesium sulfate, filtered and concentrated to a volume of about 50 ml. TBME (100 ml) was added, and the resulting precipitate was filtered off, washed with TBME and dried in vacuo affording 8.2 g (80% of th.) of the title compound.

LC-MS (method 2): $R_t$=0.91 min; MS (ESIpos): m/z=509 $(M+H)^+$ $^1$H-NMR (400 MHz, DMSO-$d_6$): δ=7.97 (s, 1H), 7.22 (m, 2H), 6.76 (s, 1H), 6.65 (s, 1H), 5.75 (br. s, 2H), 3.93-4.06 (m, 5H), 3.38-3.55 (m, 4H), 2.57-2.52 (m, 4H), 2.49 (s, 3H), 1.45 (s, 9H) ppm.

Intermediate 17A tert-Butyl 4-{[4-amino-5-(7-methoxy-1-benzothiophen-2-yl)pyrrolo[2,1-f][1,2,4]triazin-7-yl]-methyl}piperazine-1-carboxylate

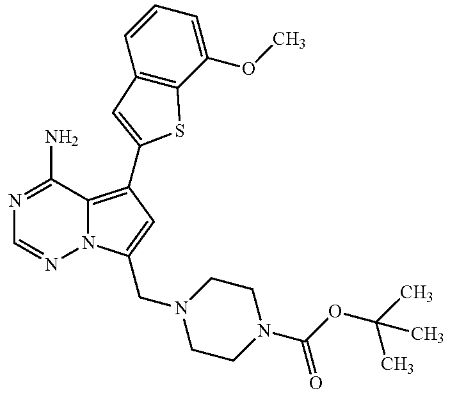 [SMILES: COc1cccc2cc(-c3cc(CN4CCN(C(=O)OC(C)(C)C)CC4)n4ncnc(N)c34)sc12]

A mixture of tert-butyl 4-[(4-amino-5-bromopyrrolo[2,1-f][1,2,4]triazin-7-yl)methyl]piperazine-1-carboxylate (500 mg, 0.97 mmol; preparation described in Int. Pat. Appl. WO 2007/064931, Intermediate I/Step 2), (7-methoxy-1-benzothiophen-2-yl)boronic acid (202 mg, 0.97 mmol; preparation described in U.S. Pat. No. 6,025,382), sodium hydrogencarbonate (327 mg, 3.89 mmol) and [1,1'-bis(diphenylphosphino)ferrocene]dichloropalladium(II)-dichloromethane complex [$PdCl_2$(dppf)×DCM] (40 mg, 0.05 mmol) in degassed 1,2-dimethoxyethane/water (3:1, 4 ml) was stirred under argon at 80° C. overnight. After this, ethyl acetate was added, and the mixture was washed with sat. aq. sodium carbonate solution. The organic phase was dried and evaporated under reduced pressure. The residue was purified by silica gel chromatography (ethyl acetate/cyclohexane 1:2) followed by preparative RP-HPLC (Reprosil C18, gradient methanol/0.2% aq. formic acid) to yield 68 mg (14% of th.) of the title compound.

LC-MS (method 2): $R_t$=0.89 min; MS (ESIpos): m/z=495 $(M+H)^+$ $^1$H-NMR (400 MHz, DMSO-$d_6$): δ=7.98 (s, 1H), 7.48 (d, 1H), 7.43 (s, 1H), 7.37 (t, 1H), 6.97 (d, 1H), 6.79 (s, 1H), 3.97 (s, 3H), 3.87 (s, 2H), 3.30 (s, 4H), 2.42 (br. t, 4H), 1.38 (s, 9H) ppm.

Intermediate 18A tert-Butyl [(3S)-1-{[4-amino-5-(7-methoxy-5-methyl-1-benzothiophen-2-yl)pyrrolo[2,1-f][1,2,4]-triazin-7-yl]methyl}-3-methylpyrrolidin-3-yl]carbamate

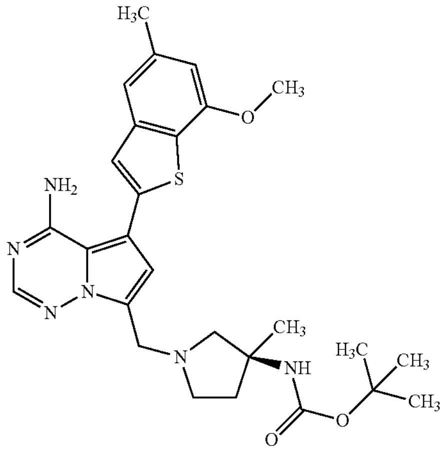 [SMILES: COc1cc(C)cc2cc(-c3cc(CN4CC[C@](C)(NC(=O)OC(C)(C)C)C4)n4ncnc(N)c34)sc12]

A solution of Intermediate 10A (250 mg, 0.68 mmol) in 8 ml methanol was treated with 78 µl (1.36 mmol) acetic acid, 204 mg (1.02 mmol) tert-butyl [(3S)-3-methylpyrrolidin-3-yl]carbamate [Yoshida et al., *Chem. Pharm. Bull.* 1996, 44 (7), 1376-1386] and 214 mg (3.40 mmol) sodium cyanoborohydride. The resulting mixture was stirred at 60° C. for 26 h. After this, the mixture was filtered, and the filtrate was purified by preparative RP-HPLC (Reprosil C18, gradient acetonitrile/0.2% aq. formic acid) to yield 140 mg (36% of th.) of the title compound.

LC-MS (method 2): $R_t$=0.90 min; MS (ESIpos): m/z=523 $(M+H)^+$.

Intermediate 19A tert-Butyl [(3S)-1-{[4-amino-5-(7-methoxy-5-methyl-1-benzothiophen-2-yl)pyrrolo[2,1-f][1,2,4]-triazin-7-yl]carbonyl}-3-methylpyrrolidin-3-yl]carbamate

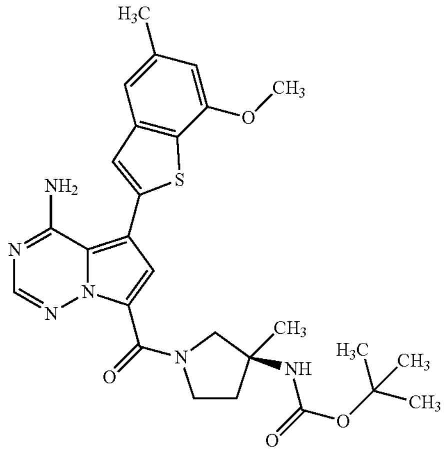 [SMILES: COc1cc(C)cc2cc(-c3cc(C(=O)N4CC[C@](C)(NC(=O)OC(C)(C)C)C4)n4ncnc(N)c34)sc12]

A solution of Intermediate 15A (100 mg, 89% purity, 0.25 mmol) in 1.8 ml DMF was treated with 89 mg (0.28 mmol) TBTU and 81 mg (129 mmol) DIPEA. After stirring at rt for 15 min, 55 mg (0.28 mmol) tert-butyl [(3S)-3-methylpyrrolidin-3-yl]carbamate [Yoshida et al., *Chem. Pharm. Bull.* 1996, 44 (7), 1376-1386] were added, and stirring was continued at rt for 16 h. After this, the reaction mixture was directly purified by preparative RP-HPLC (Reprosil C18, gradient acetonitrile/0.2% aq. formic acid). The product containing fractions were adjusted to pH 8 with sodium hydrogencarbonate and extracted with ethyl acetate. The organic layer was washed with brine, dried over magnesium sulfate, filtered and evaporated to yield 109 mg (81% of th.) of the title compound.

LC-MS (method 2): $R_t$=1.10 min; MS (ESIpos): m/z=537 $(M+H)^+$.

Intermediate 20A tert-Butyl [2-({[4-amino-5-(7-methoxy-5-methyl-1-benzothiophen-2-yl)pyrrolo[2,1-f][1,2,4]triazin-7-yl]methyl}amino)-2-oxoethyl] carbamate

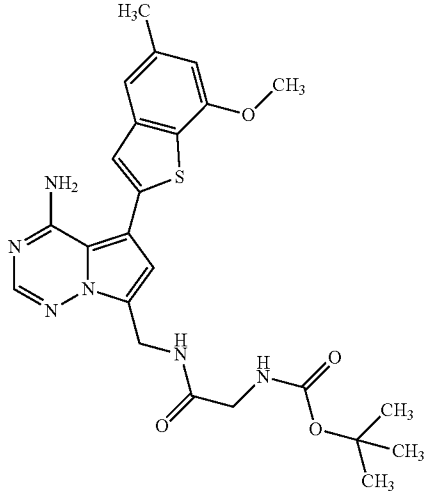 [SMILES: COc1cc(C)cc2cc(-c3cc(CNC(=O)CNC(=O)OC(C)(C)C)n4ncnc(N)c34)sc12]

A solution of Intermediate 14A (15 mg, 36 μmol) in methanol (0.5 ml) was treated with N-(tertbutoxycarbonyl) glycine (8 mg, 44 μmol), HATU (18 mg, 47 μmol) and DIPEA (13 μl, 73 μmol). The resulting mixture was stirred at rt overnight. After concentration under reduced pressure, the residue was purified by preparative RP-HPLC (Reprosil C18, gradient 10-95% acetonitrile/0.1% aq. formic acid) yielding 7.1 mg (39% of th.) of the title compound.

LC-MS (method 5): $R_t$=2.19 min; MS (ESIpos): m/z=497 $(M+H)^+$ $^1$H-NMR (400 MHz, DMSO-$d_6$): δ=8.29 (t, 1H), 7.99 (s, 1H), 7.31 (s, 1H), 7.28 (s, 1H), 7.00 (t, 1H), 6.81 (s, 1H), 6.74 (s, 1H), 4.48-4.67 (m, 2H), 3.95 (s, 3H), 3.57 (d, 2H), 2.44 (s, 3H), 1.37 (s, 9H) ppm.

PREPARATION EXAMPLES

Example 1

5-(7-Methoxy-5-methyl-1-benzothiophen-2-yl)-7-(piperazin-1-ylmethyl)pyrrolo[2,1-f][1,2,4]-triazin-4-amine trihydrochloride hydrate

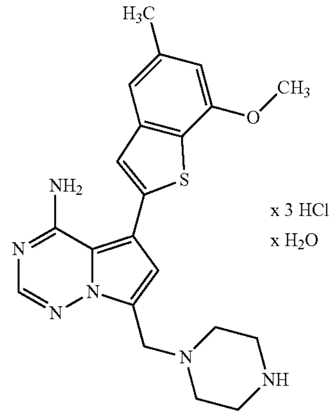 [SMILES: COc1cc(C)cc2cc(-c3cc(CN4CCNCC4)n4ncnc(N)c34)sc12]

x 3 HCl x $H_2O$

Intermediate 16A (2 g, 3.93 mmol) was stirred in a 4 M solution of hydrogen chloride in 1,4-dioxane (60 ml) at rt for 3 days. The precipitate was filtered off, washed three times with TBME and dried in vacuo. This material (2.0 g) was suspended in TBME (80 ml) and stirred under reflux for 15 min. The solid was filtered off again, washed three times with TBME and dried in vacuo at 45° C. yielding 1.95 g (92% of th.) of the title compound.

LC-MS (method 2): $R_t$=0.69 min; MS (ESIpos): m/z=409 $(M+H)^+$ $^1$H-NMR (400 MHz, DMSO-$d_6$): inter alia δ=9.84 (br. s, 2H), 8.71-9.04 (m, 1H), 8.26 (s, 1H), 7.40 (s, 1H), 7.33 (s, 1H), 7.27 (s, 1H), 6.85 (s, 1H), 4.75 (br. s, 2H), 3.96 (s, 3H), 3.43 (br. m, 8H), 2.45 (s, 3H) ppm.

Elemental analysis for $C_{21}H_{24}N_6OS \times 3HCl \times H_2O$:

calculated: C, 47.1; H, 5.5; N, 15.7; Cl, 119.9.

found: C, 46.9; H, 5.4; N, 15.6; Cl 20.1.

Example 2

5-(7-Methoxy-5-methyl-1-benzothiophen-2-yl)-7-(piperazin-1-ylmethyl)pyrrolo[2,1-f][1,2,4]-triazin-4-amine

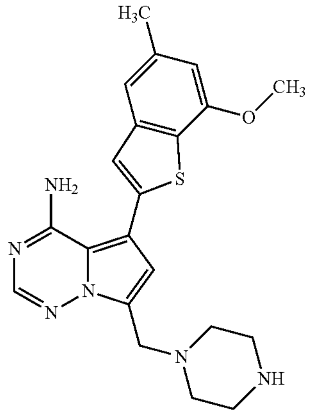 [SMILES: COc1cc(C)cc2cc(-c3cc(CN4CCNCC4)n4ncnc(N)c34)sc12]

A solution of Example 1 (200 mg, 0.373 mmol) in 10 ml water and 5 ml ethanol was treated with sodium bicarbonate (104 mg, 1.24 mmol). After stirring for three days, the formed precipitate was filtered off, washed twice with water/ethanol (2:1) and dried in vacuo at 45° C. yielding 63 mg (41% of th.) of the title compound.

LC-MS (method 2): $R_t$=0.69 min; MS (ESIpos): m/z=409 $(M+H)^+$ $^1$H-NMR (400 MHz, DMSO-$d_6$): δ=7.97 (s, 1H), 7.34 (s, 1H), 7.28 (s, 1H), 6.81 (s, 1H), 6.74 (s, 1H), 3.95 (s, 3H), 3.80 (s, 2H), 2.66 (br. s, 4H), 2.44 (s, 3H), 2.29-2.41 (m, 4H) ppm.

Example 3

5-(7-Methoxy-1-benzothiophen-2-yl)-7-(piperazin-1-ylmethyl)pyrrolo[2,1-f][1,2,4]triazin-4-amine

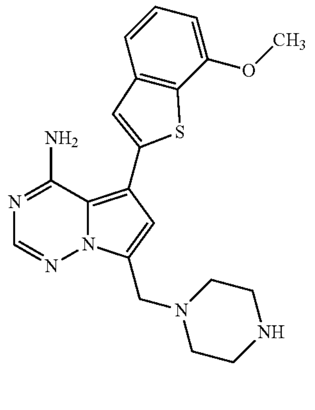 [SMILES: COc1cccc2cc(-c3cc(CN4CCNCC4)n4ncnc(N)c34)sc12]

Intermediate 17A (56 mg, 0.11 mmol) was stirred in a 4 M solution of hydrogen chloride in 1,4-dioxane (2 ml) at rt overnight. The mixture was then evaporated to dryness, and the residue was suspended in ethyl acetate and washed with 1 M aq. sodium hydroxide solution. The organic layer was dried and evaporated. The residue was re-crystallized from DCM/TBME yielding 42 mg (94% of th.) of the title compound.

LC-MS (method 2): $R_t$=0.69 min; MS (ESIpos): m/z=395 $(M+H)^+$ $^1$H-NMR (400 MHz, DMSO-$d_6$): δ=7.97 (s, 1H), 7.48 (d, 1H), 7.43 (s, 1H), 7.37 (t, 1H), 6.97 (d, 1H), 6.76 (s, 1H), 3.97 (s, 3H), 3.82 (s, 2H), 2.65-2.75 (m, 4H), 2.38-2.45 (m, 4H) ppm.

Example 4

5-(5-Chloro-7-methoxy-1-benzothiophen-2-yl)-7-(piperazin-1-ylmethyl)pyrrolo[2,1-f][1,2,4]-triazin-4-amine trihydrochloride

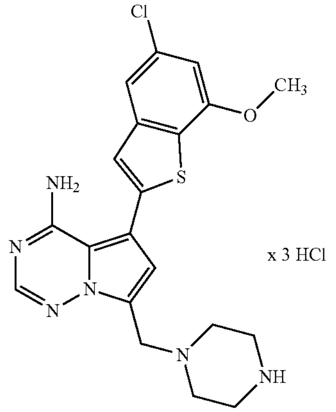 [SMILES: COc1cc(Cl)cc2cc(-c3cc(CN4CCNCC4)n4ncnc(N)c34)sc12]

A solution of tert-butyl 4-[(4-amino-5-bromopyrrolo[2,1-f][1,2,4]triazin-7-yl)methyl]piperazine-1-carboxylate (48.5 mg, 118 μmol; preparation described in hit. Pat. Appl. WO 2007/064931, Intermediate I/Step 2), Intermediate 7A (50 mg, 141 μmol) and caesium fluoride (90 mg, 589 μmol) in THF/water (10:1, 2.2 ml) was degassed under argon, and 4-(di-tert-butylphosphino)-N,N-dimethylaniline-dichloropalladium (2:1; 2.5 mg, 4 μmol) was added. The mixture was degassed again and stirred under argon at 50° C. overnight. After this, the organic layer was separated, diluted with acetonitrile and purified by preparative RP-HPLC (Reprosil C18, gradient acetonitrile/0.2% aq. formic acid). The fractions containing the Boc-protected intermediate compound tert-butyl 4-{[4-amino-5-(5-chloro-7-methoxy-1-benzothiophen-2-yl)pyrrolo[2,1-f][1,2,4]triazin-7-yl]methyl}-piperazine-1-carboxylate were combined, treated with 1 M hydrochloric acid (1 ml) and then evaporated to dryness yielding 39 mg (61% of th.) of the title compound.

LC-MS (method 4): $R_t$=0.68 min; MS (ESIpos): m/z=429 $(M+H)^+$ $^1$H-NMR (400 MHz, DMSO-$d_6$): δ=9.41 (br. s, 2H), 8.15 (s, 1H), 7.61 (s, 1H), 7.43 (s, 1H), 7.19 (s, 1H), 7.06 (s, 1H), 4.69 (br. s, 2H), 4.01 (s, 3H), 3.39 (br. s, 8H) ppm.

Example 5

7-{[(3S)-3-Amino-3-methylpyrrolidin-1-yl]methyl}-5-(7-methoxy-5-methyl-1-benzothiophen-2-yl)pyrrolo[2,1-f][1,2,4]triazin-4-amine trihydrochloride

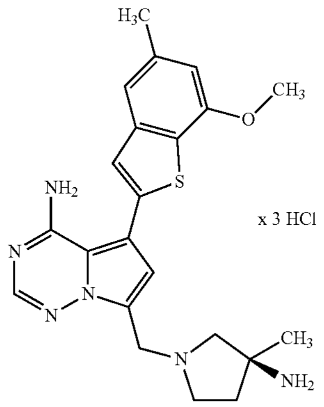 [SMILES: COc1cc(C)cc2cc(-c3cc(CN4CC[C@](C)(N)C4)n4ncnc(N)c34)sc12]

A solution of Intermediate 18A (140 mg, 0.25 mmol) in 1,4-dioxane (2.5 ml) was treated with a 4 M solution of hydrogen chloride in 1,4-dioxane (60 ml) at rt for 3 days. After this, the reaction mixture was evaporated to dryness, and the residue was purified by preparative RP-HPLC (Reprosil C18, gradient acetonitrile/0.2% aq. formic acid). The product fractions were combined, diluted with 1 M hydrochloric acid and then evaporated yielding 107 mg (82% of th.) of the title compound.

LC-MS (method 2): $R_t$=0.67 min; MS (ESIpos): m/z=423 $(M+H)^+$ $^1$H-NMR (400 MHz, methanol-$d_4$): δ=8.23 (s, 1H), 7.47 (s, 1H), 7.36 (s, 1H), 7.32 (s, 1H), 6.82 (s, 1H), 4.99 (s, 2H), 4.00 (s, 3H), 3.54-3.96 (m, 5H), 2.31-2.58 (m, 5H), 1.65 (s, 3H) ppm.

Example 6

(3R)-3-({[4-Amino-5-(7-methoxy-5-methyl-1-benzothiophen-2-yl)pyrrolo[2,1-f][1,2,4]triazin-7-yl]methyl}amino)pyrrolidin-2-one dihydrochloride

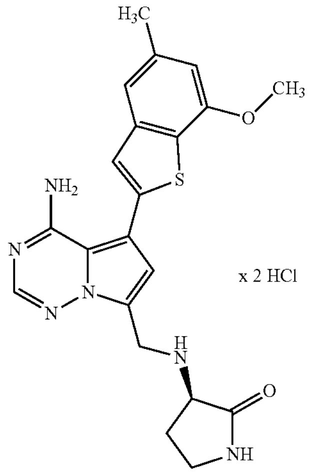 [SMILES: COc1cc(C)cc2cc(-c3cc(CN[C@@H]4CCNC4=O)n4ncnc(N)c34)sc12]

To a suspension of Intermediate 10A (200 mg, 591 μmol) in methanol (5 ml) was added acetic acid (68 μl, 1.18 mmol), (R)-3-aminopyrrolidin-2-one (89 mg, 887 μmol) and sodium cyanoborohydride (185 mg, 2.96 mmol). The mixture was stirred at 60° C. for 20 h and then directly purified by preparative RP-HPLC (Reprosil C18, gradient acetonitrile/0.2% aq. TFA). The product fractions were combined, diluted with 1 M hydrochloric acid and then evaporated yielding 228 mg (78% of th.) of the title compound.

LC-MS (method 2): $R_t$=0.73 min; MS (ESIpos): m/z=423 $(M+H)^+$ $^1$H-NMR (400 MHz, DMSO-$d_6$): inter alia δ=9.93-10.06 (br. s, 1H), 9.70-9.83 (br. s, 1H), 8.40-8.80 (br. s, 1H), 8.43 (s, 1H), 8.20 (s, 1H), 7.39 (s, 1H), 7.32 (s, 1H), 7.17 (s, 1H), 6.85 (s, 1H), 6.56-7.24 (br. s, 1H), 4.79 (d, 1H), 4.60 (d, 1H), 4.00-4.10 (m, 1H), 3.96 (s, 3H), 3.17-3.34 (m, 2H), 2.45 (s, 3H), 2.09-2.22 (m, 1H) ppm.

Example 7 rac-4-{[4-Amino-5-(7-methoxy-5-methyl-1-benzothiophen-2-yl)pyrrolo[2,1-f][1,2,4]triazin-7-yl]methyl}piperazine-2-carboxamide trihydrochloride

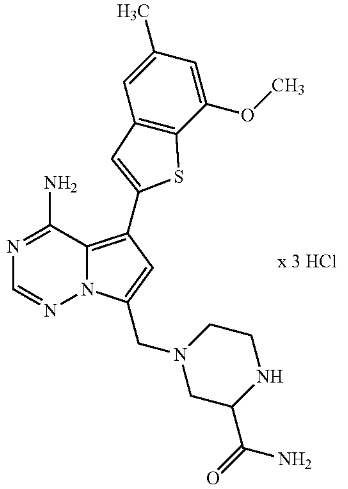 [SMILES: COc1cc(C)cc2cc(-c3cc(CN4CCNC(C(N)=O)C4)n4ncnc(N)c34)sc12]

To a suspension of Intermediate 10A (100 mg, 296 μmol) in methanol (4 ml) was added acetic acid (34 μl, 591 μmol), rac-piperazine-2-carboxamide (57 mg, 443 μmol) and sodium cyanoborohydride (93 mg, 1.48 mmol). The mixture was stirred at 60° C. for 20 h, then filtered and evaporated. The residue was purified by preparative RP-HPLC (Reprosil C18, gradient acetonitrile/0.2% aq. TFA). The product fractions were combined, diluted with 1 M hydrochloric acid and then evaporated yielding 55 mg (32% of th.) of the title compound.

LC-MS (method 2): $R_t$=0.75 min; MS (ESIpos): m/z=452 $(M+H)^+$ $^1$H-NMR (400 MHz, DMSO-$d_6$): inter alia δ=9.49 (br. s, 1H), 8.89 (br. s, 1H), 8.05-8.19 (m, 2H), 7.75 (br. s, 1H), 7.38 (s, 1H), 7.31 (s, 1H), 7.02 (br. s, 1H), 6.84 (s, 1H), 4.12-4.36 (m, 2H), 3.88-4.09 (m, 5H), 3.30 (m, 1H), 3.17 (br. s, 2H), 2.45 (s, 3H) ppm.

Example 8

4-{[4-Amino-5-(7-methoxy-5-methyl-1-benzothiophen-2-yl)pyrrolo[2,1-f][1,2,4]triazin-7-yl]-methyl}piperazin-2-one dihydrochloride

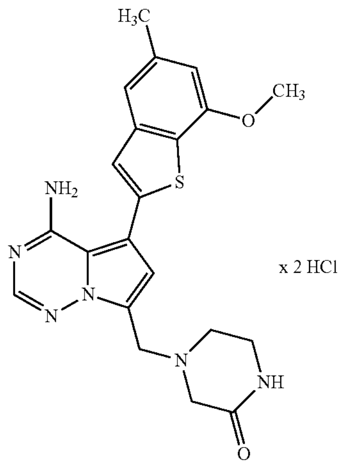 [SMILES: COc1cc(C)cc2cc(-c3cc(CN4CCNC(=O)C4)n4ncnc(N)c34)sc12]

x 2 HCl

To a suspension of Intermediate 10A (100 mg, 296 μmol) in methanol (4 ml) was added acetic acid (34 μl, 591 μmol), piperazin-2-one (44 mg, 443 μmol) and sodium cyanoborohydride (93 mg, 1.48 mmol). The mixture was stirred at 60° C. for 20 h, then filtered and evaporated. The residue was purified by preparative RP-HPLC (Reprosil C18, gradient acetonitrile/0.2% aq. TFA). The product fractions were combined, diluted with 1 M hydrochloric acid and then evaporated yielding 41 mg (26% of th.) of the title compound.

LC-MS (method 2): $R_t$=0.81 min; MS (ESIpos): m/z=422 $(M+H)^+$ $^1$H-NMR (400 MHz, DMSO-$d_6$): inter alia δ=11.08-11.66 (m, 1H), 8.38 (br. s, 1H), 8.15 (s, 1H), 7.38 (s, 1H), 7.31 (s, 1H), 7.18 (s, 1H), 6.84 (s, 1H), 4.76 (br. s, 2H), 3.96 (s, 3H), 3.79 (br. s, 2H), 3.42 (br. s, 2H), 2.45 (s, 3H) ppm.

Example 9

7-{[(3S)-3-Aminopyrrolidin-1-yl]methyl}-5-(7-methoxy-5-methyl-1-benzothiophen-2-yl)pyrrolo[2,1-f][1,2,4]triazin-4-amine

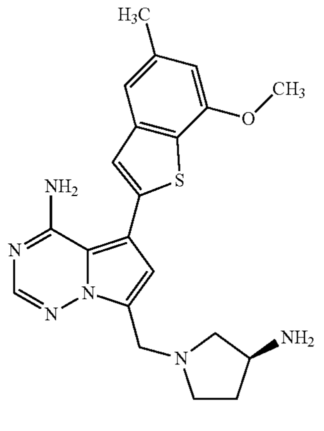 [SMILES: COc1cc(C)cc2cc(-c3cc(CN4CC[C@H](N)C4)n4ncnc(N)c34)sc12]

To a suspension of Intermediate 10A (150 mg, 92% purity, 408 μmol) in methanol (4 ml) was added acetic acid (47 μl, 816 μmol), tert-butyl (3S)-pyrrolidin-3-ylcarbamate (114 mg, 612 μmol) and sodium cyanoborohydride (128 mg, 2.04 mmol). The mixture was stirred at 60° C. for 20 h and then directly purified by preparative RP-HPLC (Reprosil C18, gradient acetonitrile/0.2% aq. formic acid). After evaporation, 73 mg (44% of th.) of the title compound were obtained (the Boc-protecting group was cleaved during evaporation).

LC-MS (method 2): $R_t$=0.63 min; MS (ESIpos): m/z=409 $(M+H)^+$ $^1$H-NMR (400 MHz, methanol-$d_4$): δ=8.22 (s, 1H), 7.47 (s, 1H), 7.34 (s, 1H), 7.32 (s, 1H), 6.82 (s, 1H), 4.98 (s, 2H), 4.14-4.25 (m, 1H), 4.00 (s, 3H), 3.52-3.88 (m, 4H), 2.70 (s, 1H), 2.49 (s, 3H), 2.23-2.34 (m, 1H) ppm.

Example 10

5-(7-Methoxy-5-methyl-1-benzothiophen-2-yl)-7-(morpholin-4-ylmethyl)pyrrolo[2,1-f][1,2,4]-triazin-4-amine

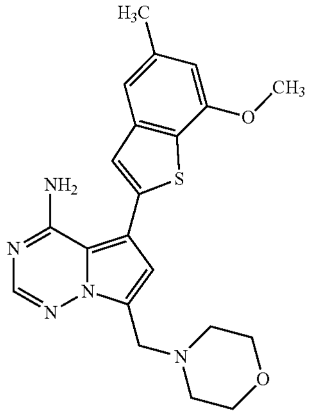 [SMILES: COc1cc(C)cc2cc(-c3cc(CN4CCOCC4)n4ncnc(N)c34)sc12]

A solution of Intermediate 10A (50 mg, 148 μmol) in THF (2 ml) was treated with morpholine (64 mg, 0.739 mmol), sodium triacetoxyborohydride (156 mg, 739 μmol) and acetic acid (17 μl, 296 μmol). The resulting mixture was stirred at 60° C. for 16 h and then directly purified by RP-HPLC (Reprosil C18, gradient acetonitrile/0.2% aq. TFA). The product fractions were combined and evaporated to dryness. The residue was dissolved in methanol and filtered through an anion exchange cartridge (Stratospheres SPE, PL-$HCO_3$ MP-resin). The cartridge was eluted with methanol, and the filtrate was evaporated affording 47 mg (77% of th.) of the title compound.

LC-MS (method 4): $R_t$=0.71 min; MS (ESIpos): m/z=410 $(M+H)^+$ $^1$H-NMR (400 MHz, DMSO-$d_6$): δ=7.98 (s, 1H), 7.35 (s, 1H), 7.28 (s, 1H), 6.82 (s, 1H), 6.77 (s, 1H), 3.95 (s, 3H), 3.84 (s, 2H), 3.56 (t, 4H), 2.48-2.42 (m, 7H) ppm.

Example 11

4-{[4-Amino-5-(7-methoxy-5-methyl-1-benzothiophen-2-yl)pyrrolo[2,1-f][1,2,4]triazin-7-yl]-methyl}-3,3-dimethylpiperazin-2-one

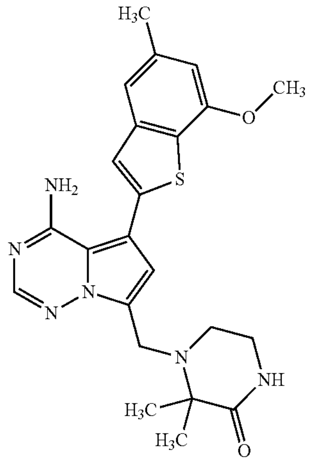 [SMILES: COc1cc(C)cc2cc(-c3cc(CN4CCNC(=O)C4(C)C)n4ncnc(N)c34)sc12]

A solution of Intermediate 10A (100 mg, 0.296 mmol) in THF (4.3 ml) was treated with 3,3-dimethylpiperazin-2-one (75 mg, 0.591 mmol), sodium triacetoxyborohydride (197 mg, 0.885 mmol) and acetic acid (33.8μl, 0.591 mmol). The resulting mixture was stirred at 60° C. for 16 h. Then, another portion of sodium triacetoxyborohydride (63 mg, 0.296 mmol) was added, and the mixture was stirred again at 60° C. for 1 h. After this, the mixture was diluted with ethyl acetate and washed with sat. aq. sodium chloride solution. The organic phase was evaporated, and the residue was purified by RP-HPLC (Reprosil C18, gradient acetonitrile/0.2% aq. TFA) followed by flash-chromatography over silica gel (dichloromethane/methanol gradient) to afford 9.8 mg (7% of th.) of the title compound.

LC-MS (method 4): $R_t$=0.82 min; MS (ESIpos): m/z=451 $(M+H)^+$ $^1$H-NMR (400 MHz, methanol-$d_4$): δ=7.88 (s, 1H), 7.26 (s, 1H), 7.25 (s, 1H), 6.82 (s, 1H), 6.75 (s, 1H), 4.04 (s, 2H), 3.98 (s, 3H), 3.21 (t, 2H), 2.92-2.84 (m, 2H), 2.47 (s, 3H), 1.47 (s, 6H) ppm.

Example 12

5-(7-Methoxy-5-methyl-1-benzothiophen-2-yl)-7-[(4-methylpiperazin-1-yl)methyl]pyrrole[2,1-f]-[1,2,4]triazin-4-amine bis(formiate)

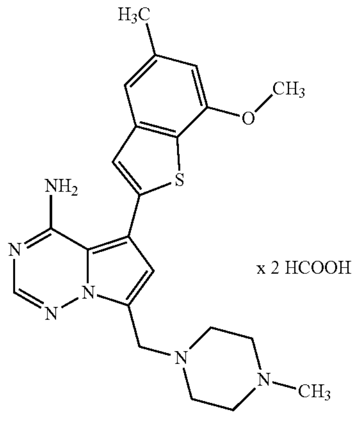 [SMILES: COc1cc(C)cc2cc(-c3cc(CN4CCN(C)CC4)n4ncnc(N)c34)sc12]

x 2 HCOOH

A solution of Example 1 (70 mg, 0.131 mmol) in methanol (1.5 ml) was treated with paraformaldehyde (19 mg, 0.653 mmol) and stirred at rt. After 30 min, sodium cyanoborohydride (15 mg, 0.235 mmol) was added, followed by acetic acid (49 μl, 0.653 mmol), and the resulting mixture was stirred at rt overnight. Then, sodium triacetoxyborohydride (50 mg, 0.235 mmol) was added, and stirring at rt was continued. After 3 hours, 37% aq. formaldehyde solution (49 μl, 0.653 mmol) was added, and the resulting mixture was heated to 60° C. overnight. The reaction was then quenched with water. The aqueous phase was extracted with dichloromethane, and the combined organic layers were washed with water, dried over sodium sulfate and evaporated. The residue was purified by preparative RP-HPLC (Reprosil C18, gradient 10-95% acetonitrile/0.1% aq. formic acid) to afford 39 mg (57% of th.) of the title compound.

LC-MS (method 1): $R_t$=0.89 min; MS (ESIpos): m/z=423 $(M+H)^+$ $^1$H-NMR (400 MHz, DMSO-$d_6$): inter al. δ=8.18 (s, 2H), 7.98 (s, 1H), 7.34 (s, 1H), 7.28 (s, 1H), 6.82 (s, 1H), 6.75 (s, 1H), 3.95 (s, 3H), 3.85 (s, 2H), 2.44 (s, 3H), 2.21 (s, 3H) ppm.

Example 13

7-[(4-Ethylpiperazin-1-yl)methyl]-5-(7-methoxy-5-methyl-1-benzothiophen-2-yl)pyrrole[2,1-f]-[1,2,4]triazin-4-amine formiate

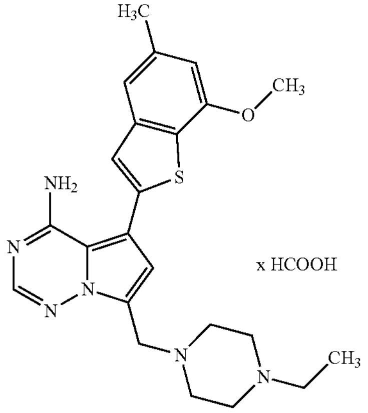 [SMILES: CCN1CCN(Cc2cc(-c3cc4cc(C)cc(OC)c4s3)c3c(N)ncnn23)CC1]

x HCOOH

A solution of Example 1 (70 mg, 0.131 mmol) in methanol (1.5 ml) was treated with acetaldehyde (36.5 μl, 0.653 mmol) and stirred at rt for 30 min. Sodium cyanoborohydride (14.8 mg, 0.235 mmol) was added together with one drop of acetic acid, and the resulting mixture was stirred at rt overnight. Then, sodium triacetoxyborohydride (49 mg, 0.235 mmol) was added, and stirring at rt was continued. After 3 hours, more sodium triacetoxyborohydride (69 mg, 0.327 mmol) was added, and the reaction mixture was stirred at 60° C. overnight. After this, the mixture was evaporated, and the residue was dissolved in THF (1.5 ml) and again treated with acetaldehyde (36.5 μl, 0.653 mmol) and sodium triacetoxyborohydride (138 mg, 0.653 mmol). The resulting mixture was stirred at 60° C. for 3 h, then diluted with water and extracted with dichloromethane. The combined organic layers were washed with water, dried over sodium sulfate and evaporated. The residue was purified by preparative RP-HPLC (Reprosil C18, gradient 10-95% acetonitrile/0.1% aq. formic acid) to afford 28 mg (44% of th.) of the title compound.

LC-MS (method 1): $R_t$=0.93 min; MS (ESIpos): m/z=437 $(M+H)^+$ $^1$H-NMR (400 MHz, DMSO-$d_6$): inter al. δ=8.18 (s, 1H), 7.98 (s, 1H), 7.34 (s, 1H), 7.28 (s, 1H), 6.82 (s, 1H), 6.75 (s, 1H), 3.95 (s, 3H), 3.85 (s, 2H), 2.44 (s, 3H), 2.37 (q, 2H), 0.98 (t, 3H) ppm.

General Procedure for the Preparation of Examples 14-56 in Table I:

A 0.1 M suspension of Intermediate 10A in methanol was treated with 1.5 eq. of the appropriate amine, 5 eq. of sodium cyanoborohydride and 2 eq. of acetic acid. The resulting mixture was stirred at 60° C. for 3-20 h and then purified according to the methods indicated.

For the synthesis of Examples 53-56, the appropriate amine component was protected at the primary amino group with a tert-butoxycarbonyl (Boc) group, which was cleaved after the purification by treatment with a 4 M solution of hydrogen chloride in 1,4-dioxane (stirring at rt for 2 h). Evaporation of the volatiles and drying in vacuo afforded the final products.

TABLE I

| Example No. | Structure | Purification method(s) | LC-MS data |
|---|---|---|---|
| 14 | 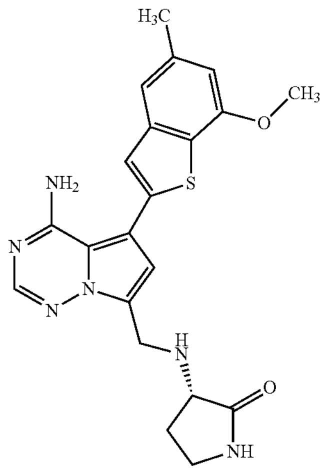 [SMILES: COc1cc(C)cc2cc(-c3cc(CN[C@H]4CCNC4=O)n4ncnc(N)c34)sc12] | P1 | Method 2: $R_t$ = 0.69 min; MS (ESIpos): m/z = 423 $(M + H)^+$ |
| 15 | 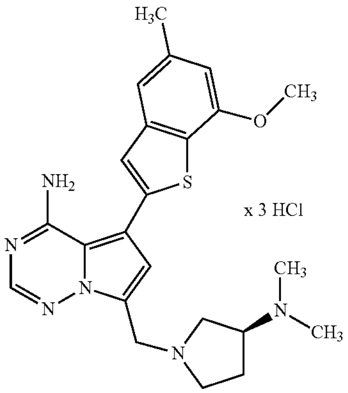 [SMILES: COc1cc(C)cc2cc(-c3cc(CN4CC[C@H](N(C)C)C4)n4ncnc(N)c34)sc12] | P2; P4 | Method 4: $R_t$ = 0.64 min; MS (ESIpos): m/z = 437 $(M + H)^+$ |
| 16 | 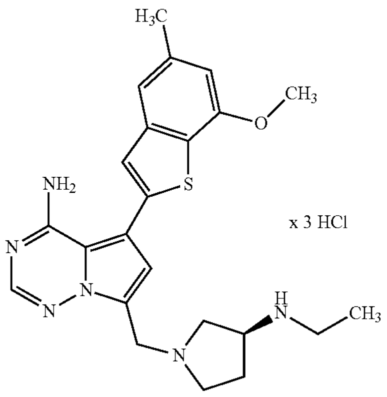 [SMILES: CCN[C@H]1CCN(Cc2cc(-c3cc4cc(C)cc(OC)c4s3)c3c(N)ncnn23)C1] | P2; P4 | Method 2: $R_t$ = 0.67 min; MS (ESIpos): m/z = 437 $(M + H)^+$ |

TABLE I-continued
| Example No. | Structure | Purification method(s) | LC-MS data |
|---|---|---|---|
| 17 | 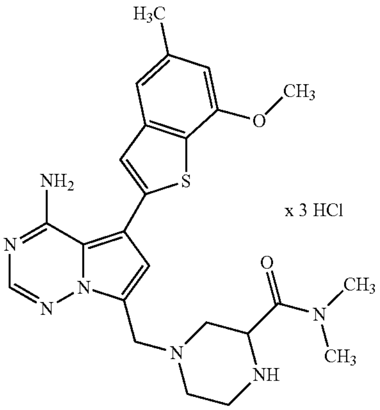 [SMILES: COc1cc(C)cc2cc(-c3cc(CN4CCNC(C(=O)N(C)C)C4)n4ncnc(N)c34)sc12] x 3 HCl | P2; P4 | Method 4: $R_t$ = 0.73 min; MS (ESIpos): m/z = 480 $(M + H)^+$ |
| 18 | 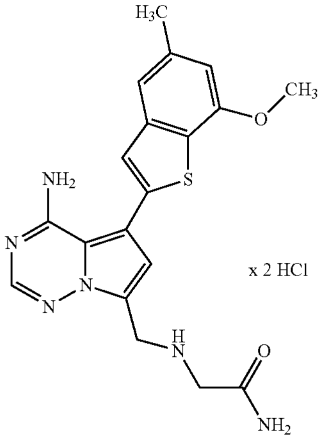 [SMILES: COc1cc(C)cc2cc(-c3cc(CNCC(N)=O)n4ncnc(N)c34)sc12] x 2 HCl | P5; P2; P4 | Method 4: $R_t$ = 0.64 min; MS (ESIpos): m/z = 397 $(M + H)^+$ |
| 19 | 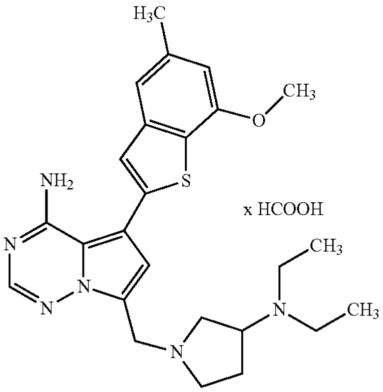 [SMILES: CCN(CC)C1CCN(Cc2cc(-c3cc4cc(C)cc(OC)c4s3)c3c(N)ncnn23)C1] x HCOOH | P3 | Method 2: $R_t$ = 0.73 min; MS (ESIpos): m/z = 465 $(M + H)^+$ |

TABLE I-continued
| Example No. | Structure | Purification method(s) | LC-MS data |
|---|---|---|---|
| 20 | 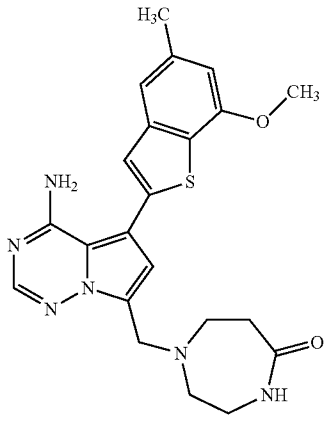 [SMILES: COc1cc(C)cc2cc(-c3cc(CN4CCNC(=O)CC4)n4ncnc(N)c34)sc12] | P5; P3 | Method 2: $R_t$ = 0.73 min; MS (ESIpos): m/z = 437 $(M + H)^+$ |
| 21 | 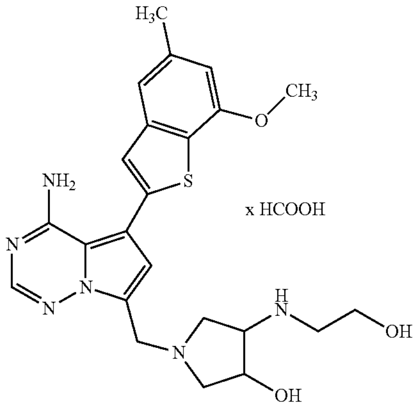 [SMILES: COc1cc(C)cc2cc(-c3cc(CN4CC(O)C(NCCO)C4)n4ncnc(N)c34)sc12] x HCOOH | P3 | Method 2: $R_t$ = 0.71 min; MS (ESIpos): m/z = 469 $(M + H)^+$ |
| 22 | 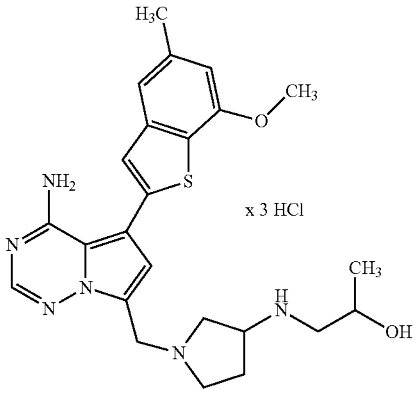 [SMILES: COc1cc(C)cc2cc(-c3cc(CN4CCC(NCC(C)O)C4)n4ncnc(N)c34)sc12] x 3 HCl | P5; P3; P4 | Method 1: $R_t$ = 0.80 min; MS (ESIpos): m/z = 467 $(M + H)^+$ |

TABLE I-continued
| Example No. | Structure | Purification method(s) | LC-MS data |
|---|---|---|---|
| 23 | 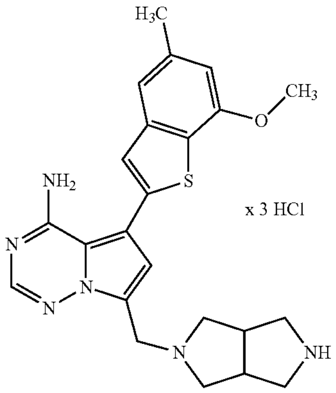 [SMILES: COc1cc(C)cc2cc(-c3cc(CN4CC5CNCC5C4)n4ncnc(N)c34)sc12] x 3 HCl | P5; P3; P4 | Method 2: $R_t$ = 0.64 min; MS (ESIpos): m/z = 435 $(M + H)^+$ |
| 24 | 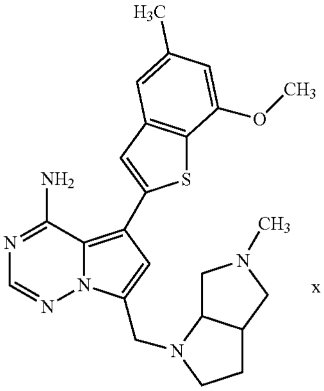 x 3 HCl | P5; P3; P4 | Method 1: $R_t$ = 0.94 min; MS (ESIpos): m/z = 449 $(M + H)^+$ |
| 25 | 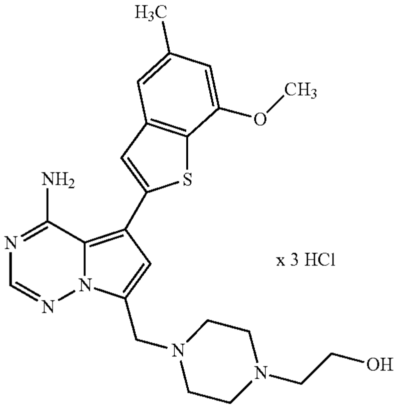 [SMILES: COc1cc(C)cc2cc(-c3cc(CN4CCN(CCO)CC4)n4ncnc(N)c34)sc12] x 3 HCl | P5; P3; P4 | Method 4: $R_t$ = 0.66 min; MS (ESIpos): m/z = 453 $(M + H)^+$ |

TABLE I-continued
| Example No. | Structure | Purification method(s) | LC-MS data |
|---|---|---|---|
| 26 | 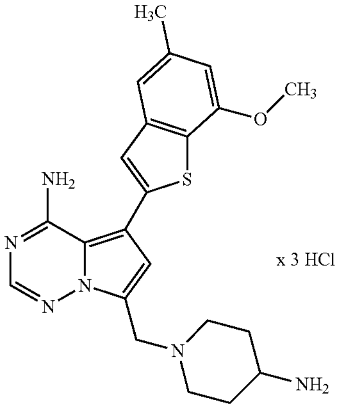 [SMILES: COc1cc(C)cc2cc(-c3cc(CN4CCC(N)CC4)n4ncnc(N)c34)sc12] x 3 HCl | P5; P3; P4 | Method 4: $R_t$ = 0.51 min; MS (ESIpos): m/z = 423 $(M + H)^+$ |
| 27 | 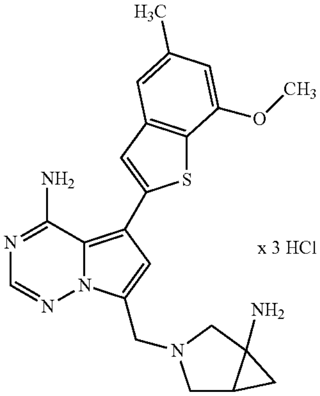 [SMILES: COc1cc(C)cc2cc(-c3cc(CN4CC5CC5(N)C4)n4ncnc(N)c34)sc12] x 3 HCl | P5; P3; P4 | Method 1: $R_t$ = 0.86 min; MS (ESIpos): m/z = 421 $(M + H)^+$ |
| 28 | 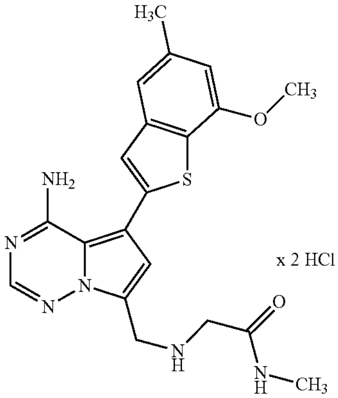 [SMILES: CNC(=O)CNCc1cc(-c2cc3cc(C)cc(OC)c3s2)c2c(N)ncnn12] x 2 HCl | P5; P3; P4 | Method 1: $R_t$ = 0.87 min; MS (ESIpos): m/z = 411 $(M + H)^+$ |
| 29 | 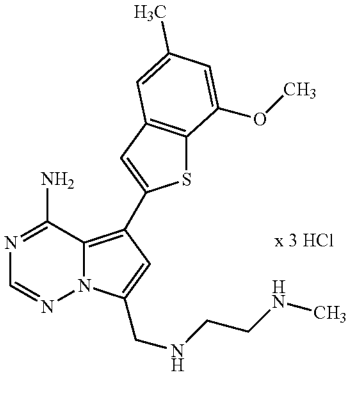 [SMILES: CNCCNCc1cc(-c2cc3cc(C)cc(OC)c3s2)c2c(N)ncnn12] x 3 HCl | P3; P4 | Method 1: $R_t$ = 0.77 min; MS (ESIpos): m/z = 397 $(M + H)^+$ |

TABLE I-continued
| Example No. | Structure | Purification method(s) | LC-MS data |
|---|---|---|---|
| 30 | 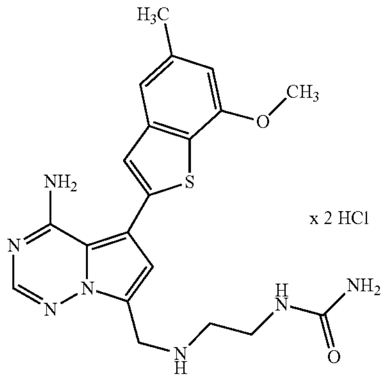 [SMILES: COc1cc(C)cc2cc(-c3cc(CNCCNC(N)=O)n4ncnc(N)c34)sc12] x 2 HCl | P3; P4 | Method 2: $R_t$ = 0.66 min; MS (ESIpos): m/z = 426 $(M + H)^+$ |
| 31 | 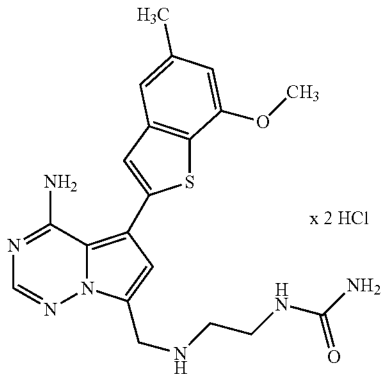 [SMILES: COc1cc(C)cc2cc(-c3cc(CNCCNC(N)=O)n4ncnc(N)c34)sc12] x 2 HCl | P3; P4 | Method 2: $R_t$ = 0.67 min; MS (ESIpos): m/z = 425 $(M + H)^+$ |
| 32 | 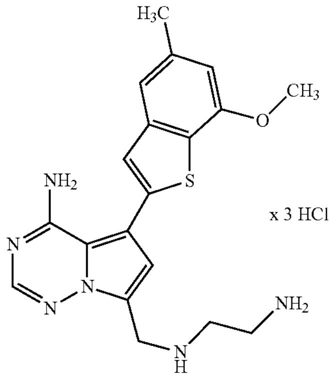 [SMILES: COc1cc(C)cc2cc(-c3cc(CNCCN)n4ncnc(N)c34)sc12] x 3 HCl | P3; P4 | Method 1: $R_t$ = 0.73 min; MS (ESIpos): m/z = 383 $(M + H)^+$ |
| 33 | 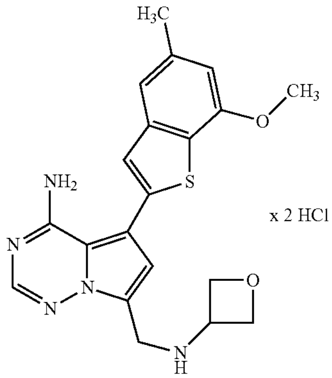 x 2 HCl | P3; P4 | Method 2: $R_t$ = 0.69 min; MS (ESIpos): m/z = 423 $(M + H)^+$ |

TABLE I-continued
| Example No. | Structure | Purification method(s) | LC-MS data |
| --- | --- | --- | --- |
| 34 | 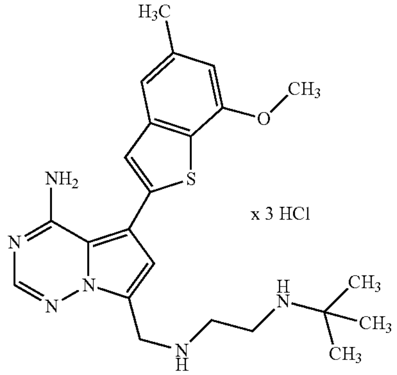 [SMILES: COc1cc(C)cc2cc(-c3cc(CNCCNC(C)(C)C)n4ncnc(N)c34)sc12] x 3 HCl | P3; P4 | Method 2: $R_t$ = 0.74 min; MS (ESIpos): m/z = 439 $(M + H)^+$ |
| 35 | 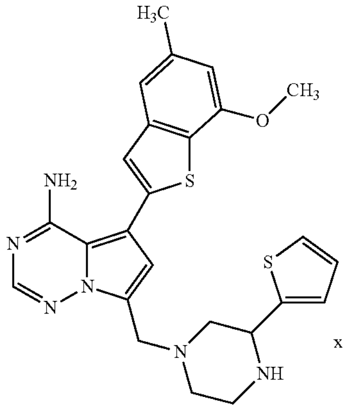 x 3 HCl | P2; P4 | Method 4: $R_t$ = 0.76 min; MS (ESIpos): m/z = 491 $(M + H)^+$ |
| 36 | 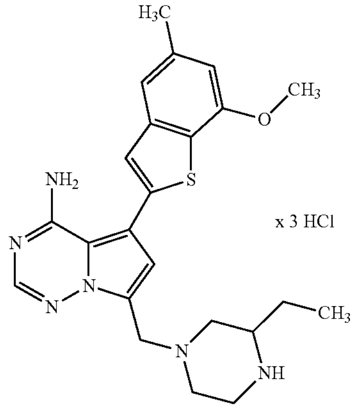 [SMILES: CCC1CN(Cc2cc(-c3cc4cc(C)cc(OC)c4s3)c3c(N)ncnn23)CCN1] x 3 HCl | P2; P4 | Method 4: $R_t$ = 0.70 min; MS (ESIpos): m/z = 437 $(M + H)^+$ |

TABLE I-continued
| Example No. | Structure | Purification method(s) | LC-MS data |
|---|---|---|---|
| 37 | 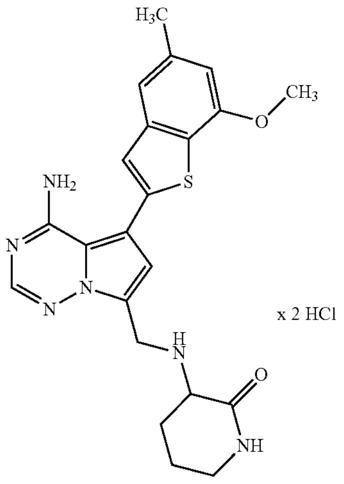 [SMILES: COc1cc(C)cc2cc(-c3cc(CNC4CCCNC4=O)n4ncnc(N)c34)sc12] | P2; P4 | Method 4: $R_t$ = 0.65 min; MS (ESIpos): m/z = 437 $(M + H)^+$ |
| 38 | 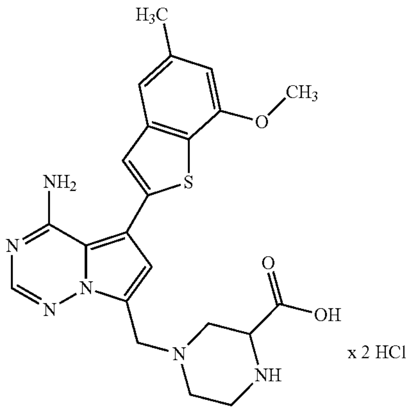 [SMILES: COc1cc(C)cc2cc(-c3cc(CN4CCNC(C(=O)O)C4)n4ncnc(N)c34)sc12] | P2; P4 | Method 4: $R_t$ = 0.66 min; MS (ESIpos): m/z = 453 $(M + H)^+$ |
| 39 | 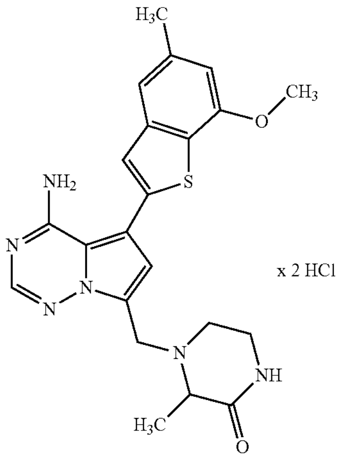 [SMILES: COc1cc(C)cc2cc(-c3cc(CN4CCNC(=O)C4C)n4ncnc(N)c34)sc12] | P2; P4 | Method 2: $R_t$ = 0.76 min; MS (ESIpos): m/z = 437 $(M + H)^+$ |

TABLE I-continued
| Example No. | Structure | Purification method(s) | LC-MS data |
|---|---|---|---|
| 40 | 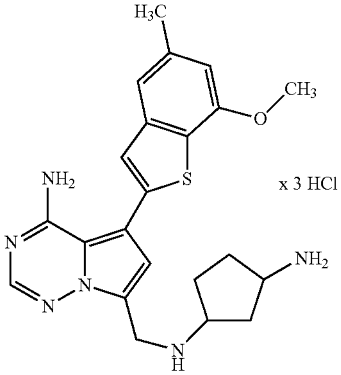 [SMILES: COc1cc(C)cc2cc(-c3cc(CNC4CCC(N)C4)n4ncnc(N)c34)sc12] x 3 HCl | P2; P4 | Method 2: $R_t$ = 0.57 min; MS (ESIpos): m/z = 423 $(M + H)^+$ |
| 41 | 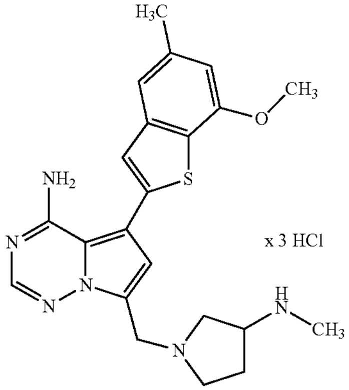 [SMILES: CNC1CCN(Cc2cc(-c3cc4cc(C)cc(OC)c4s3)c3c(N)ncnn23)C1] x 3 HCl | P2; P4 | Method 2: $R_t$ = 0.70 min; MS (ESIpos): m/z = 423 $(M + H)^+$ |
| 42 | 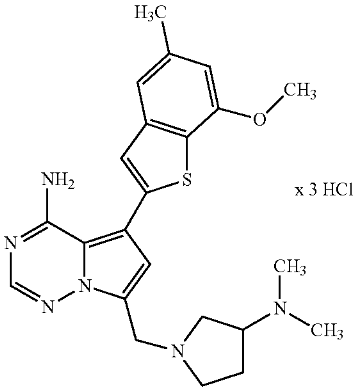 [SMILES: COc1cc(C)cc2cc(-c3cc(CN4CCC(N(C)C)C4)n4ncnc(N)c34)sc12] x 3 HCl | P2; P4 | Method 2: $R_t$ = 0.69 min; MS (ESIpos): m/z = 437 $(M + H)^+$ |

TABLE I-continued
| Example No. | Structure | Purification method(s) | LC-MS data |
|---|---|---|---|
| 43 | 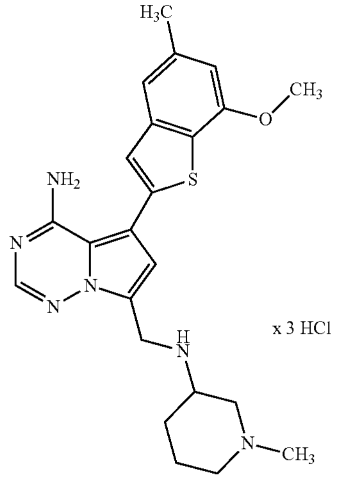 [SMILES: COc1cc(C)cc2cc(-c3cc(CNC4CCCN(C)C4)n4ncnc(N)c34)sc12] | P2; P4 | Method 2: $R_t$ = 0.69 min; MS (ESIpos): m/z = 437 $(M + H)^+$ |
| 44 | 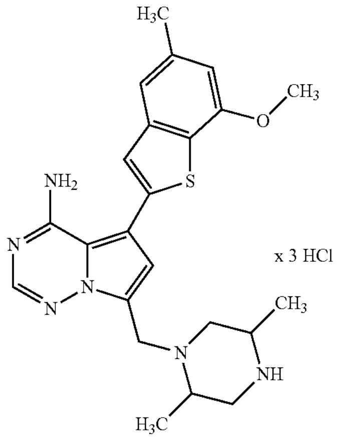 [SMILES: COc1cc(C)cc2cc(-c3cc(CN4CC(C)NCC4C)n4ncnc(N)c34)sc12] | P5; P2; P4 | Method 2: $R_t$ = 0.73 min; MS (ESIpos): m/z = 437 $(M + H)^+$ |
| 45 | 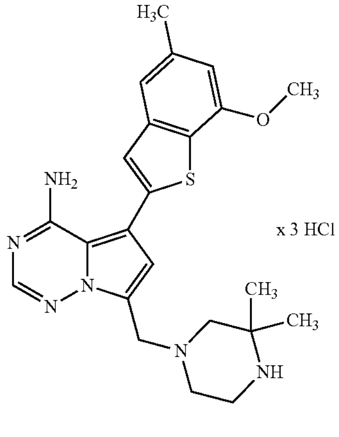 [SMILES: COc1cc(C)cc2cc(-c3cc(CN4CCNC(C)(C)C4)n4ncnc(N)c34)sc12] | P2; P4 | Method 2: $R_t$ = 0.75 min; MS (ESIpos): m/z = 437 $(M + H)^+$ |

TABLE I-continued
| Example No. | Structure | Purification method(s) | LC-MS data |
|---|---|---|---|
| 46 | 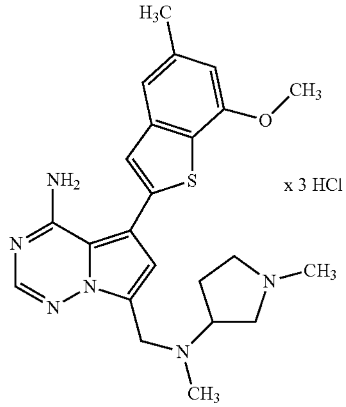 [SMILES: COc1cc(C)cc2cc(-c3cc(CN(C)C4CCN(C)C4)n4ncnc(N)c34)sc12] x 3 HCl | P2; P4 | Method 2: $R_t$ = 0.64 min; MS (ESIpos): m/z = 437 $(M + H)^+$ |
| 47 | 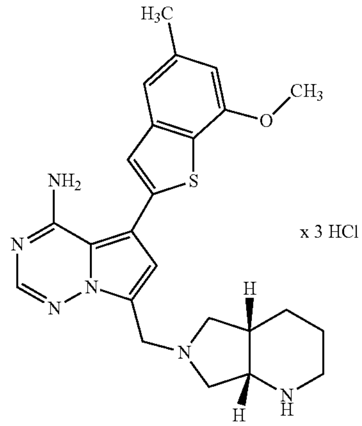 [SMILES: COc1cc(C)cc2cc(-c3cc(CN4C[C@@H]5CCCN[C@@H]5C4)n4ncnc(N)c34)sc12] x 3 HCl | P2; P4 | Method 2: $R_t$ = 0.63 min; MS (ESIpos): m/z = 449 $(M + H)^+$ |
| 48 | 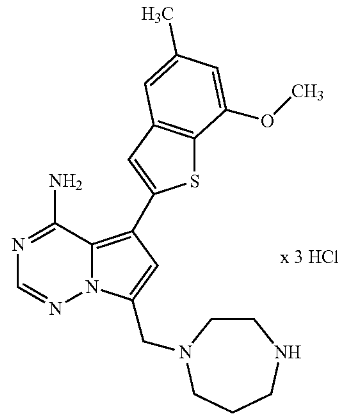 [SMILES: COc1cc(C)cc2cc(-c3cc(CN4CCCNCC4)n4ncnc(N)c34)sc12] x 3 HCl | P2; P4 | Method 4: $R_t$ = 0.57 min; MS (ESIpos): m/z = 423 $(M + H)^+$ |

TABLE I-continued
| Example No. | Structure | Purification method(s) | LC-MS data |
|---|---|---|---|
| 49 | 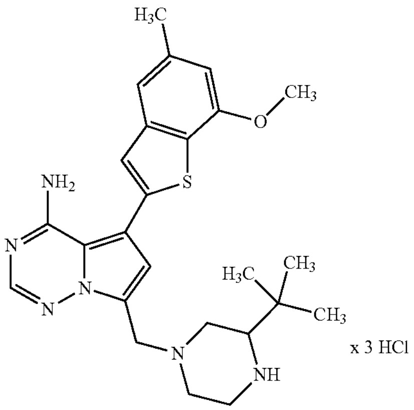 [SMILES: COc1cc(C)cc2cc(-c3cc(CN4CCNC(C(C)(C)C)C4)n4ncnc(N)c34)sc12] | P2; P4 | Method 2: $R_t$ = 0.85 min; MS (ESIpos): m/z = 465 $(M + H)^+$ |
| 50 | 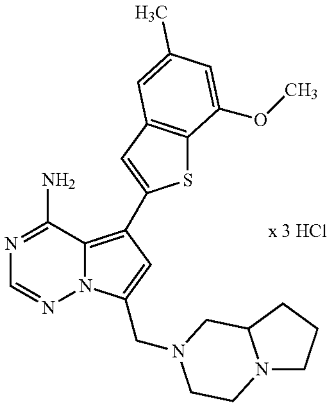 [SMILES: COc1cc(C)cc2cc(-c3cc(CN4CCN5CCCC5C4)n4ncnc(N)c34)sc12] | P2; P4 | Method 2: $R_t$ = 0.80 min; MS (ESIpos): m/z = 449 $(M + H)^+$ |
| 51 | 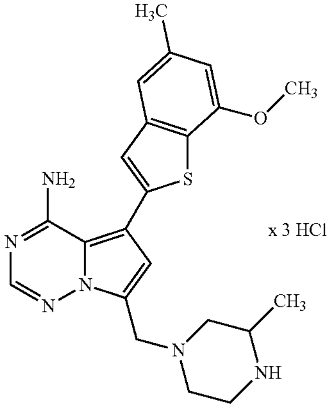 [SMILES: COc1cc(C)cc2cc(-c3cc(CN4CCNC(C)C4)n4ncnc(N)c34)sc12] | P2; P4 | Method 2: $R_t$ = 0.77 min; MS (ESIpos): m/z = 423 $(M + H)^+$ |

TABLE I-continued
| Example No. | Structure | Purification method(s) | LC-MS data |
|---|---|---|---|
| 52 | 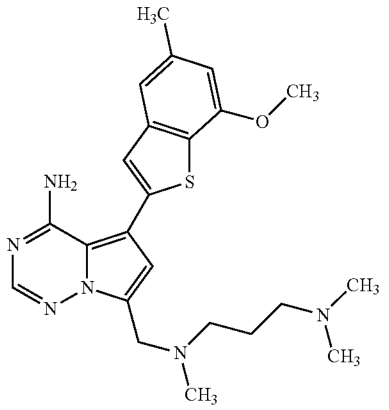 x 3 HCl | P2; P4 | Method 4: $R_t$ = 0.50 min; MS (ESIpos): m/z = 439 $(M + H)^+$ |
| 53 | 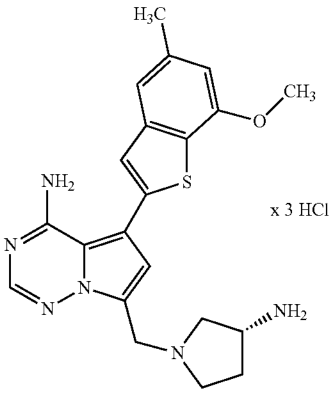 [SMILES: COc1cc(C)cc2cc(-c3cc(CN4CC[C@@H](N)C4)n4ncnc(N)c34)sc12] x 3 HCl | P3 | Method 4: $R_t$ = 0.50 min; MS (ESIpos): m/z = 409 $(M + H)^+$ |
| 54 | 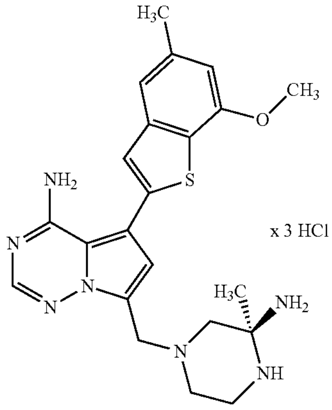 [SMILES: COc1cc(C)cc2cc(-c3cc(CN4CCN[C@](C)(N)C4)n4ncnc(N)c34)sc12] x 3 HCl | P3 | Method 4: $R_t$ = 0.75 min; MS (ESIpos): m/z = 437 $(M + H)^+$ |

TABLE I-continued

| Example No. | Structure | Purification method(s) | LC-MS data |
|---|---|---|---|
| 55 | 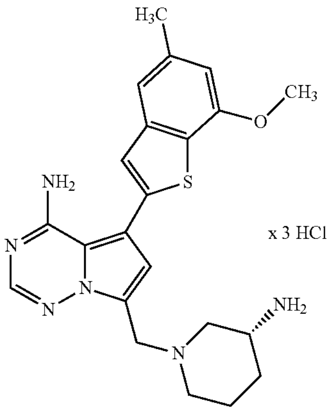 [SMILES: COc1cc(C)cc2cc(-c3cc(CN4CCC[C@@H](N)C4)n4ncnc(N)c34)sc12] x 3 HCl | P3 | Method 4: $R_t$ = 0.58 min; MS (ESIpos): m/z = 423 $(M + H)^+$ |
| 56 | 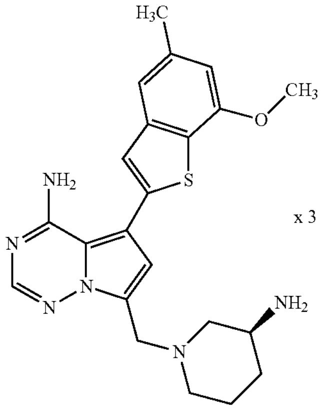 x 3 HCl | P3 | Method 2: $R_t$ = 0.62 min; MS (ESIpos): m/z = 423 $(M + H)^+$ |

General Procedure for the Preparation of Examples 57-92 in Table II:

A 0.17 M solution of Intermediate 10A in ethanol was treated with 1.5 eq. of the appropriate amine, 5 eq. of sodium cyanoborohydride and 2 eq. of acetic acid. The resulting mixture was shaken overnight at 60° C. and then evaporated. The crude product thus obtained was dissolved in DMSO and purified according to the methods indicated.

TABLE II

| Example No. | Structure | Purification method | LC-MS data |
|---|---|---|---|
| 57 | 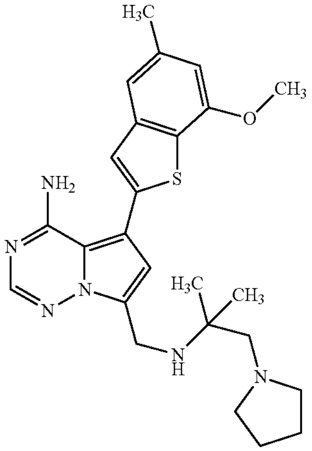 [SMILES: COc1cc(C)cc2cc(-c3cc(CNC(C)(C)CN4CCCC4)n4ncnc(N)c34)sc12] | P7 or P8 | Method 6: $R_t$ = 1.41 min; MS (ESIpos): m/z = 465 $(M + H)^+$ |

TABLE II-continued
| Example No. | Structure | Purification method | LC-MS data |
| --- | --- | --- | --- |
| 58 | 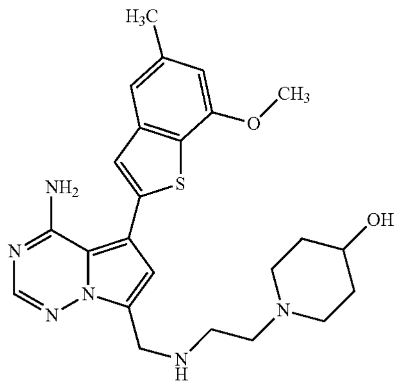 [SMILES: COc1cc(C)cc2cc(-c3cc(CNCCN4CCC(O)CC4)n4ncnc(N)c34)sc12] | P7 or P8 | Method 6: $R_t$ = 1.21 min; MS (ESIpos): m/z = 467 $(M + H)^+$ |
| 59 | 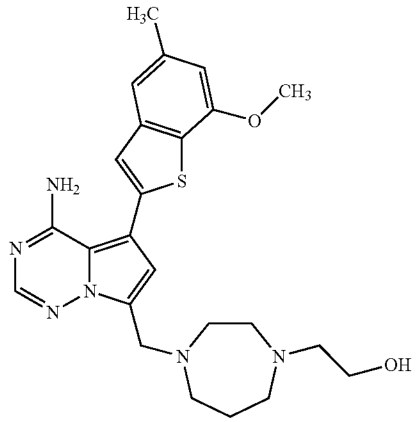 [SMILES: COc1cc(C)cc2cc(-c3cc(CN4CCCN(CCO)CC4)n4ncnc(N)c34)sc12] | P7 or P8 | Method 6: $R_t$ = 1.25 min; MS (ESIpos): m/z = 467 $(M + H)^+$ |
| 60 | 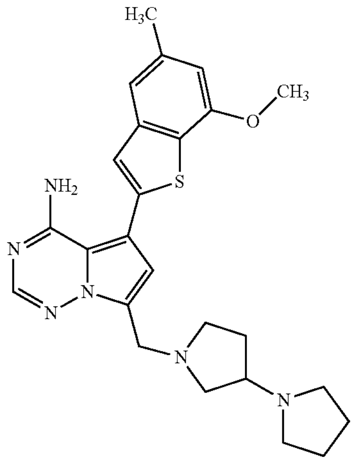 [SMILES: COc1cc(C)cc2cc(-c3cc(CN4CCC(N5CCCC5)C4)n4ncnc(N)c34)sc12] | P7 or P8 | Method 6: $R_t$ = 1.27 min; MS (ESIpos): m/z = 463 $(M + H)^+$ |

TABLE II-continued
| Example No. | Structure | Purification method | LC-MS data |
|---|---|---|---|
| 61 | 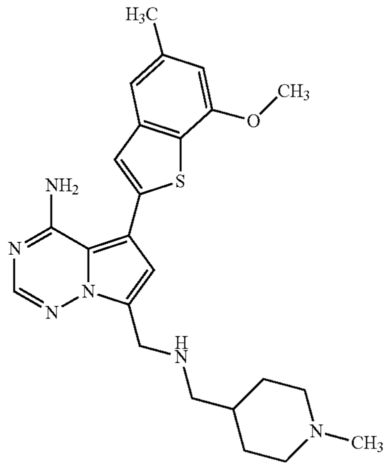 [SMILES: COc1cc(C)cc2cc(-c3cc(CNCC4CCN(C)CC4)n4ncnc(N)c34)sc12] | P7 or P8 | Method 6: $R_t$ = 1.21 min; MS (ESIpos): m/z = 451 $(M + H)^+$ |
| 62 | 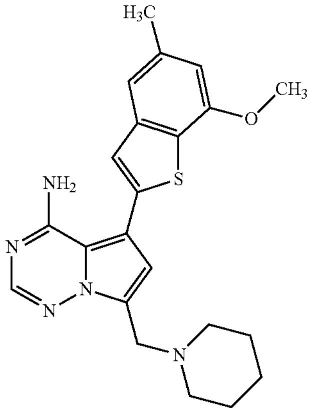 [SMILES: COc1cc(C)cc2cc(-c3cc(CN4CCCCC4)n4ncnc(N)c34)sc12] | P7 or P8 | Method 6: $R_t$ = 1.48 min; MS (ESIpos): m/z = 407 $(M + H)^+$ |
| 63 | 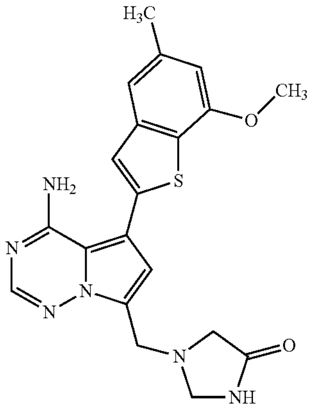 [SMILES: COc1cc(C)cc2cc(-c3cc(CN4CNC(=O)C4)n4ncnc(N)c34)sc12] | P7 or P8 | Method 6: $R_t$ = 1.61 min; MS (ESIpos): m/z = 409 $(M + H)^+$ |

TABLE II-continued
| Example No. | Structure | Purification method | LC-MS data |
| --- | --- | --- | --- |
| 64 | 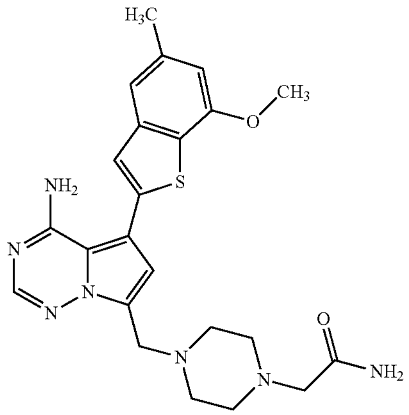 [SMILES: COc1cc(C)cc2cc(-c3cc(CN4CCN(CC(N)=O)CC4)n4ncnc(N)c34)sc12] | P7 or P8 | Method 6: $R_t$ = 1.37 min; MS (ESIpos): m/z = 466 $(M + H)^+$ |
| 65 | 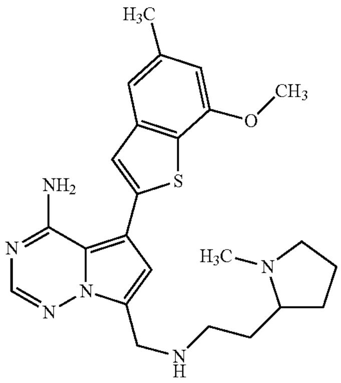 [SMILES: COc1cc(C)cc2cc(-c3cc(CNCCC4CCCN4C)n4ncnc(N)c34)sc12] | P7 or P8 | Method 6: $R_t$ = 1.21 min; MS (ESIpos): m/z = 451 $(M + H)^+$ |
| 66 | 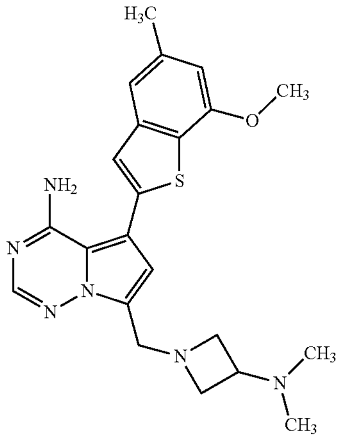 [SMILES: COc1cc(C)cc2cc(-c3cc(CN4CC(N(C)C)C4)n4ncnc(N)c34)sc12] | P7 or P8 | Method 6: $R_t$ = 1.27 min; MS (ESIpos): m/z = 423 $(M + H)^+$ |

TABLE II-continued
| Example No. | Structure | Purification method | LC-MS data |
|---|---|---|---|
| 67 | 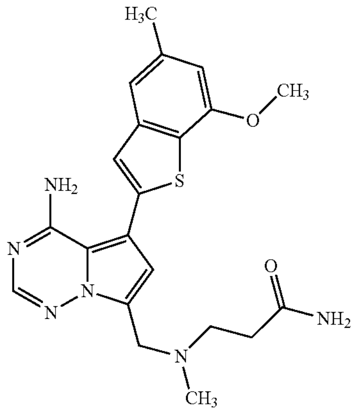 [SMILES: COc1cc(C)cc2cc(-c3cc(CN(C)CCC(N)=O)n4ncnc(N)c34)sc12] | P7 or P8 | Method 6: $R_t$ = 1.38 min; MS (ESIpos): m/z = 425 $(M + H)^+$ |
| 68 | 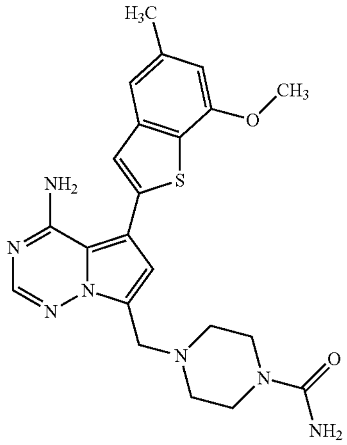 [SMILES: COc1cc(C)cc2cc(-c3cc(CN4CCN(C(N)=O)CC4)n4ncnc(N)c34)sc12] | P7 or P8 | Method 6: $R_t$ = 1.36 min; MS (ESIpos): m/z = 452 $(M + H)^+$ |
| 69 | 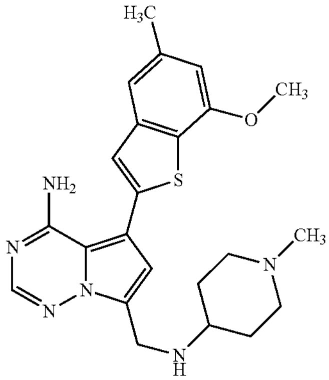 [SMILES: COc1cc(C)cc2cc(-c3cc(CNC4CCN(C)CC4)n4ncnc(N)c34)sc12] | P7 or P8 | Method 6: $R_t$ = 1.20 min; MS (ESIpos): m/z = 437 $(M + H)^+$ |

TABLE II-continued
| Example No. | Structure | Purification method | LC-MS data |
|---|---|---|---|
| 70 | 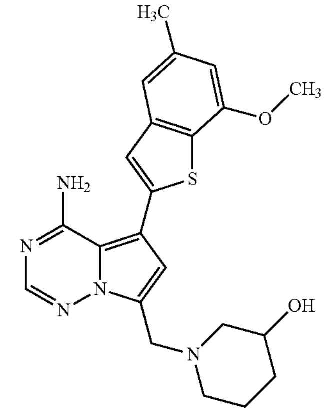 [SMILES: COc1cc(C)cc2cc(-c3cc(CN4CCCC(O)C4)n4ncnc(N)c34)sc12] | P7 or P8 | Method 6: $R_t$ = 1.41 min; MS (ESIpos): m/z = 424 $(M + H)^+$ |
| 71 | 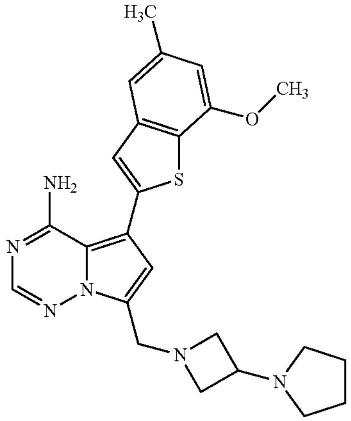 [SMILES: COc1cc(C)cc2cc(-c3cc(CN4CC(N5CCCC5)C4)n4ncnc(N)c34)sc12] | P7 or P8 | Method 6: $R_t$ = 1.28 min; MS (ESIpos): m/z = 449 $(M + H)^+$ |
| 72 | 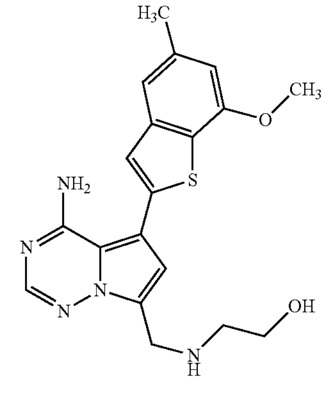 [SMILES: COc1cc(C)cc2cc(-c3cc(CNCCO)n4ncnc(N)c34)sc12] | P7 or P8 | Method 6: $R_t$ = 1.37 min; MS (ESIpos): m/z = 384 $(M + H)^+$ |

TABLE II-continued
| Example No. | Structure | Purification method | LC-MS data |
|---|---|---|---|
| 73 | 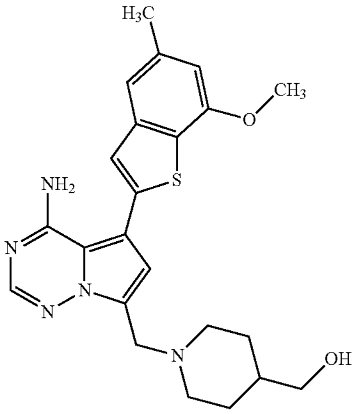 [SMILES: COc1cc(C)cc2cc(-c3cc(CN4CCC(CO)CC4)n4ncnc(N)c34)sc12] | P7 or P8 | Method 6: $R_t$ = 1.40 min; MS (ESIpos): m/z = 438 $(M + H)^+$ |
| 74 | 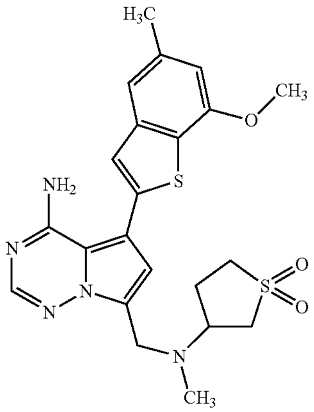 [SMILES: COc1cc(C)cc2cc(-c3cc(CN(C)C4CCS(=O)(=O)C4)n4ncnc(N)c34)sc12] | P7 or P8 | Method 6: $R_t$ = 1.55 min; MS (ESIpos): m/z = 472 $(M + H)^+$ |
| 75 | 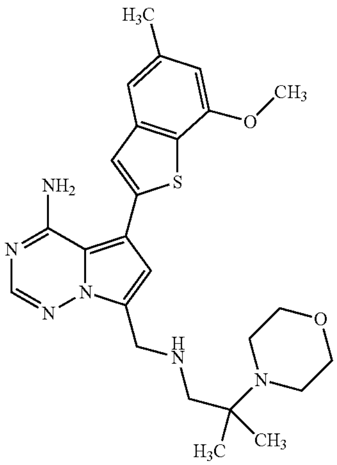 [SMILES: COc1cc(C)cc2cc(-c3cc(CNCC(C)(C)N4CCOCC4)n4ncnc(N)c34)sc12] | P7 or P8 | Method 6: $R_t$ = 1.47 min; MS (ESIpos): m/z = 481 $(M + H)^+$ |

TABLE II-continued
| Example No. | Structure | Purification method | LC-MS data |
|---|---|---|---|
| 76 | 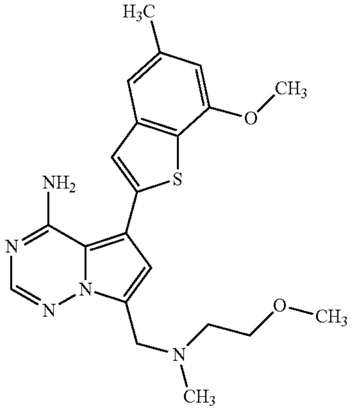 [SMILES: COCCN(C)Cc1cc(-c2cc3cc(C)cc(OC)c3s2)c2c(N)ncnn12] | P7 or P8 | Method 6: $R_t$ = 1.46 min; MS (ESIpos): m/z = 412 $(M + H)^+$ |
| 77 | 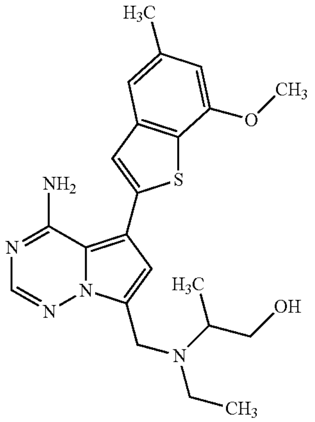 [SMILES: CCN(Cc1cc(-c2cc3cc(C)cc(OC)c3s2)c2c(N)ncnn12)C(C)CO] | P7 or P8 | Method 6: $R_t$ = 1.46 min; MS (ESIpos): m/z = 426 $(M + H)^+$ |
| 78 | 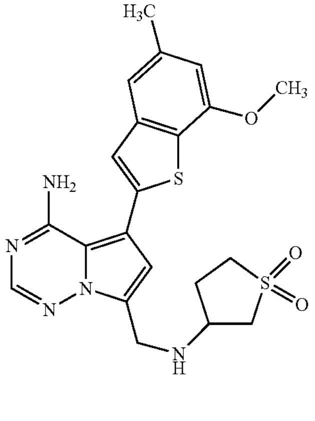 [SMILES: COc1cc(C)cc2cc(-c3cc(CNC4CCS(=O)(=O)C4)n4ncnc(N)c34)sc12] | P7 or P8 | Method 6: $R_t$ = 1.45 min; MS (ESIpos): m/z = 458 $(M + H)^+$ |

TABLE II-continued
| Example No. | Structure | Purification method | LC-MS data |
|---|---|---|---|
| 79 | 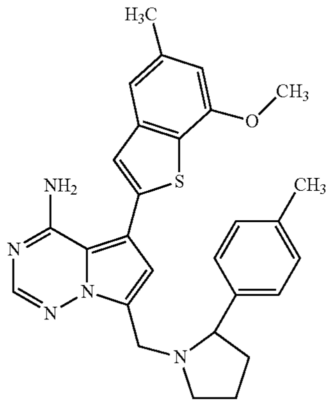 [SMILES: COc1cc(C)cc2cc(-c3cc(CN4CCCC4c4ccc(C)cc4)n4ncnc(N)c34)sc12] | P7 or P8 | Method 6: $R_t$ = 1.62 min; MS (ESIpos): m/z = 484 $(M + H)^+$ |
| 80 | 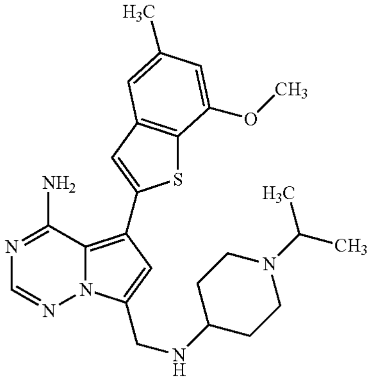 [SMILES: COc1cc(C)cc2cc(-c3cc(CNC4CCN(C(C)C)CC4)n4ncnc(N)c34)sc12] | P7 or P8 | Method 6: $R_t$ = 1.21 min; MS (ESIpos): m/z = 465 $(M + H)^+$ |
| 81 | 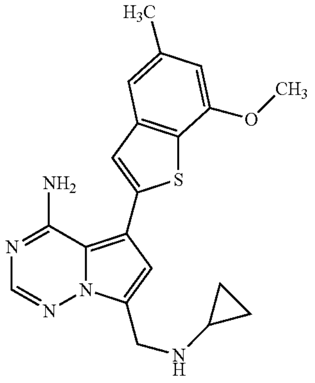 [SMILES: COc1cc(C)cc2cc(-c3cc(CNC4CC4)n4ncnc(N)c34)sc12] | P7 or P8 | Method 6: $R_t$ = 1.44 min; MS (ESIpos): m/z = 380 $(M + H)^+$ |
| 82 | 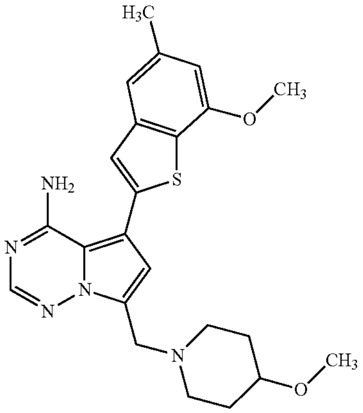 [SMILES: COc1cc(C)cc2cc(-c3cc(CN4CCC(OC)CC4)n4ncnc(N)c34)sc12] | P7 or P8 | Method 6: $R_t$ = 1.46 min; MS (ESIpos): m/z = 438 $(M + H)^+$ |

TABLE II-continued
| Example No. | Structure | Purification method | LC-MS data |
|---|---|---|---|
| 83 | 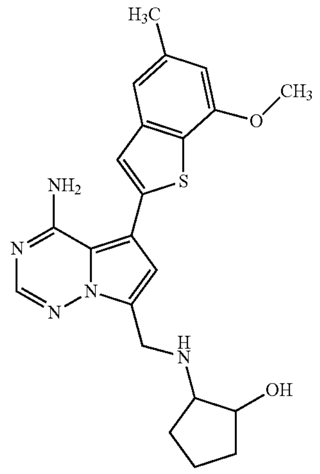 [SMILES: COc1cc(C)cc2cc(-c3cc(CNC4CCCC4O)n4ncnc(N)c34)sc12] | P7 or P8 | Method 6: $R_t$ = 1.42 min; MS (ESIpos): m/z = 424 $(M + H)^+$ |
| 84 | 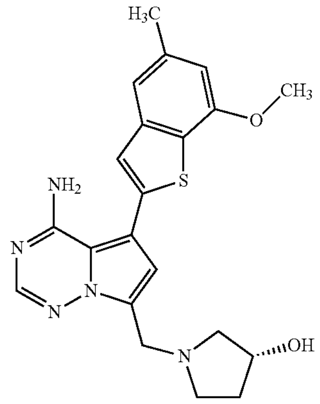 [SMILES: COc1cc(C)cc2cc(-c3cc(CN4CC[C@@H](O)C4)n4ncnc(N)c34)sc12] | P7 or P8 | Method 6: $R_t$ = 1.39 min; MS (ESIpos): m/z = 410 $(M + H)^+$ |
| 85 | 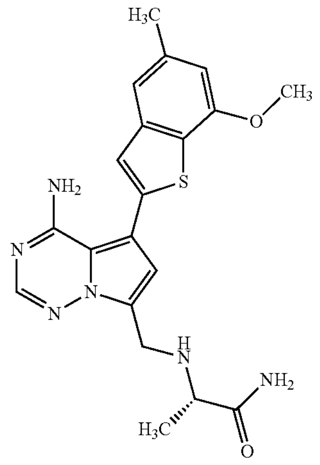 [SMILES: COc1cc(C)cc2cc(-c3cc(CN[C@@H](C)C(N)=O)n4ncnc(N)c34)sc12] | P7 or P8 | Method 6: $R_t$ = 1.36 min; MS (ESIpos): m/z = 411 $(M + H)^+$ |

TABLE II-continued
| Example No. | Structure | Purification method | LC-MS data |
|---|---|---|---|
| 86 | 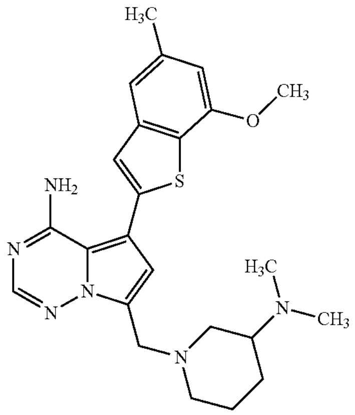 [SMILES: COc1cc(C)cc2cc(-c3cc(CN4CCCC(N(C)C)C4)n4ncnc(N)c34)sc12] | P7 or P8 | Method 6: $R_t$ = 1.28 min; MS (ESIpos): m/z = 451 $(M + H)^+$ |
| 87 | 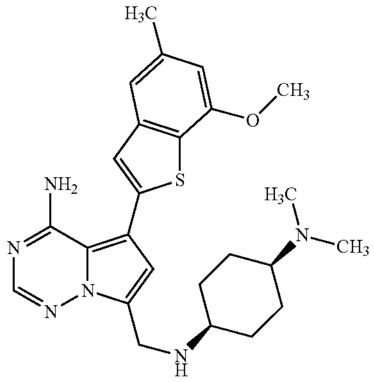 [SMILES: COc1cc(C)cc2cc(-c3cc(CN[C@H]4CC[C@@H](N(C)C)CC4)n4ncnc(N)c34)sc12] | P7 or P8 | Method 6: $R_t$ = 1.21 min; MS (ESIpos): m/z = 465 $(M + H)^+$ |
| 88 | 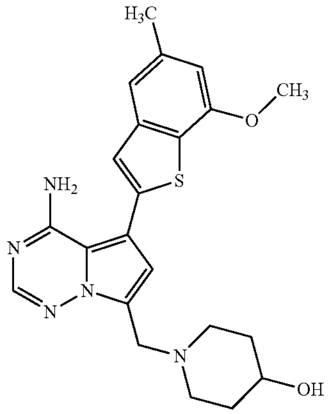 [SMILES: COc1cc(C)cc2cc(-c3cc(CN4CCC(O)CC4)n4ncnc(N)c34)sc12] | P7 or P8 | Method 6: $R_t$ = 1.39 min; MS (ESIpos): m/z = 424 $(M + H)^+$ |

TABLE II-continued
| Example No. | Structure | Purification method | LC-MS data |
|---|---|---|---|
| 89 | 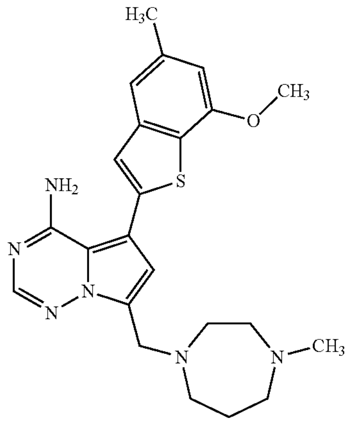 [SMILES: COc1cc(C)cc2cc(-c3cc(CN4CCCN(C)CC4)n4ncnc(N)c34)sc12] | P7 or P8 | Method 6: $R_t$ = 1.25 min; MS (ESIpos): m/z = 437 $(M + H)^+$ |
| 90 | 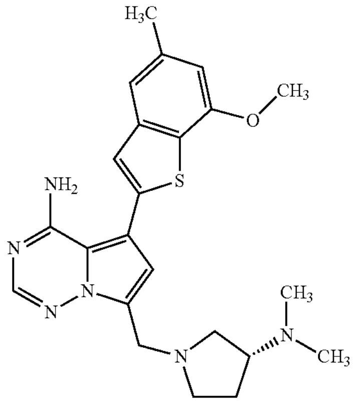 [SMILES: COc1cc(C)cc2cc(-c3cc(CN4CC[C@@H](N(C)C)C4)n4ncnc(N)c34)sc12] | P7 or P8 | Method 6: $R_t$ = 1.25 min; MS (ESIpos): m/z = 437 $(M + H)^+$ |
| 91 | 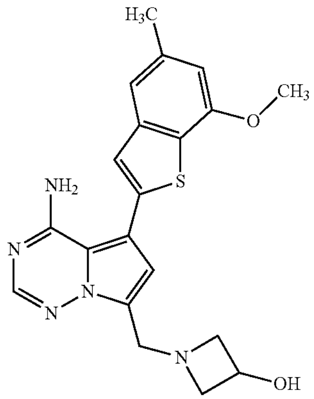 [SMILES: COc1cc(C)cc2cc(-c3cc(CN4CC(O)C4)n4ncnc(N)c34)sc12] | P7 or P8 | Method 6: $R_t$ = 1.39 min; MS (ESIpos): m/z = 396 $(M + H)^+$ |

TABLE II-continued

| Example No. | Structure | Purification method | LC-MS data |
|---|---|---|---|
| 92 | 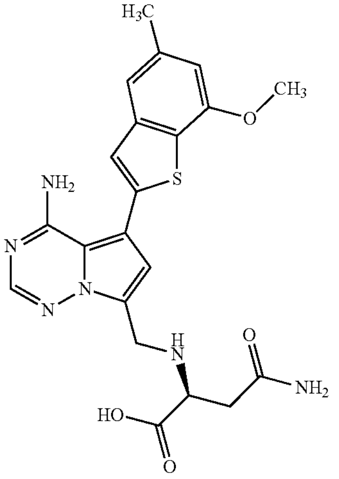 [SMILES: COc1cc(C)cc2cc(-c3cc(CN[C@@H](CC(N)=O)C(=O)O)n4ncnc(N)c34)sc12] | P7 or P8 | Method 6: $R_t$ = 1.46 min; MS (ESIpos): m/z = 455 $(M + H)^+$ |

Example 93

(4-{[4-Amino-5-(7-methoxy-5-methyl-1-benzothiophen-2-yl)pyrrolo[2,1-f][1,2,4]triazin-7-yl]-methyl}piperazin-1-yl)(cyclopropyl)methanone

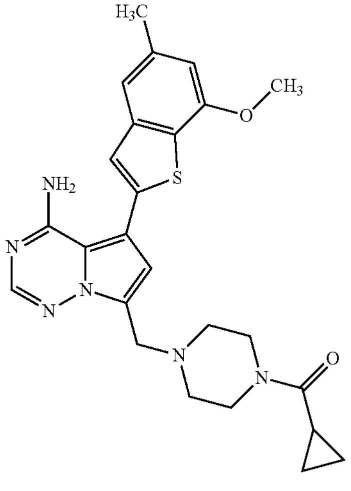 [SMILES: COc1cc(C)cc2cc(-c3cc(CN4CCN(C(=O)C5CC5)CC4)n4ncnc(N)c34)sc12]

A solution of Example 1 (100 mg, 0.187 mmol) in THF (1 ml) and dichloromethane (2 ml) was treated with cyclopropylcarbonyl chloride (33 μl, 0.373 mmol) and sodium carbonate (158 mg, 1.49 mmol). The resulting mixture was stirred at rt for 48 h. Then, the reaction mixture was filtered and the solid washed with THF. The filtrate was purified by preparative RP-HPLC (Reprosil C18, gradient 10-95% acetonitrile/0.1% aq. formic acid) to afford 9 mg (9% of th.) of the title compound.

LC-MS (method 2): $R_t$=0.83 min; MS (ESIpos): m/z=477 $(M+H)^+$.

Example 94

(4-{[4-Amino-5-(7-methoxy-5-methyl-1-benzothiophen-2-yl)pyrrolo[2,1-f][1,2,4]triazin-7-yl]-methyl}piperazin-1-yl)(cyclobutyl)methanone

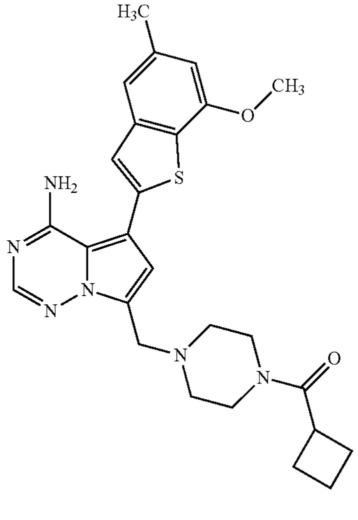 [SMILES: COc1cc(C)cc2cc(-c3cc(CN4CCN(C(=O)C5CCC5)CC4)n4ncnc(N)c34)sc12]

A solution of Example 1 (100 mg, 187 mmol) in THF (1 ml) and dichloromethane (2 ml) was treated with cyclobutylcarbonyl chloride (44 mg, 0.373 mmol) and sodium carbonate (158 mg, 1.49 mmol). The resulting mixture was stirred at rt for 48 h. Then, the reaction mixture was filtered and the solid rinsed with THF. The filtrate was purified by preparative RP-HPLC (Reprosil C18, gradient 10-95% acetonitrile/0.1% aq. formic acid) affording 52 mg (57% of th.) of the title compound.

LC-MS (method 2): $R_t$=0.79 min; MS (ESIpos): m/z=491 $(M+H)^+$ $^1$H-NMR (400 MHz, DMSO-$d_6$): inter al. δ=8.20 (s, 1H), 7.39 (s, 1H), 7.32 (s, 1H), 7.25 (s, 1H), 6.85 (s, 1H), 4.70 (s, 2H), 3.96 (s, 3H), 2.45 (s, 3H) ppm.

Example 95

4-(4-{[4-Amino-5-(7-methoxy-5-methyl-1-benzothiophen-2-yl)pyrrolo[2,1-f][1,2,4]triazin-7-yl]-methyl}piperazin-1-yl)-4-oxobutanamide dihydrochloride

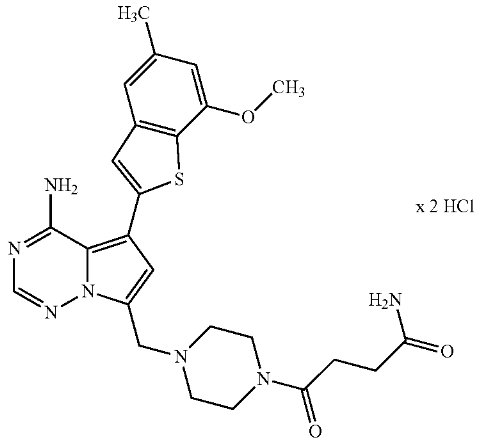 [SMILES: COc1cc(C)cc2cc(-c3cc(CN4CCN(C(=O)CCC(N)=O)CC4)n4ncnc(N)c34)sc12]

x 2 HCl

A solution of 4-amino-4-oxobutanoic acid (33 mg, 280 μmol) in THF (2 ml) was treated with TBTU (90 mg, 0.28 mmol) and N,N-diisopropylethylamine (0.154 ml, 0.933 mmol). The solution was stirred at rt for 30 min. The compound from Example 1 (100 mg, 0.187 mmol) was added, and the resulting mixture was stirred at rt for further 2.5 h. After this, the mixture was directly purified by preparative RP-HPLC (Reprosil C18, gradient acetonitrile/0.2% aq. TFA). The product fractions were diluted with 1 M hydrochloric acid and then evaporated affording 71 mg (64% of th.) of the title compound.

LC-MS (method 2): $R_t$=0.74 min; MS (ESIpos): m/z=508 $(M+H)^+$ $^1$H-NMR (400 MHz, DMSO-$d_6$): inter al. δ=8.13 (s, 1H), 7.37 (s, 1H), 7.31 (br. s, 2H), 7.14 (s, 1H), 6.84 (s, 1H), 6.75 (br. s, 1H), 4.72 (br. s, 2H), 3.96 (s, 5H), 2.45 (s, 4H) ppm.

Example 96

1-(4-{[4-Amino-5-(7-methoxy-5-methyl-1-benzothiophen-2-yl)pyrrolo[2,1-f][1,2,4]triazin-7-yl]-methyl}piperazin-1-yl)-2-hydroxyethanone

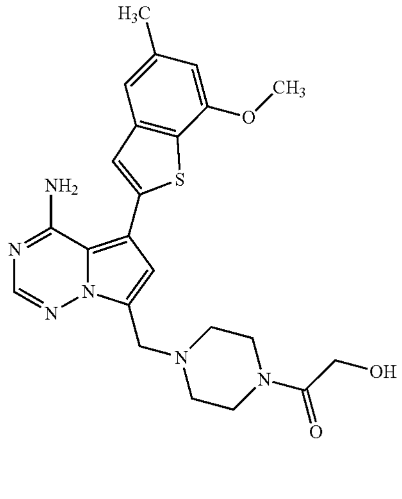 [SMILES: COc1cc(C)cc2cc(-c3cc(CN4CCN(C(=O)CO)CC4)n4ncnc(N)c34)sc12]

Step 1:

A solution of Example 1 (200 mg, 0.373 mmol) in THF (1 ml) was treated with acetoxyacetyl chloride (40 μl, 0.373 mmol) and sodium carbonate (99 mg, 0.933 mmol). The resulting mixture was stirred at rt for 16 h. Another portion of acetoxyacetyl chloride (10 μl, 0.093 mmol) was added, and stirring was continued for 1 h. The reaction was then quenched by addition of methanol and water. After 1 min stirring, the mixture was diluted with sat. aq. sodium chloride solution and extracted with ethyl acetate. The combined organic layers were dried over magnesium sulfate and evaporated affording 182 mg (90% purity) of the intermediate compound 2-(4-{[4-amino-5-(7-methoxy-5-methyl-1-benzothiophen-2-yl)pyrrolo[2,1-f][1,2,4]triazin-7-yl]methyl}piperazin-1-yl)-2-oxoethyl acetate which was used in the next step without further purification.

Step 2:

A solution of the crude intermediate compound obtained above (149 mg, 0.263 mmol, 90% purity) in THF (2 ml) was treated with 1 M aq. lithium hydroxide solution (1.46 ml, 1.46 mmol). The resulting mixture was stirred at rt for 1.5 h, then acidified with 1 M hydrochloric acid to pH 5-6 and extracted with ethyl acetate. The combined organic layers were washed with sat. aq. sodium chloride solution whereupon a solid precipitated. The solid was filtered off and washed with dichloromethane/methanol (10:1) affording 48 mg (34% of th.) of the title compound.

LC-MS (method 4): $R_t$=0.67 min; MS (ESIpos): m/z=467 $(M+H)^+$ $^1$H-NMR (400 MHz, DMSO-$d_6$): δ=7.98 (s, 1H), 7.35 (s, 1H), 7.28 (s, 1H), 6.82 (s, 1H), 6.78 (s, 1H), 4.52 (t, 1H), 4.05 (d, 2H), 3.95 (s, 3H), 3.89 (s, 2H), 3.46 (br. s, 2H), 3.31 (br. s, 2H), 2.48-2.41 (m, 7H) ppm.

Example 97

[4-Amino-5-(7-methoxy-5-methyl-1-benzothiophen-2-yl)pyrrolo[2,1-f][1,2,4]triazin-7-yl][(3S)-3-amino-3-methylpyrrolidin-1-yl]methanone dihydrochloride

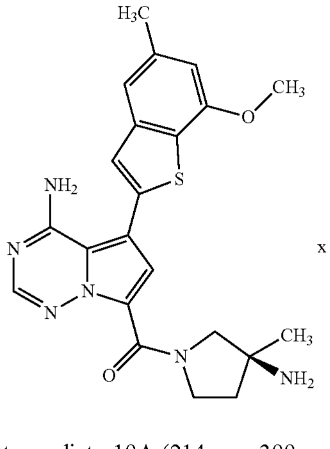

x 2 HCl

Intermediate 19A (214 mg, 399 μmol) was dissolved in 1,4-dioxane (3 ml), and a 4 M solution of hydrogen chloride in 1,4-dioxane (5 ml) was added. The mixture was stirred at rt for 5 h. After evaporation, the residue was purified by preparative RP-HPLC (Reprosil C18, gradient acetonitrile/0.2% aq. formic acid). The product thus obtained was dissolved in 1 M hydrochloric acid/1,4-dioxane (1:1) and lyophilized yielding 160 mg (75% of th.) of the title compound.

LC-MS (method 2): $R_t$=0.67 min; MS (ESIpos): m/z=437 $(M+H)^+$ $^1$H-NMR (400 MHz, methanol-$d_4$): δ=8.16 (s, 1H), 7.47 (s, 1H), 7.32 (s, 1H), 7.25 (s, 0.5H), 7.22 (s, 0.5H), 6.83 (s, 1H), 4.00 (s, 3H), 3.67-3.94 (m, 4H), 2.49 (s, 3H), 2.22-2.32 (m, 2H), 1.60 (br. s, 1.5H), 1.52 (br. s, 1.5H) ppm.

Example 98 rac-4-Amino-5-(7-methoxy-5-methyl-1-benzothiophen-2-yl)-N-(2-oxopyrrolidin-3-yl)pyrrolo-[2,1-f][1,2,4]triazine-7-carboxamide hydrochloride

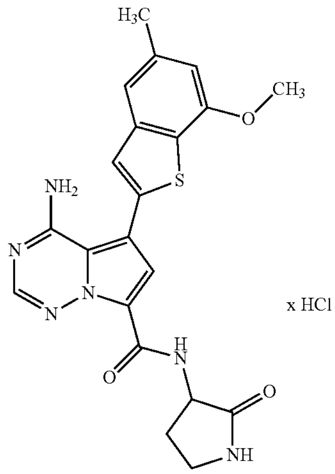 [SMILES: COc1cc(C)cc2cc(-c3cc(C(=O)NC4CCNC4=O)n4ncnc(N)c34)sc12]

x HCl

A solution of Intermediate 15A (50 mg, 141 μmol) in DMF (2 ml) was treated with TBTU (50 mg, 155 μmol) and DIPEA (61 μl, 353 μmol) and stirred at rt for 15 min (3R)-3-Aminopyrrolidin-2-one (28 mg, 282 μmol) was added, and the resulting mixture was stirred at rt for 16 h. After this, the mixture was directly purified by preparative RP-HPLC (Reprosil C18, gradient acetonitrile/0.2% aq. TFA). The product fractions were combined, diluted with 1 M hydrochloric acid and evaporated affording 34 mg (50% of th.) of the title compound.

LC-MS (method 2): $R_t$=0.85 min; MS (ESIpos): m/z=437 $(M+H)^+$ $^1$H-NMR (400 MHz, DMSO-$d_6$): inter alia δ=9.21-9.28 (m, 1H), 8.58 (br. s, 1H), 8.24 (s, 1H), 8.02 (s, 1H), 7.42 (s, 1H), 7.28-7.35 (m, 2H), 6.84 (s, 1H), 3.96 (s, 3H), 3.23-3.31 (m, 2H), 2.45 (s, 3H), 1.90-2.05 (m, 1H) ppm.

Example 99

[4-Amino-5-(7-methoxy-5-methyl-1-benzothiophen-2-yl)pyrrolo[2,1-f][1,2,4]triazin-7-yl]-(piperazin-1-yl)methanone dihydrochloride

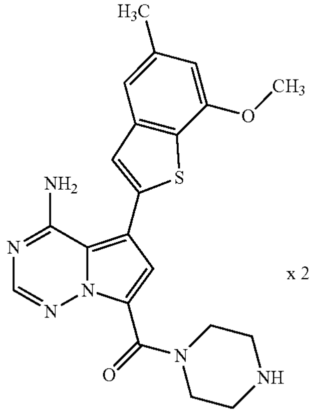

x 2 HCl

A solution of Intermediate 15A (100 mg, purity 89%, 251 μmol) in DMF (2 ml) was treated with TBTU (87 mg, 276 μmol) and DIPEA (109 μl, 628 μmol) and stirred at rt for 15 min. tert-Butyl piperazine-1-carboxylate (94 mg, 502 μmol) was added, and the resulting mixture was stirred at rt for 16 h. After this, the mixture was directly purified by preparative RP-HPLC (Reprosil C18, gradient acetonitrile/0.2% aq. TFA). The product fractions were combined, diluted with 1 M hydrochloric acid and evaporated affording 90 mg (73% of th.) of the title compound.

LC-MS (method 2): $R_t$=0.67 min; MS (ESIpos): m/z=422 $(M+H)^+$ $^1$H-NMR (400 MHz, methanol-$d_4$): inter alia δ=8.18 (s, 1H), 7.47 (s, 1H), 7.32 (s, 1H), 7.22 (s, 1H), 6.83 (s, 1H), 4.00 (s, 3H), 3.60-3.84 (m, 2H), 3.35 (m, 4H) ppm.

General Procedure for the Preparation of Examples 100-105 in Table III:

A 0.19 M solution of Intermediate 15A in DMF was treated with 1.1 eq. of TBTU and 2.5 eq. of DIPEA and stirred at rt for 15 min. The appropriate amine (1.1-2.0 eq.) was added, and the resulting mixture was stirred at rt overnight. After evaporation, the crude product was dissolved in DMSO and purified according to the methods indicated.

For the synthesis of Examples 104 and 105, the appropriate amine component was protected at the primary amino group with a tert-butoxycarbonyl (Boc) group, which was cleaved after the purification by treatment with a 4 M solution of hydrogen chloride in 1,4-dioxane (stirring at rt for 2 h). Evaporation of the volatiles and drying in vacuo afforded the final products.

TABLE III
| Example No. | Structure | Purification method(s) | LC-MS data |
|---|---|---|---|
| 100 | 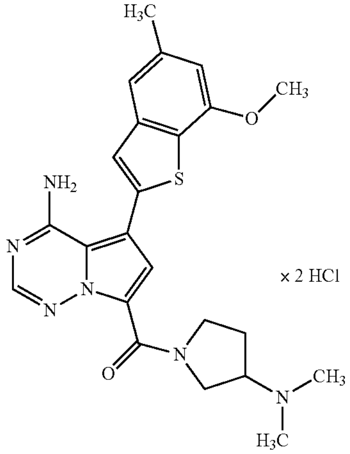 [SMILES: COc1cc(C)cc2cc(-c3cc(C(=O)N4CCC(N(C)C)C4)n4ncnc(N)c34)sc12] × 2 HCl | P3; P4 | Method 2: $R_t$ = 0.67 min; MS (ESIpos): m/z = 451 $(M + H)^+$ |
| 101 | 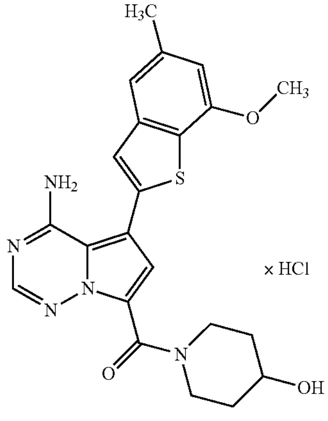 [SMILES: COc1cc(C)cc2cc(-c3cc(C(=O)N4CCC(O)CC4)n4ncnc(N)c34)sc12] × HCl | P3; P4 | Method 2: $R_t$ = 0.82 min; MS (ESIpos): m/z = 438 $(M + H)^+$ |
| 102 | 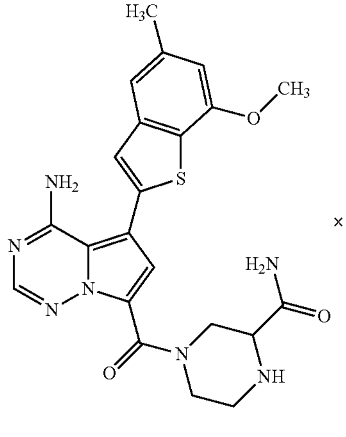 × 2 HCl | P2; P4 | Method 2: $R_t$ = 0.66 min; MS (ESIpos): m/z = 466 $(M + H)^+$ |

TABLE III-continued
| Example No. | Structure | | Purification method(s) | LC-MS data |
|---|---|---|---|---|
| 103 | 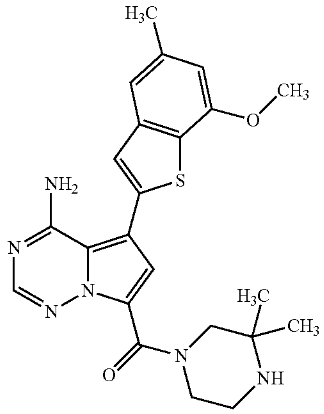 | × 2 HCl | P3; P4 | Method 2: $R_t$ = 0.71 min; MS (ESIpos): m/z = 451 $(M + H)^+$ |
| 104 | 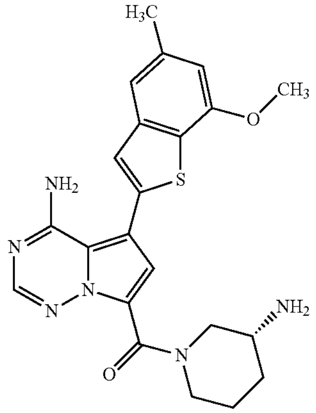 | × 2 HCl | P3 | Method 4: $R_t$ = 0.65 min; MS (ESIpos): m/z = 437 $(M + H)^+$ |
| 105 | 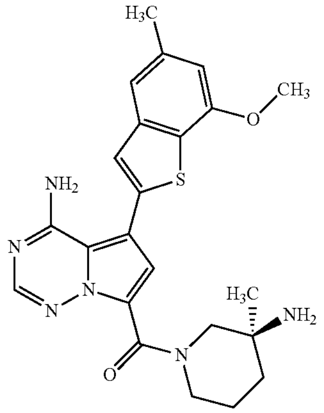 [SMILES: COc1cc(C)cc2cc(-c3cc(C(=O)N4CCC[C@](C)(N)C4)n4ncnc(N)c34)sc12] | | P3; P6 (after Boc-cleavage) | Method 4: $R_t$ = 0.67 min; MS (ESIpos): m/z = 451 $(M + H)^+$ |

Example 106

N-{[4-Amino-5-(7-methoxy-5-methyl-1-benzothiophen-2-yl)pyrrolo[2,1-f][1,2,4]triazin-7-yl]-methyl}glycinamide dihydrochloride

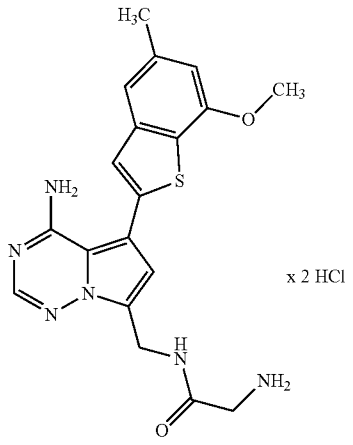 [SMILES: COc1cc(C)cc2cc(-c3cc(CNC(=O)CN)n4ncnc(N)c34)sc12]

Intermediate 20A (4.8 mg, 10 μmol) was stirred in a 4 M solution of hydrogen chloride in 1,4-dioxane (0.5 ml) at rt for 1 h. The mixture was then evaporated and the residue triturated with acetone. The resulting solid was filtered off and dried in vacuo yielding 4.2 mg (93% of th.) of the title compound.

LC-MS (method 5): $R_t$=1.66 min; MS (ESIpos): m/z=397 $(M+H)^+$ $^1$H-NMR (400 MHz, DMSO-$d_6$): δ=9.02 (br. s, 1H), 8.16 (m, 4H), 7.38 (s, 1H), 7.30 (s, 1H), 6.91 (s, 1H), 6.84 (s, 1H), 4.65 (br. s, 2H), 3.96 (s, 3H), 3.63 (br. s, 2H), 2.44 (s, 3H) ppm.

Example 107

5-(7-Methoxy-5-methyl-1-benzothiophen-2-yl)-7-{[2-(pyrrolidin-1-yl)ethoxy]methyl}pyrrolo-[2,1-f][1,2,4]triazin-4-amine hydrochloride

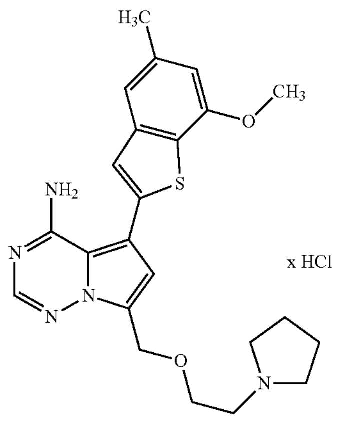 [SMILES: COc1cc(C)cc2cc(-c3cc(COCCN4CCCC4)n4ncnc(N)c34)sc12]

A suspension of Intermediate 12A (30 mg, 0.08 mmol), 2-(pyrrolidin-1-yl)ethanol (193 mg, 1.67 mmol) and N,N,N-trimethylhexadecan-1-ammonium bromide (6 mg, 0.02 mmol) in dichloromethane (3 ml) was stirred at rt for 1 h 45 min. DMF (2 ml) was added, and the solution was concentrated under reduced pressure to evaporate the dichloromethane solvent. The residual mixture was purified by preparative RP-HPLC (Reprosil C18, gradient acetonitrile/0.2% aq. TFA). The product fractions were combined, diluted with 1 M hydrochloric acid and evaporated to dryness yielding 5.3 mg (13% of th.) of the title compound.

LC-MS (method 4): $R_t$=0.69 min; MS (ESIpos): m/z=438 $(M+H)^+$ $^1$H-NMR (400 MHz, DMSO-$d_6$): δ=8.13 (s, 1H), 7.40 (s, 1H), 7.32 (s, 1H), 7.24 (s, 1H), 6.85 (s, 1H), 4.98 (s, 2H), 3.90-4.06 (m, 5H), 3.34-3.47 (m, 2H), 2.44 (t, 3H), 2.01-2.22 (m, 4H) ppm.

Example 108

7-{[2-(Dimethylamino)ethoxy]methyl}-5-(7-methoxy-5-methyl-1-benzothiophen-2-yl)pyrrolo-[2,1-f][1,2,4]triazin-4-amine dihydrochloride

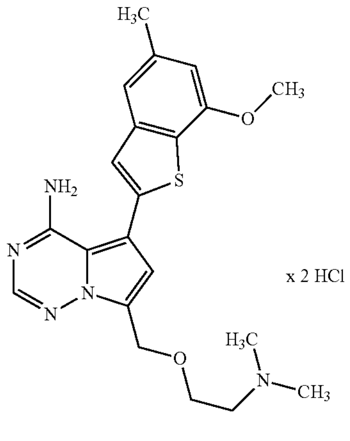 [SMILES: COc1cc(C)cc2cc(-c3cc(COCCN(C)C)n4ncnc(N)c34)sc12]

A suspension of Intermediate 12A (53 mg, 147 μmol), 2-(dimethylamino)ethanol (26 mg, 294 μmol) and DIPEA (97 μl, 588 μmol) in THF (3 ml) was stirred at rt for 20 h. Methanol (2 ml) was added, and the solution was purified by preparative RP-HPLC (Reprosil C18, gradient acetonitrile/0.2% aq. TFA). The product fractions were combined, diluted with 1 M hydrochloric acid and evaporated to dryness yielding 30 mg (41% of th.) of the title compound.

LC-MS (method 4): $R_t$=0.65 min; MS (ESIpos): m/z=412 $(M+H)^+$ $^1$H-NMR (400 MHz, DMSO-$d_6$): δ=8.16 (s, 1H), 7.41 (s, 1H), 7.32 (s, 1H), 7.22 (s, 1H), 6.83 (s, 1H), 4.97 (s, 2H), 3.96 (s, 5H), 3.40-3.53 (m, 2H), 2.45 (s, 3H) ppm.

General Procedure for the Preparation of Examples 109-120 in Table IV:

A solution of Intermediate 12A (0.1 mmol) in 1,2-dichloroethane (0.6 ml) was treated with 10 eq. of the appropriate alcohol and irradiated in a microwave oven at 120° C. for 1 hour. After evaporation, the crude product was dissolved in DMSO and purified according to the methods indicated.

In cases where the alcohol component carried a tert-butoxycarbonyl-protected amino group, the crude protected intermediate obtained after evaporation of the reaction mixture (see above) was treated with a 1:3-mixture of dichloromethane and trifluoroacetic acid and shaken overnight at rt. The mixture was then evaporated again, and the crude product was dissolved in DMSO and purified according to the methods indicated.

TABLE IV
| Example No. | Structure | Purification method | LC-MS data |
| --- | --- | --- | --- |
| 109 | 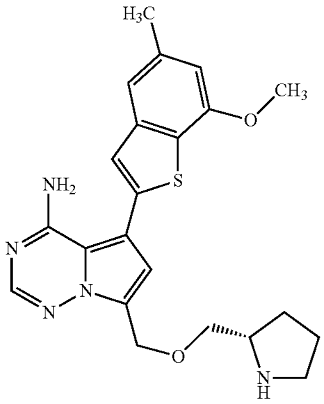 [SMILES: COc1cc(C)cc2cc(-c3cc(COC[C@@H]4CCCN4)n4ncnc(N)c34)sc12] | P7 or P8 | Method 7: $R_t$ = 0.86 min; MS (ESIpos): m/z = 424 $(M + H)^+$ |
| 110 | 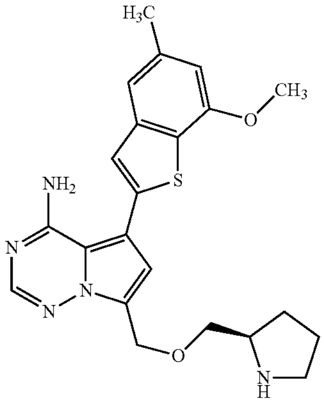 [SMILES: COc1cc(C)cc2cc(-c3cc(COC[C@H]4CCCN4)n4ncnc(N)c34)sc12] | P7 or P8 | Method 7: $R_t$ = 0.86 min; MS (ESIpos): m/z = 424 $(M + H)^+$ |
| 111 | 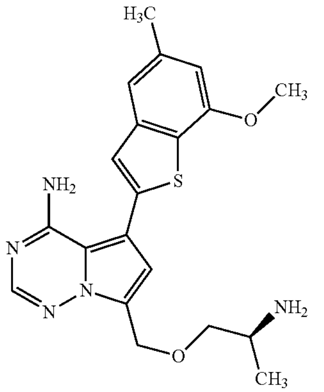 [SMILES: COc1cc(C)cc2cc(-c3cc(COC[C@H](C)N)n4ncnc(N)c34)sc12] | P7 or P8 | Method 7: $R_t$ = 0.83 min; MS (ESIpos): m/z = 398 $(M + H)^+$ |

TABLE IV-continued
| Example No. | Structure | Purification method | LC-MS data |
| --- | --- | --- | --- |
| 112 | 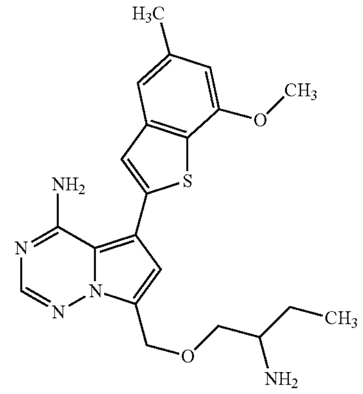 [SMILES: CCC(N)COCc1cc(-c2cc3cc(C)cc(OC)c3s2)c2c(N)ncnn12] | P7 or P8 | Method 7: $R_t$ = 0.86 min; MS (ESIpos): m/z = 412 $(M + H)^+$ |
| 113 | 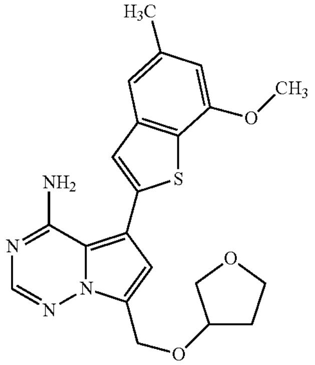 [SMILES: COc1cc(C)cc2cc(-c3cc(COC4CCOC4)n4ncnc(N)c34)sc12] | P7 or P8 | Method 7: $R_t$ = 1.24 min; MS (ESIpos): m/z = 411 $(M + H)^+$ |
| 114 | 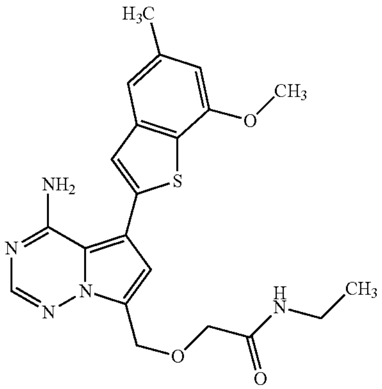 [SMILES: CCNC(=O)COCc1cc(-c2cc3cc(C)cc(OC)c3s2)c2c(N)ncnn12] | P7 or P8 | Method 7: $R_t$ = 1.20 min; MS (ESIpos): m/z = 426 $(M + H)^+$ |
| 115 | 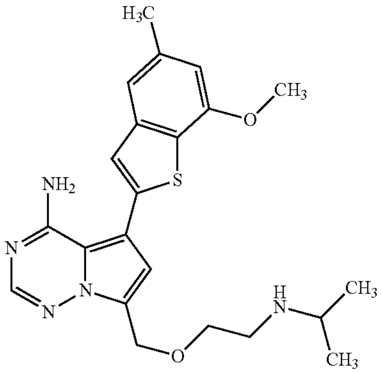 [SMILES: COc1cc(C)cc2cc(-c3cc(COCCNC(C)C)n4ncnc(N)c34)sc12] | P7 or P8 | Method 7: $R_t$ = 0.86 min; MS (ESIpos): m/z = 426 $(M + H)^+$ |

TABLE IV-continued
| Example No. | Structure | Purification method | LC-MS data |
|---|---|---|---|
| 116 | 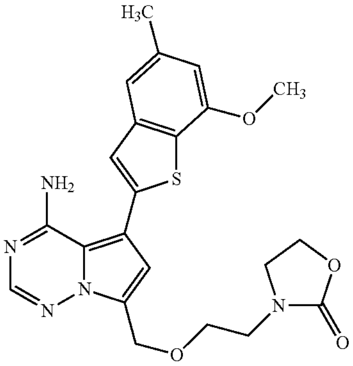 [SMILES: COc1cc(C)cc2cc(-c3cc(COCCN4CCOC4=O)n4ncnc(N)c34)sc12] | P7 or P8 | Method 7: $R_t$ = 1.16 min; MS (ESIpos): m/z = 454 (M + H)$^+$ |
| 117 | 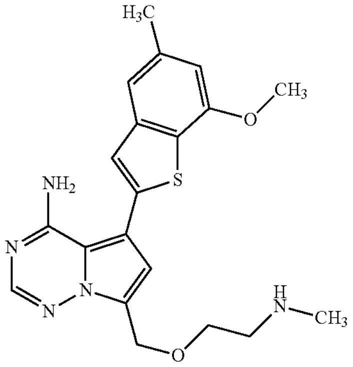 [SMILES: CNCCOCc1cc(-c2cc3cc(C)cc(OC)c3s2)c2c(N)ncnn12] | P7 or P8 | Method 7: $R_t$ = 0.82 min; MS (ESIpos): m/z = 398 (M + H)$^+$ |
| 118 | 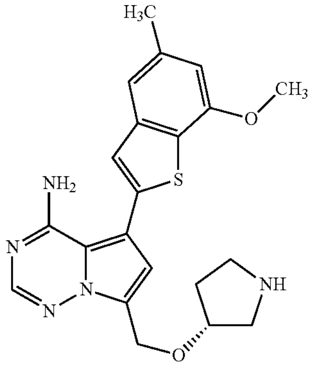 [SMILES: COc1cc(C)cc2cc(-c3cc(CO[C@@H]4CCNC4)n4ncnc(N)c34)sc12] | P7 or P8 | Method 7: $R_t$ = 0.83 min; MS (ESIpos): m/z = 410 (M + H)$^+$ |
| 119 | 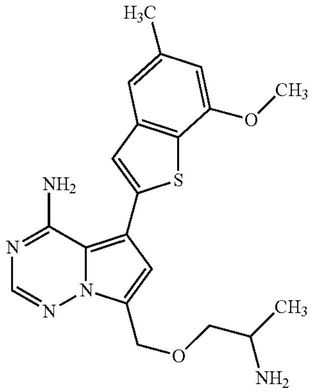 [SMILES: COc1cc(C)cc2cc(-c3cc(COCC(C)N)n4ncnc(N)c34)sc12] | P7 or P8 | Method 7: $R_t$ = 0.83 min; MS (ESIpos): m/z = 398 (M + H)$^+$ |

TABLE IV-continued

| Example No. | Structure | Purification method | LC-MS data |
|---|---|---|---|
| 120 | 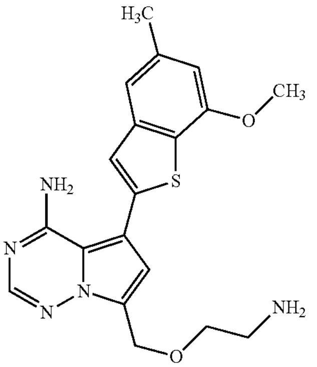 [SMILES: COc1cc(C)cc2cc(-c3cc(COCCN)n4ncnc(N)c34)sc12] | P7 or P8 | Method 7: $R_t$ = 0.78 min; MS (ESIpos): m/z = 384 (M + H)$^+$ |

General Procedure for the Preparation of Examples 121-123 in Table V:

A solution of Intermediate 12A (0.1 mmol) in 1,2-dichloroethane (0.6 ml) was treated with 10 eq. of the appropriate imidazole derivative and shaken overnight at rt. After evaporation, the crude product was dissolved in DMSO and purified according to the methods indicated.

TABLE V

| Example No. | Structure | Purification method | LC-MS data |
|---|---|---|---|
| 121 | 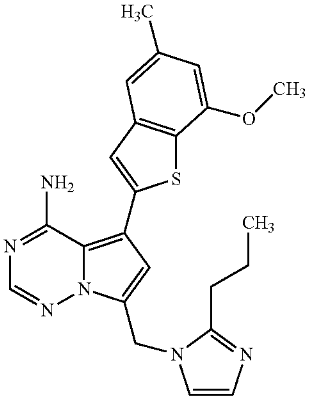 [SMILES: CCCc1nccn1Cc1cc(-c2cc3cc(C)cc(OC)c3s2)c2c(N)ncnn12] | P7 or P8 | Method 7: $R_t$ = 0.91 min; MS (ESIpos): m/z = 433 (M + H)$^+$ |
| 122 | 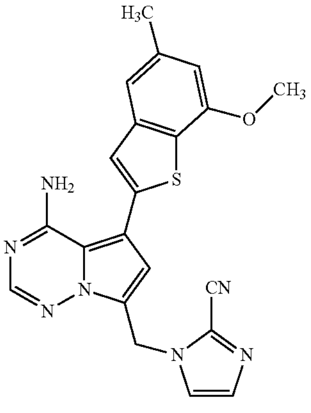 [SMILES: COc1cc(C)cc2cc(-c3cc(Cn4ccnc4C#N)n4ncnc(N)c34)sc12] | P7 or P8 | Method 7: $R_t$ = 1.25 min; MS (ESIpos): m/z = 416 (M + H)$^+$ |

TABLE V-continued

| Example No. | Structure | Purification method | LC-MS data |
|---|---|---|---|
| 123 | 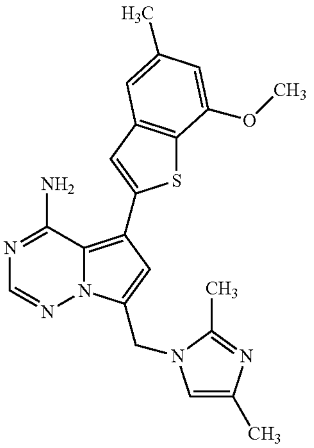 [SMILES: COc1cc(C)cc2cc(-c3cc(Cn4cc(C)nc4C)n4ncnc(N)c34)sc12] | P7 or P8 | Method 7: $R_t$ = 0.88 min; MS (ESIpos): m/z = 419 (M + H)$^+$ |

B. EVALUATION OF BIOLOGICAL ACTIVITY

Abbreviations and Acronyms

Ahx 6-aminohexanoic acid
ATP adenosine triphosphate
BSA bovine serum albumin
CREB cAMP-response element-binding protein
DMSO dimethylsulfoxide
EDTA ethylenediaminetetraacetic acid
EGTA ethyleneglycol-bis(2-aminoethylether)-N,N,N',N'-tetraacetic acid
FBS fetal bovine serum
FGF fibroblast growth factor
FGFR fibroblast growth factor receptor
GFP green fluorescent protein
GST glutathione S-transferase
HEPES 4-(2-hydroxyethyl)piperazine-1-ethansulfonic acid
HRTF homogeneous time-resolved fluorescence
MOPS 3-(N-morpholino)propanesulfonic acid
mTOR mammalian target of Rapamycin
PBS phosphate buffered saline PI3K phosphatidylinositol 3-kinase RTK receptor tyrosine kinase SNP single nucleotide polymorphism TR-FRET time-resolved fluorescence resonance energy transfer VEGF vascular endothelial growth factor VEGFR vascular endothelial growth factor receptor Demonstration of the activity of the compounds of the present invention may be accomplished through in vitro, ex vivo, and in vivo assays that are well known in the art. For example, to demonstrate the activity of the compounds of the present invention, the following assays may be used.

B-1. FGFR-1 High ATP Kinase Assay

FGFR-1 inhibitory activity at high ATP concentration of the compounds of the present invention after their pre-incubation with FGFR-1 was quantified employing the TR-FRET based FGFR-1 high ATP assay as described in the following paragraphs:

A recombinant tagged FGFR-1 fusion protein [fusion of glutathione-S-transferase (GST) (N-terminally), His6-tag, thrombin cleavage site, and the intracellular part of human FGFR-1 from amino acids G400 to R800 as in GenBank entry NM_015850], expressed in SF9 insect cells using baculovirus expression system and purified via glutathione-agarose affinity chromatography, was purchased from Proqinase (product no. 0101-0000-1) and used as enzyme. As substrate for the kinase reaction, the biotinylated peptide biotin-Ahx-AAEEEYFFLFAKKK (C-terminus in amide form) was used which can be purchased, e.g., from Biosyntan (Berlin-Buch, Germany).

Usually, test compounds were tested on the same microtiter plate at 11 different concentrations in the range of 20 μM to 0.1 nM (e.g. 20 μM, 5.9 μM, 1.7 μM, 0.51 μM, 0.15 μM, 44 nM, 13 nM, 3.8 nM, 1.1 nM, 0.33 nM, and 0.1 nM) in duplicates for each concentration. The dilution series was prepared separately prior to the assay as 100-fold concentrated stock solutions in DMSO; exact concentrations could vary depending on the pipettor used. For the assay, 50 nl of each stock solution of the test compound in DMSO was pipetted into a black, low-volume 384-well microtiter plate (Greiner Bio-One, Frickenhausen, Germany). 2 μl of a solution of the above FGFR-1 fusion protein in aqueous assay buffer [8 mM MOPS pH 7.0, 10 mM magnesium acetate, 1.0 mM dithiothreitol, 0.05% (w/v) bovine serum albumin (BSA), 0.07% (v/v) Tween-20, 0.2 mM EDTA] was added, and the mixture was incubated for 15 min at 22° C. to allow pre-binding of the test compound to the enzyme. Then, the kinase reaction was started by the addition of 3 μl of a solution of adenosine triphosphate (ATP, 3.3 mM; final concentration in the 5 μl assay volume=2 mM) and substrate (0.16 μM; final concentration in the 5 μl assay volume=0.1 μM) in assay buffer, and the resulting mixture was incubated for a reaction time of 15 min at 22° C. The concentration of FGFR-1 fusion protein was adjusted depending on the activity of the enzyme lot and was chosen appropriately to have the assay in the linear range (typical concentrations were in the range of 0.05 μg/ml). The reaction was stopped by the addition of 5 μl of a solution of HTRF detection reagents [25 nM streptavidin-XL665 (Cis Biointernational) and 1 nM PT66-Eu-chelate, an europium-chelate labelled anti-phosphotyrosine antibody (Perkin-Elmer; PT66-Tb-cryptate from Cis Biointernational may be used instead), in an aqueous EDTA solution (50 mM EDTA, 0.1% (w/v) BSA in 50 mM HEPES/NaOH pH 7.5)].

The resulting mixture was incubated for 1 h at 22° C. to allow formation of the complex between the phosphorylated biotinylated peptide and the detection reagents. Subsequently, the amount of phosphorylated substrate was evaluated by measurement of the resonance energy transfer from the Eu-chelate to the streptavidin-XL665. For this, the fluorescence emissions at 620 nm and 665 nm after excitation at 350 nm were measured in a TR-FRET reader [e.g. Rubystar (BMG Labtechnologies, Offenburg, Germany) or Viewlux (Perkin-Elmer)]. The ratio of the emissions at 665 nm and at 620 nm was taken as the measure for the amount of phosphorylated substrate. Data were normalised (enzyme reaction without inhibitor=0% inhibition, all other assay components but no enzyme=100% inhibition), and $IC_{50}$ values were calculated by a 4-parameter fit using an in-house software.

$IC_{50}$ values for individual compounds of the invention from this assay are listed in Table 1A below:

TABLE 1A

| Example No. | FGFR-1 (high ATP) $IC_{50}$ [nM] |
|---|---|
| 1 | 9.9 |
| 2 | 20.1 |
| 3 | 92.8 |
| 4 | 34.7 |
| 5 | 1.1 |
| 6 | 20.1 |
| 7 | 7.8 |
| 8 | 29.0 |
| 9 | 4.7 |
| 10 | 94.9 |
| 11 | 95.0 |
| 12 | 39.1 |
| 13 | 93.6 |
| 14 | 43.6 |
| 15 | 11.1 |
| 16 | 15.6 |
| 17 | 27.3 |
| 18 | 26.4 |
| 19 | 14.7 |
| 20 | 54.7 |
| 21 | 13.2 |
| 22 | 9.3 |
| 23 | 19.3 |
| 24 | 34.1 |
| 25 | 73.3 |
| 26 | 82.6 |
| 27 | 42.2 |
| 28 | 83.2 |
| 29 | 50.4 |
| 30 | 54.2 |
| 31 | 54.6 |
| 32 | 23.3 |
| 33 | 68.9 |
| 34 | 99.3 |
| 35 | 16.4 |
| 36 | 17.0 |
| 37 | 44.9 |
| 38 | 45.7 |
| 39 | 57.1 |
| 40 | 63.8 |
| 41 | 7.3 |
| 42 | 13.4 |
| 43 | 50.6 |
| 44 | 38.8 |
| 45 | 18.1 |
| 46 | 20.8 |
| 47 | 25.2 |
| 48 | 28.9 |
| 49 | 58.9 |
| 50 | 59.3 |
| 51 | 41.3 |
| 52 | 87.8 |
| 53 | 94.1 |
| 54 | 7.9 |
| 55 | 16.2 |
| 56 | 17.5 |
| 57 | 32.5 |

TABLE 1A-continued

| Example No. | FGFR-1 (high ATP) $IC_{50}$ [nM] |
|---|---|
| 58 | 36.2 |
| 59 | 39.4 |
| 60 | 39.6 |
| 61 | 39.7 |
| 62 | 46.1 |
| 63 | 47.6 |
| 64 | 48.9 |
| 65 | 49.1 |
| 66 | 49.6 |
| 67 | 53.1 |
| 68 | 55.0 |
| 69 | 59.5 |
| 70 | 62.0 |
| 71 | 63.4 |
| 72 | 65.0 |
| 73 | 66.6 |
| 74 | 68.3 |
| 75 | 74.3 |
| 76 | 83.0 |
| 77 | 84.1 |
| 78 | 86.6 |
| 79 | 93.0 |
| 80 | 93.4 |
| 81 | 93.4 |
| 82 | 97.3 |
| 83 | 98.6 |
| 84 | 38.9 |
| 85 | 45.4 |
| 86 | 4.6 |
| 87 | 13.2 |
| 88 | 15.7 |
| 89 | 24.9 |
| 90 | 26.0 |
| 91 | 36.9 |
| 92 | 46.2 |
| 93 | 67.0 |
| 94 | 68.1 |
| 95 | 95.7 |
| 96 | 12.6 |
| 97 | 4.7 |
| 98 | 9.0 |
| 99 | 90.4 |
| 100 | 20.7 |
| 101 | 29.8 |
| 102 | 48.8 |
| 103 | 51.7 |
| 104 | 28.1 |
| 105 | 20.4 |
| 106 | 25.4 |
| 107 | 57.3 |
| 108 | 97.6 |
| 109 | 65.6 |
| 110 | 51.6 |
| 111 | 82.2 |
| 112 | 67.2 |
| 113 | 83.1 |
| 114 | 65.3 |
| 115 | 78.6 |
| 116 | 90.3 |
| 117 | 36.1 |
| 118 | 26.1 |
| 119 | 26.7 |
| 120 | 50.8 |
| 121 | 33.3 |
| 122 | 71.8 |
| 123 | 28.3 |

Selected 8-amino-1-(benzothiophen-2-yl)imidazo[1,5-a]pyrazine derivatives and related compounds which were regarded to be representative of closest prior art (see Int. Pat. Appl. WO 2007/061737-A2 and example compounds described therein) were synthesized following the published procedures and also tested in the FGFR-1 high ATP assay for comparative purposes. $IC_{50}$ values that were obtained for these compounds are listed in Table 1B below:

TABLE 1B

| Structure of comparative compound | Example No. in WO 2007/061737 | FGFR-1 (high ATP) $IC_{50}$ [nM] |
|---|---|---|
| 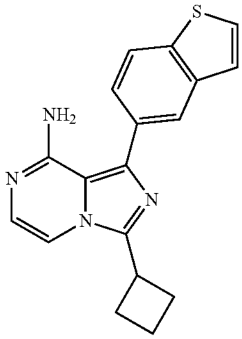 [SMILES: Nc1nccn2c(C3CCC3)nc(-c3ccc4sccc4c3)c12] | 4 | 12000 |
| 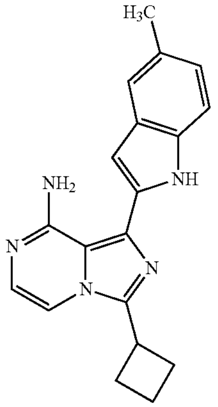 [SMILES: Cc1ccc2[nH]c(-c3nc(C4CCC4)n4ccnc(N)c34)cc2c1] | 5 | 500 |
| 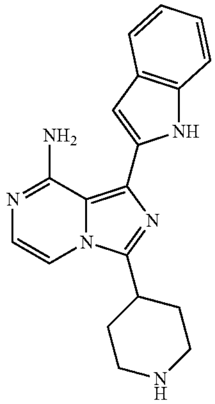 × 2 HCl | 25 | 880 |
| 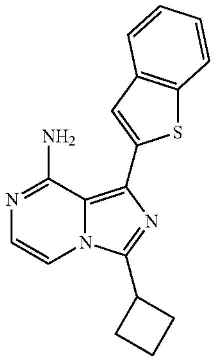 [SMILES: Nc1nccn2c(C3CCC3)nc(-c3cc4ccccc4s3)c12] | 120 | 985 |

TABLE 1B-continued

| Structure of comparative compound | Example No. in WO 2007/061737 | FGFR-1 (high ATP) $IC_{50}$ [nM] |
|---|---|---|
| 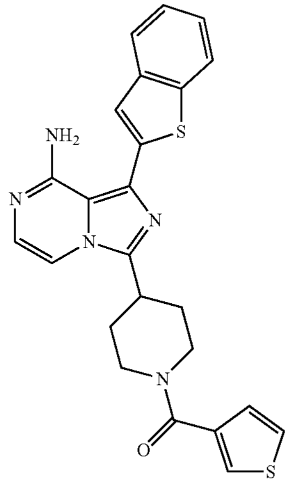 [SMILES: Nc1nccn2c(C3CCN(C(=O)c4ccsc4)CC3)nc(-c3cc4ccccc4s3)c12] | 157 | 3000 |
| 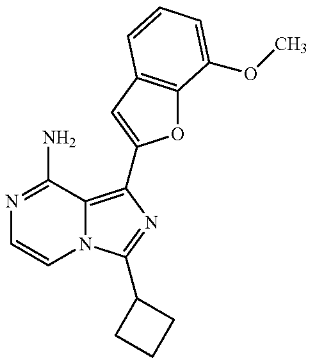 [SMILES: COc1cccc2cc(-c3nc(C4CCC4)n4ccnc(N)c34)oc12] | 205 | 20000 |
| 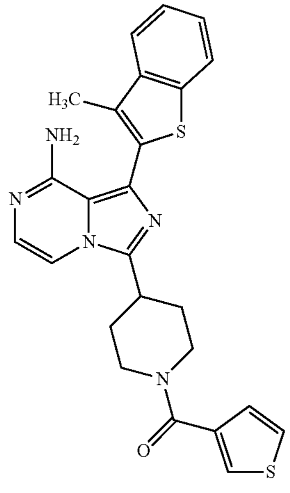 [SMILES: Cc1c(-c2nc(C3CCN(C(=O)c4ccsc4)CC3)n3ccnc(N)c23)sc2ccccc12] | 209 | 2800 |

TABLE 1B-continued

| Structure of comparative compound | Example No. in WO 2007/061737 | FGFR-1 (high ATP) $IC_{50}$ [nM] |
|---|---|---|
| 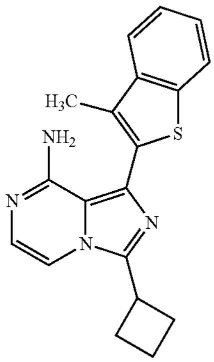 [SMILES: Cc1c(-c2nc(C3CCC3)n3ccnc(N)c23)sc2ccccc12] | 210 | 456 |
| 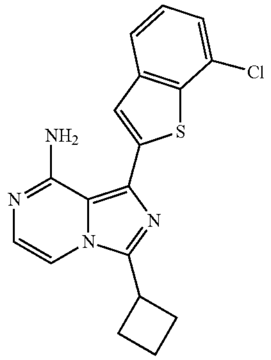 [SMILES: Nc1nccn2c(C3CCC3)nc(-c3cc4cccc(Cl)c4s3)c12] | 233 | 4600 |

The $IC_{50}$ values specified in Table 1A and 1B demonstrate that the compounds of the present invention are about five to five hundred times more potent in inhibiting FGFR-1 kinase activity than the selected prior art compounds.

B-2. FGFR-3 Kinase Assay

FGFR-3 inhibitory activity of the compounds of the present invention after their pre-incubation with FGFR-3 was quantified employing the TR-FRET based FGFR-3 assay as described in the following paragraphs:

A recombinant tagged FGFR-3 fusion protein [fusion of glutathione-S-transferase (GST) (N-terminally), His6-tag, thrombin cleavage site, and the intracellular part of human FGFR-3 from amino acids R397 to T806 as in NCBI/Protein entry NP_000133.1], expressed in SF9 insect cells using baculovirus expression system and purified via glutathione-S-transferase affinity chromatography, was purchased from Proqinase (product no. 1068-0000-1) and used as enzyme. As substrate for the kinase reaction, the biotinylated peptide biotin-Ahx-AAEEEYFFLFAKKK (C-terminus in amide form) was used which can be purchased, e.g., from Biosyntan (Berlin-Buch, Germany).

Usually, test compounds were tested on the same microtiter plate at 11 different concentrations in the range of 20 μM to 0.1 nM (e.g. 20 μM, 5.9 μM, 1.7 μM, 0.51 μM, 0.15 μM, 44 nM, 13 nM, 3.8 nM, 1.1 nM, 0.33 nM, and 0.1 nM) in duplicates for each concentration. The dilution series was prepared separately prior to the assay as 100-fold concentrated stock solutions in DMSO; exact concentrations could vary depending on the pipettor used. For the assay, 50 nl of each stock solution of the test compound in DMSO was pipetted into a black, low-volume 384-well microtiter plate (Greiner Bio-One, Frickenhausen, Germany). 2 μl of a solution of the above FGFR-3 fusion protein in aqueous assay buffer [8 mM MOPS pH 7.0, 10 mM magnesium acetate, 1.0 mM dithiothreitol, 0.05% (w/v) bovine serum albumin (BSA), 0.07% (v/v) Tween-20, 0.2 mM EDTA] was added, and the mixture was incubated for 15 min at 22° C. to allow pre-binding of the test compound to the enzyme. Then, the kinase reaction was started by the addition of 3 µl of a solution of adenosine triphosphate (ATP, 16.7 µM; final concentration in the 5 µl assay volume=10 µM) and substrate (0.8 µM; final concentration in the 5 µl assay volume=0.5 µM) in assay buffer, and the resulting mixture was incubated for a reaction time of 60 min at 22° C. The concentration of FGFR-3 fusion protein was adjusted depending on the activity of the enzyme lot and was chosen appropriately to have the assay in the linear range (typical concentrations were in the range of 0.03 µg/ml). The reaction was stopped by the addition of 5 µl of a solution of HTRF detection reagents [100 nM streptavidin-XL665 (Cis Biointernational) and 1 nM PT66-Tb-cryptate, a terbium-cryptate labelled anti-phosphotyrosine antibody (Cis Biointernational; PT66-Eu-chelate from Perkin-Elmer may be used instead), in an aqueous EDTA solution (50 mM EDTA, 0.1% (w/v) BSA in 50 mM HEPES/NaOH pH 7.5)].

The resulting mixture was incubated for 1 h at 22° C. to allow formation of the complex between the phosphorylated biotinylated peptide and the detection reagents. Subsequently, the amount of phosphorylated substrate was evaluated by measurement of the resonance energy transfer from the Tb-chelate to the streptavidin-XL665. For this, the fluorescence emissions at 620 nm and 665 nm after excitation at 350 nm were measured in a TR-FRET reader [e.g. Rubystar (BMG Labtechnologies, Offenburg, Germany) or Viewlux (Perkin-Elmer)]. The ratio of the emissions at 665 nm and at 620 nm was taken as the measure for the amount of phosphorylated substrate. Data were normalised (enzyme reaction without inhibitor=0% inhibition, all other assay components but no enzyme=100% inhibition), and $IC_{50}$ values were calculated by a 4-parameter fit using an in-house software.

$IC_{50}$ values for individual compounds of the invention from this assay are listed in Table 2A below:

TABLE 2A

| Example No. | FGFR-3 $IC_{50}$ [nM] |
|---|---|
| 4 | 79.0 |
| 5 | 7.4 |
| 6 | 21.7 |
| 9 | 7.4 |
| 10 | 77.7 |
| 11 | 145.9 |
| 14 | 33.4 |
| 15 | 23.0 |
| 16 | 15.5 |
| 17 | 36.9 |
| 18 | 7.8 |
| 19 | 27.2 |
| 20 | 24.8 |
| 21 | 8.0 |
| 22 | 41.8 |
| 23 | 69.4 |
| 24 | 118.5 |
| 26 | 130.3 |
| 27 | 60.8 |
| 28 | 63.7 |
| 53 | 145.2 |
| 54 | 15.8 |
| 55 | 18.7 |
| 56 | 22.6 |

TABLE 2A-continued

| Example No. | FGFR-3 $IC_{50}$ [nM] |
|---|---|
| 57 | 53.3 |
| 58 | 46.7 |
| 59 | 47.7 |
| 60 | 58.6 |
| 61 | 43.5 |
| 62 | 57.8 |
| 63 | 34.5 |
| 64 | 56.4 |
| 65 | 49.5 |
| 66 | 67.2 |
| 67 | 28.4 |
| 68 | 29.3 |
| 69 | 59.9 |
| 70 | 57.7 |
| 71 | 79.3 |
| 72 | 47.2 |
| 73 | 64.8 |
| 74 | 87.1 |
| 75 | 115.2 |
| 76 | 73.7 |
| 77 | 82.3 |
| 78 | 95.8 |
| 79 | 48.6 |
| 80 | 120.4 |
| 81 | 110.0 |
| 82 | 71.9 |
| 83 | 97.9 |
| 84 | 39.1 |
| 85 | 22.1 |
| 86 | 9.6 |
| 87 | 29.1 |
| 88 | 21.3 |
| 89 | 28.2 |
| 90 | 30.3 |
| 91 | 23.9 |
| 92 | 11.7 |
| 96 | 11.9 |
| 97 | 9.9 |
| 98 | 13.1 |
| 99 | 66.6 |
| 100 | 35.9 |
| 101 | 29.1 |
| 102 | 89.6 |
| 103 | 114.0 |
| 104 | 14.6 |
| 105 | 25.7 |
| 106 | 62.6 |
| 107 | 46.1 |
| 109 | 37.1 |
| 110 | 57.4 |
| 111 | 85.6 |
| 112 | 101.9 |
| 113 | 64.7 |
| 114 | 30.5 |
| 115 | 63.9 |
| 116 | 71.5 |
| 117 | 34.8 |
| 118 | 45.0 |
| 119 | 29.7 |
| 120 | 53.9 |
| 121 | 65.9 |
| 122 | 65.6 |
| 123 | 58.0 |

Selected 8-amino-1-(benzothiophen-2-yl)imidazo[1,5-a]pyrazine derivatives and related compounds which were regarded to be representative of closest prior art (see Int. Pat. Appl. WO 2007/061737-A2 and example compounds described therein) were synthesized following the published procedures and also tested in the FGFR-3 assay for comparative purposes. $IC_{50}$ values that were obtained for these compounds are listed in Table 2B below:

TABLE 2B
| Structure of comparative compound | Example No. in WO 2007/061737 | FGFR-3 $IC_{50}$ [nM] |
|---|---|---|
| 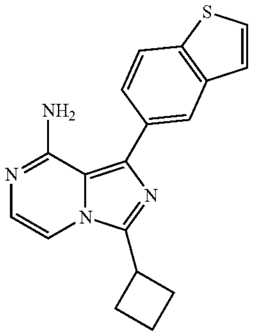 [SMILES: Nc1nccn2c(C3CCC3)nc(-c3ccc4sccc4c3)c12] | 4 | 2400 |
| 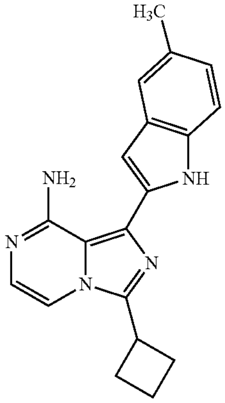 [SMILES: Cc1ccc2[nH]c(-c3nc(C4CCC4)n4ccnc(N)c34)cc2c1] | 5 | 250 |
| 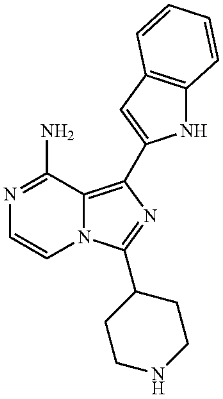 x2HCl | 25 | 1200 |
| 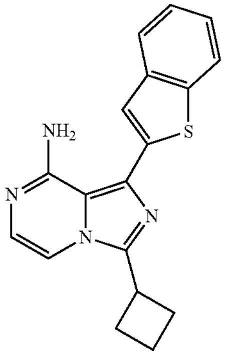 [SMILES: Nc1nccn2c(C3CCC3)nc(-c3cc4ccccc4s3)c12] | 120 | 506 |
TABLE 2B-continued
| Structure of comparative compound | Example No. in WO 2007/061737 | FGFR-3 $IC_{50}$ [nM] |
|---|---|---|
| 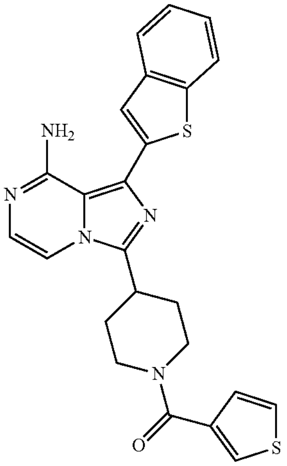 [SMILES: Nc1nccn2c(C3CCN(C(=O)c4ccsc4)CC3)nc(-c3cc4ccccc4s3)c12] | 157 | 2300 |
| 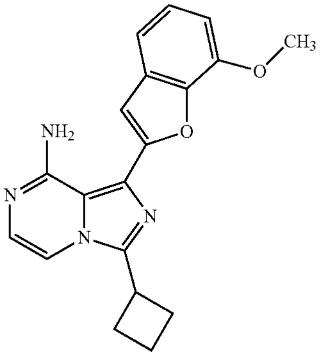 [SMILES: COc1cccc2cc(-c3nc(C4CCC4)n4ccnc(N)c34)oc12] | 205 | 20000 |
| 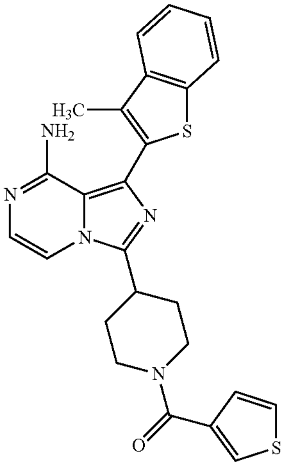 [SMILES: Cc1c(-c2nc(C3CCN(C(=O)c4ccsc4)CC3)n3ccnc(N)c23)sc2ccccc12] | 209 | 786 |

TABLE 2B-continued

| Structure of comparative compound | Example No. in WO 2007/061737 | FGFR-3 $IC_{50}$ [nM] |
|---|---|---|
| 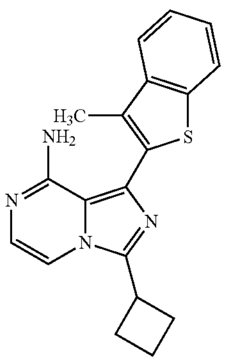 [SMILES: Cc1c(-c2nc(C3CCC3)n3ccnc(N)c23)sc2ccccc12] | 210 | 554 |
| 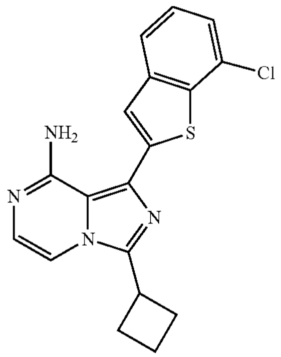 [SMILES: Nc1nccn2c(C3CCC3)nc(-c3cc4cccc(Cl)c4s3)c12] | 233 | 10000 |

The $IC_{50}$ values specified in Table 2A and 2B demonstrate that the compounds of the present invention are up to thirty times more potent in inhibiting FGFR-3 kinase activity than the selected prior art compounds.

B-3. FGFR-4 High ATP Kinase Assay

FGFR-4 inhibitory activity at high ATP concentration of the compounds of the present invention after their pre-incubation with FGFR-4 was quantified employing the TR-FRET based FGFR-4 high ATP assay as described in the following paragraphs:

A recombinant tagged FGFR-4 fusion protein [fusion of glutathione-S-transferase (GST) (N-terminally), His6-tag, thrombin cleavage site, and the intracellular part of human FGFR-4 from amino acids R391 to T802 as in GenBank entry NM_002011], expressed in SF9 insect cells using baculovirus expression system and purified via glutathione-agarose affinity chromatography, was purchased from Proqinase (product no. 0127-0000-3) and used as enzyme. As substrate for the kinase reaction, the biotinylated peptide biotin-Ahx-AAEEEYFFLFAKKK (C-terminus in amide form) was used which can be purchased, e.g., from Biosyntan (Berlin-Buch, Germany).

Usually, test compounds were tested on the same microtiter plate at 11 different concentrations in the range of 20 μM to 0.1 nM (e.g. 20 μM, 5.9 μM, 1.7 μM, 0.51 μM, 0.15 μM, 44 nM, 13 nM, 3.8 nM, 1.1 nM, 0.33 nM, and 0.1 nM) in duplicates for each concentration. The dilution series was prepared separately prior to the assay as 100-fold concentrated stock solutions in DMSO; exact concentrations could vary depending on the pipettor used. For the assay, 50 nl of each stock solution of the test compound in DMSO was pipetted into a black, low-volume 384-well microtiter plate (Greiner Bio-One, Frickenhausen, Germany). 2 μl of a solution of the above FGFR-4 fusion protein in aqueous assay buffer [8 mM MOPS pH 7.0, 10 mM magnesium acetate, 1.0 mM dithiothreitol, 0.05% (w/v) bovine serum albumin (BSA), 0.07% (v/v) Tween-20, 0.2 mM EDTA] was added, and the mixture was incubated for 15 min at 22° C. to allow pre-binding of the test compound to the enzyme. Then, the kinase reaction was started by the addition of 3 μl of a solution of adenosine triphosphate (ATP, 3.3 mM; final concentration in the 5 μl assay volume=2 mM) and substrate (0.8 μM; final concentration in the 5 μl assay volume=0.5 μM) in assay buffer, and the resulting mixture was incubated for a reaction time of 60 min at 22° C. The concentration of FGFR-4 fusion protein was adjusted depending on the activity of the enzyme lot and was chosen appropriately to have the assay in the linear range (typical concentrations were in the range of 0.03 μg/ml). The reaction was stopped by the addition of 5 μl of a solution of HTRF detection reagents [100 nM streptavidin-XL665 (Cis Biointernational) and 1 nM PT66-Tb-cryptate, a terbium-cryptate labelled anti-phosphotyrosine antibody (Cis Biointernational; PT66-Eu-chelate from Perkin-Elmer may be used instead), in an aqueous EDTA solution (50 mM EDTA, 0.1% (w/v) BSA in 50 mM HEPES/NaOH pH 7.5)].

The resulting mixture was incubated for 1 h at 22° C. to allow formation of the complex between the phosphorylated biotinylated peptide and the detection reagents. Subsequently, the amount of phosphorylated substrate was evaluated by measurement of the resonance energy transfer from the Tb-chelate to the streptavidin-XL665. For this, the fluorescence emissions at 620 nm and 665 nm after excitation at 350 nm were measured in a TR-FRET reader [e.g. Rubystar (BMG Labtechnologies, Offenburg, Germany) or Viewlux (Perkin-Elmer)]. The ratio of the emissions at 665 nm and at 620 nm was taken as the measure for the amount of phosphorylated substrate. Data were normalised (enzyme reaction without inhibitor=0% inhibition, all other assay components but no enzyme=100% inhibition), and $IC_{50}$ values were calculated by a 4-parameter fit using an in-house software.

B-4. mTOR Kinase Assay (for Comparative Purposes)

mTOR inhibitory activity of the compounds of the present invention was quantified employing the TR-FRET based mTOR assay as described in the following paragraphs:

Recombinant fusion tagged mTOR protein [glutathione-S-transferase (GST) fused to human mTOR amino acids from 1360 to 2549], expressed in insect cells and purified by glutathione-sepharose affinity chromatography, was purchased from Invitrogen (Cat.-No. 4753) and used as enzyme. As substrate for the kinase reaction, a recombinant fusion protein of GFP and 4E-BP1 (purchased from Invitrogen, Cat.-No. PV4759) was used.

Test compounds were dissolved in DMSO to generate 10 mM stock solutions. These solutions were first 10-fold diluted by 100% DMSO to get 1 mM solutions in 100% DMSO, then 100-fold diluted by 50% DMSO to get 10 μM solutions in 50% DMSO.

For the assay, 0.5 μl of a 10 μM solution of the test compound in 50% DMSO was pipetted into a black, low-volume 384-well microtiter plate (Greiner Bio-One, Frickenhausen, Germany). 2 μl of a solution of the above mTOR fusion protein in aqueous assay buffer [50 mM HEPES/NaOH pH 7.5, 5 mM magnesium chloride, 1.0 mM dithiothreitol, 1 mM EGTA, 0.01% (v/v) Triton-X100, 0.01% (w/v) bovine serum albumin (BSA)] was added, and the mixture was incubated for 15 min at 22° C. to allow pre-binding of the test compound to the enzyme. Then, the kinase reaction was started by the addition of 2.5 μl of a solution of adenosine triphosphate (ATP, 80 μM; final concentration in the 5 μl assay volume=40 μM) and substrate (0.6 μM; final concentration in the 5 μl assay volume=0.3 μM) in assay buffer, and the resulting mixture was incubated for a reaction time of 60 min at 22° C. The concentration of mTOR fusion protein was chosen appropriately to have the assay in the linear range (a typical final concentration in the 5 μl assay volume was 1.25 ng/μl). The reaction was stopped by the addition of 5 μl of 30 mM EDTA (final concentration in the 10 μl assay volume=15 mM) and 2 nM Tb-chelate labelled anti-4E-BP1 [pT46] phosphospecific antibody [Invitrogen Cat.-No. PV4755] (final concentration in the 10 μl assay volume=1 nM) in FRET buffer.

The resulting mixture was incubated for 1 h at 22° C. to allow formation of the complex between the phosphorylated substrate and the Tb-chelate labelled antibody. Subsequently, the amount of phosphorylated substrate was evaluated by measurement of the resonance energy transfer from the Tb-chelate to the GFP. For this, the fluorescence emissions at 495 nm and 520 nm after excitation at 340 nm was measured in an Envision 2104 multilabel reader (Perkin-Elmer). The ratio of the emissions at 520 nm and at 495 nm was taken as the measure for the amount of phosphorylated substrate. Data were normalised (enzyme reaction without inhibitor=0% inhibition, all other assay components but no enzyme=100% inhibition), and either mean values (if tested in replicates at a single concentration) or $IC_{50}$ values (by a 4-parameter fit using an in-house software) were calculated.

Mean inhibition values at 1 μM for individual compounds of the present invention are listed in Table 3 below:

TABLE 3

| Example No. | mTOR % inhibition @ 1 μM |
|---|---|
| 1 | 17.6 |
| 2 | 22.8 |
| 3 | 12.2 |
| 4 | 26.2 |
| 5 | 18.8 |
| 6 | 33.5 |
| 7 | 43.7 |
| 8 | 45.9 |
| 9 | 24.2 |
| 10 | 28.1 |
| 11 | 27.8 |
| 12 | 11.4 |
| 13 | 25.2 |
| 14 | 30.6 |
| 15 | 25.2 |
| 16 | 26.7 |
| 17 | 34.3 |
| 18 | 39.1 |
| 19 | 25.9 |
| 20 | 35.6 |
| 21 | 37.6 |
| 22 | 14.0 |
| 23 | 28.1 |
| 24 | 17.3 |
| 25 | 10.2 |
| 26 | no inhib. effect detect. |
| 27 | 2.4 |
| 28 | 6.9 |
| 29 | 2.4 |
| 30 | 16.2 |
| 31 | 19.5 |
| 32 | 41.3 |
| 33 | 21.5 |
| 34 | 4.9 |
| 35 | 34.0 |
| 36 | 18.3 |
| 37 | 13.4 |
| 38 | 11.2 |
| 39 | 21.4 |
| 40 | 15.0 |
| 41 | 25.9 |
| 42 | 36.3 |
| 43 | 13.8 |
| 44 | 10.8 |
| 45 | 25.9 |
| 46 | 26.3 |
| 47 | 29.0 |
| 48 | 16.9 |
| 49 | 1.3 |
| 50 | 3.4 |
| 51 | 0.9 |
| 52 | 7.3 |
| 53 | 12.6 |
| 54 | 45.9 |
| 55 | 24.6 |
| 56 | 32.1 |
| 57 | 16.2 |
| 58 | 12.6 |
| 59 | 7.0 |
| 60 | 11.3 |
| 61 | 8.6 |
| 62 | 25.1 |
| 63 | 26.0 |
| 64 | 28.2 |
| 65 | 5.9 |
| 66 | 5.9 |
| 67 | 48.0 |
| 68 | 43.1 |
| 69 | 4.6 |
| 70 | 27.9 |
| 71 | 21.5 |
| 72 | no inhib. effect detect. |
| 73 | 17.2 |
| 74 | 46.9 |
| 75 | 18.6 |
| 76 | 29.9 |
| 77 | 20.2 |
| 78 | 35.6 |
| 79 | 16.7 |
| 80 | 3.0 |
| 81 | 44.7 |
| 82 | 18.7 |
| 83 | 18.3 |
| 84 | 15.3 |
| 85 | 28.2 |
| 86 | 33.0 |
| 87 | 21.9 |
| 88 | 29.5 |
| 89 | 28.7 |
| 90 | 22.7 |
| 91 | 17.7 |
| 92 | 19.9 |
| 93 | 47.2 |
| 94 | 44.7 |
| 95 | 40.3 |
| 96 | 37.9 |
| 97 | 16.7 |
| 98 | 24.6 |
| 99 | 9.9 |
| 100 | 15.9 |
| 101 | 24.9 |
| 102 | 12.8 |
| 103 | 9.2 |
| 104 | 17.9 |
| 105 | 17.1 |
| 106 | 5.6 |
| 107 | 15.0 |
| 108 | 7.1 |
| 109 | no inhib. effect detect. |
| 110 | 4.9 |
| 111 | 1.1 |
| 112 | 8.8 |
| 113 | 29.7 |
| 114 | 27.7 |
| 115 | 6.5 |

TABLE 3-continued

TABLE 3-continued

| Example No. | mTOR % inhibition @ 1 μM |
|---|---|
| 116 | 28.0 |
| 117 | 0.3 |
| 118 | 18.4 |
| 119 | 25.1 |
| 120 | 14.8 |
| 121 | 26.8 |
| 122 | 35.7 |
| 123 | 47.8 |

(no inhib. effect detect. = no inhibitory effect detectable at 1 μM).

The data in Table 3 show that the compounds of the present invention only have a weak inhibitory effect on mTOR kinase which is not considered to significantly contribute to the pharmacological activity observed with these compounds.

B-5. Inhibition of Growth Factor-Mediated Cell Proliferation

Human umbilical vein endothelial cells (HUVEC) were obtained from Cellsystems (FC-0003) and grown in Vasculife VEGF complete medium (Cellsystems, LL-1020) containing 2% fetal bovine serum (FBS) at 37° C. and 5% $CO_2$. The cells were used for proliferation assays up to passage 7.

The HUVEC cells were harvested using accutase (PAA, L11-007) and seeded in columns 2 to 12 of 96-well plates (Falcon MICROTEST tissue culture plate 96-well flat bottom, BD 353075, or μCLEAR-PLATE, black, 96-well, Greiner Bio-One, No. 655090) at a cell density of 2500 cells/well in 100 μl Vasculife VEGF complete medium with column 1 remaining empty as blank. Cells were allowed to incubate at 37° C. and 5% $CO_2$ for at least 6 h. Then, the cells were washed once with PBS and starved overnight in Vasculife basal medium (Cellsystems, LM-0002) containing heparin, ascorbate and L-glutamine (components of the Vasculife Life Factors Kit, Cellsystems, LL-1020) as well as 0.2% FBS.

After about 18 h, the starving medium was discarded, and the cells were exposed for 72 h to 9 consecutive log or half-log concentrations of test compound in the range of 10 pM to 30 μM and to 5, 10 or 20 ng/ml hFGF-2 (recombinant human FGF basic, R&D Systems, 233-FB) in 100 μl starving medium. 10 mM stock solutions of test compounds in DMSO were diluted to 200× final concentration in DMSO resulting in a final DMSO concentration of 0.5% in all wells. Controls consisted of cells grown in starving medium only and of cells grown in hFGF-2 containing starving medium with 0.5% DMSO. To determine cell proliferation, 5 μl Alamar Blue solution (Biosource, DAL1100) was added to each well (1:20 dilution), and the cells were allowed to incubate for further 4 h at 37° C. and 5% $CO_2$ before measuring fluorescence (ex. 535 nm, em. 595 nm) with a Spectrafluor Plus Tecan plate reader (XFLUOR4 version 4.20). In some experiments, an ATP Determination Kit (BIAFFIN GmbH, LBR-T100) was used according to the manufacturer's instructions. In each experiment, samples were assayed in triplicate, and the standard deviations were determined GraphPad Prism 5 software was used to analyze the data and to obtain $IC_{50}$ values. All test compounds were assayed 2 to 10 times in independent experiments and similar results were obtained.

The data listed in Table 4 below represent the $IC_{50}$ values for representative compounds of the invention resulting from the corresponding averaged $pIC_{50}$ values:

TABLE 4

| Example No. | hFGF-2 mediated HUVEC proliferation, $IC_{50}$ [nM] |
|---|---|
| 1 | 36 |
| 2 | 127 |
| 5 | 48 |
| 6 | 22 |
| 7 | 44 |
| 8 | 370 |
| 9 | 145 |
| 10 | 21 |
| 14 | 32 |
| 15 | 180 |
| 16 | 80 |
| 17 | 150 |
| 18 | 155 |
| 19 | 277 |
| 20 | 110 |
| 22 | 105 |
| 41 | 49 |
| 42 | 130 |
| 45 | 217 |
| 54 | 230 |
| 56 | 169 |
| 86 | 37 |
| 96 | 72 |
| 98 | 48 |
| 99 | 270 |
| 105 | 137 |
| 106 | 20 |

Most compounds of the present invention displayed about five- to fifty-fold reduced inhibitory activity in this proliferation assay when vascular endothelial growth factor (VEGF-$A_{165}$ isoform) was used as mediating growth factor (instead of FGF-2), indicating a significant selectivity of these compounds for FGFR versus VEGFR kinases.

B-6. Human Xenograft and Syngeneic Tumor Models

Different tumor models have been conducted in order to profile compounds of the present invention in vivo. Human, rat or mouse tumor cells were cultivated in vitro and implanted into either immunodeficient or immunocompetent mice, or immunodeficient rats. Treatment started after tumor establishment, and tumor-bearing animals were treated with substances via different routes (per os, intravenously, intraperitoneally or subcutaneously). Substances were tested as monotherapy or in combination therapy with other pharmacological substances. Treatment of the tumor-bearing animals was conducted until the tumors reached an average size of 120 $mm^2$ Tumors were measured in two dimensions using a caliper, and tumor volume was calculated according to the formula (length×width$^2$)/2. Substance efficacy was evaluated at the end of the experiment using the T/C ratio [T=final tumor weight in the treated group; C=final tumor weight in the control group]. Statistical significance of the efficacy between control and treated groups was determined using the ANOVA variance test. All animal studies were conducted according to the German regulatory guidelines.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

C. EXAMPLES RELATING TO PHARMACEUTICAL COMPOSITIONS

Pharmaceutical compositions according to the present invention can be illustrated as follows:

Sterile i.v. Solution:

A 5 mg/mL solution of the desired compound of the invention can be made using sterile, injectable water, and the pH is adjusted if necessary. The solution is diluted for administration to 1-2 mg/mL with sterile 5% dextrose and is administered as an i.v. infusion over about 60 minutes.

Lyophilized Powder for i.v Administration:

A sterile preparation can be prepared with (i) 100-1000 mg of the desired compound of the invention as a lyophilized powder, (ii) 32-327 mg/mL sodium citrate, and (iii) 300-3000 mg Dextran 40. The formulation is reconstituted with sterile, injectable saline or 5% dextrose to a concentration of 10 to 20 mg/mL, which is further diluted with saline or 5% dextrose to 0.2 to 0.4 mg/mL, and is administered either as i.v. bolus or by i.v. infusion over 15-60 minutes.

Intramuscular Suspension:

The following solution or suspension can be prepared for intramuscular injection:

50 mg/mL of the desired, water-insoluble compound of the invention; 5 mg/mL sodium carboxymethylcellulose; 4 mg/mL Tween 80; 9 mg/mL sodium chloride; 9 mg/mL benzyl alcohol.

Hard Shell Capsules:

A large number of unit capsules are prepared by filling standard two-piece hard gelatin capsules each with 100 mg of the desired, powdered compound of the invention, 150 mg of lactose, 50 mg of cellulose and 6 mg of magnesium stearate.

Soft Gelatin Capsules:

A mixture of the desired compound of the invention in a digestible oil, such as soybean oil, cottonseed oil or olive oil, is prepared and injected by means of a positive displacement pump into molten gelatin to form soft gelatin capsules containing 100 mg of the active ingredient. The capsules are washed and dried. The desired compound of the invention can be dissolved in a mixture of polyethylene glycol, glycerin and sorbitol to prepare a water-miscible medicine mix.

Tablets:

A large number of tablets are prepared by conventional procedures so that the dosage unit is 100 mg of the desired compound of the invention, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability, or delay absorption.

Solution or Suspension for Topical Application to the Eye (Eye Drops):

A sterile formulation can be prepared with 100 mg of the desired compound of the invention as a lyophilized powder reconstituted in 5 mL of sterile saline. As preservative, benzalkonium chloride, thimerosal, phenylmercuric nitrate, or the like may be used in a range of about 0.001% to 1% by weight.

We claim:

1. A compound of formula (I)

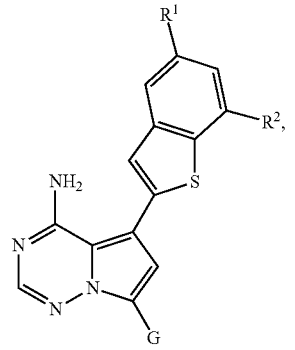

(I)

wherein $R^1$ is hydrogen, chloro, methyl or methoxy, $R^2$ is hydrogen or methoxy, with the proviso that at least one of $R^1$ and $R^2$ is other than hydrogen, and G represents the group $—CH_2—OR^3$, $—CH_2—NR^4R^5$ or $—C(=O)—NR^6R^7$, wherein $R^3$ is $(C_1-C_6)$-alkyl substituted with a residue selected from the group consisting of amino, mono-$(C_1-C_4)$-alkylamino, di-$(C_1-C_4)$-alkylamino, aminocarbonyl, mono-$(C_1-C_4)$-alkylaminocarbonyl, di-$(C_1-C_4)$-alkylaminocarbonyl and 4- to 6-membered heterocycloalkyl, or is 4- to 6-membered heterocycloalkyl, wherein said 4- to 6-membered heterocycloalkyl groups are optionally substituted with one or two residues independently selected from the group consisting of $(C_1-C_4)$-alkyl, oxo, hydroxy, amino and aminocarbonyl, $R^4$ is hydrogen or $(C_1-C_4)$-alkyl, $R^5$ is $(C_1-C_6)$-alkyl substituted with one or two residues independently selected from the group consisting of hydroxy, $(C_1-C_4)$-alkoxy, amino, mono-$(C_1-C_4)$-alkylamino, di-$(C_1-C_4)$-alkylamino, hydroxycarbonyl, aminocarbonyl, mono-$(C_1-C_4)$-alkylamino-carbonyl, di-$(C_1-C_4)$-alkylaminocarbonyl, $(C_1-C_4)$-alkylcarbonylamino, aminocarbonylamino and 4- to 6-membered heterocycloalkyl, wherein said 4- to 6-membered heterocycloalkyl is optionally substituted with one or two residues independently selected from the group consisting of $(C_1-C_4)$-alkyl, oxo, hydroxy, amino and aminocarbonyl, or is $(C_1-C_4)$-alkylcarbonyl optionally substituted with a residue selected from the group consisting of hydroxy, $(C_1-C_4)$-alkoxy, amino, mono-$(C_1-C_4)$-alkylamino and di-$(C_1-C_4)$-alkylamino, or is $(C_3-C_6)$-cycloalkyl optionally substituted with one or two residues independently selected from the group consisting of $(C_1-C_4)$-alkyl, hydroxy, $(C_1-C_4)$-alkoxy, amino, mono-$(C_1-C_4)$-alkylamino and di-$(C_1-C_4)$-alkylamino, or is 4- to 6-membered heterocycloalkyl optionally substituted with one or two residues independently selected from the group consisting of $(C_1-C_4)$-alkyl, oxo, hydroxy, amino and aminocarbonyl, or $R^4$ and $R^5$ are joined and, taken together with the nitrogen atom to which they are attached, form a mono- or bicyclic, saturated, 4- to 10-membered heterocycloalkyl ring which may contain a second ring heteroatom selected from N and O, and which may be substituted with up to three residues independently selected from the group consisting of $(C_1$-$C_4)$-alkyl, oxo, hydroxy, $(C_1$-$C_4)$-alkoxy, amino, mono-$(C_1$-$C_4)$-alkylamino, di-$(C_1$-$C_4)$-alkylamino, azetidino, pyrrolidino, piperidino, $(C_1$-$C_4)$-alkyl-carbonyl, $(C_3$-$C_6)$-cycloalkylcarbonyl, hydroxycarbonyl, am inocarbonyl, mono-$(C_1$-$C_4)$-alkylaminocarbonyl, di-$(C_1$-$C_4)$-alkylaminocarbonyl, thienyl and phenyl, wherein the alkyl groups of said $(C_1$-$C_4)$-alkyl, $(C_1$-$C_4)$-alkoxy, mono-$(C_1$-$C_4)$-alkylamino, di-$(C_1$-$C_4)$-alkylamino and $(C_1$-$C_4)$-alkyl-carbonyl residues, for their part, are optionally substituted with a residue selected from the group consisting of hydroxy, amino and am inocarbonyl, and wherein said thienyl and phenyl groups are optionally substituted with one or two residues independently selected from the group consisting of fluoro, chloro, cyano, methyl and trifluoromethyl, or $R^4$ and $R^5$ are joined and, taken together with the nitrogen atom to which they are attached, form an imidazol-1-yl or 1,2,4-triazol-1-yl ring each of which may be substituted with one or two residues independently selected from the group consisting of $(C_1$-$C_4)$-alkyl and cyano, $R^6$ is hydrogen, $R^7$ is 4- to 6-membered heterocycloalkyl optionally substituted with one or two residues independently selected from the group consisting of $(C_1$-$C_4)$-alkyl, oxo, hydroxy, amino and aminocarbonyl, or $R^6$ and $R^7$ are joined and, taken together with the nitrogen atom to which they are attached, form a monocyclic, saturated, 4- to 7-membered heterocycloalkyl ring which may contain a second ring heteroatom selected from N and O, and which may be substituted with one or two residues independently selected from the group consisting of $(C_1$-$C_4)$-alkyl, oxo, hydroxy, amino, mono-$(C_1$-$C_4)$-alkylamino, di-$(C_1$-$C_4)$-alkyl-amino and aminocarbonyl, or a pharmaceutically acceptable salt thereof.

2. The compound of formula (I) according to claim 1, wherein $R^1$ is chloro or methyl, $R^2$ is methoxy, and G represents the group —$CH_2$—$OR^3$, —$CH_2$—$NR^4R^5$ or —C(═O)—$NR^6R^7$, wherein $R^3$ is $(C_2$-$C_4)$-alkyl substituted with a residue selected from the group consisting of amino, mono-$(C_1$-$C_4)$-alkylamino and pyrrolidin-1-yl, or is pyrrolidin-3-yl, $R^4$ is hydrogen or methyl, $R^5$ is $(C_1$-$C_4)$-alkyl substituted with a residue selected from the group consisting of hydroxy, amino, mono-$(C_1$-$C_4)$-alkylamino, di-$(C_1$-$C_4)$-alkylamino, aminocarbonyl and mono-$(C_1$-$C_4)$-alkylaminocarbonyl, or is $(C_1$-$C_4)$-alkylcarbonyl optionally substituted with amino, or is $(C_3$-$C_6)$-cycloalkyl optionally substituted with a residue selected from the group consisting of hydroxy, amino, mono-$(C_1$-$C_4)$-alkyl-amino and di-$(C_1$-$C_4)$-alkylamino, or is 5- or 6-membered heterocycloalkyl optionally substituted with one or two residues independently selected from the group consisting of $(C_1$-$C_4)$-alkyl, oxo and amino, or $R^4$ and $R^5$ are joined and, taken together with the nitrogen atom to which they are attached, form a monocyclic, saturated, 4- to 7-membered heterocycloalkyl ring which may contain a second ring heteroatom selected from N and O, and which may be substituted with up to three residues independently selected from the group consisting of $(C_1$-$C_4)$-alkyl, oxo, hydroxy, amino, mono-$(C_1$-$C_4)$-alkylamino, di-$(C_1$-$C_4)$-alkyl-amino, $(C_1$-$C_4)$-alkylcarbonyl, $(C_3$-$C_6)$-cycloalkylcarbonyl, aminocarbonyl and mono-$(C_1$-$C_4)$-alkylaminocarbonyl, wherein the alkyl groups of said $(C_1$-$C_4)$-alkyl, mono-$(C_1$-$C_4)$-alkyl-amino, di-$(C_1$-$C_4)$-alkylamino and $(C_1$-$C_4)$-alkylcarbonyl residues, for their part, are optionally substituted with hydroxy, $R^6$ is hydrogen, $R^7$ is 5- or 6-membered heterocycloalkyl optionally substituted with one or two residues independently selected from the group consisting of $(C_1$-$C_4)$-alkyl, oxo and amino, or $R^6$ and $R^7$ are joined and, taken together with the nitrogen atom to which they are attached, form a monocyclic, saturated, 5- to 7-membered heterocycloalkyl ring which may contain a second ring heteroatom selected from N and O, and which may be substituted with one or two residues independently selected from the group consisting of $(C_1$-$C_4)$-alkyl, oxo, hydroxy, amino, mono-$(C_1$-$C_4)$-alkylamino, di-$(C_1$-$C_4)$-alkyl-amino and aminocarbonyl, or a pharmaceutically acceptable salt thereof.

3. The compound of formula (I) according to claim 1, wherein $R^1$ is methyl, $R^2$ is methoxy, and G represents the group —$CH_2$—$NR^4R^5$ or —C(═O)—$NR^6R^7$, wherein $R^4$ is hydrogen, $R^5$ is $(C_1$-$C_4)$-alkyl substituted with amino, methylamino or amino-carbonyl, or is $(C_1$-$C_4)$-alkylcarbonyl substituted with amino, or is 2-oxopyrrolidin-3-yl or 2-oxopiperidin-3-yl, or $R^4$ and $R^5$ are joined and, taken together with the nitrogen atom to which they are attached, form a pyrrolidin-1-yl, piperidin-1-yl or piperazin-1-yl ring each of which may be substituted with one or two residues independently selected from the group consisting of methyl, oxo, hydroxy, amino, methylamino, dimethylamino and aminocarbonyl, $R^6$ is hydrogen, $R^7$ is 2-oxopyrrolidin-3-yl or 2-oxopiperidin-3-yl, or $R^6$ and $R^7$ are joined and, taken together with the nitrogen atom to which they are attached, form a pyrrolidin-1-yl, piperidin-1-yl or piperazin-1-yl ring each of which may be substituted with one or two residues independently selected from the group consisting of methyl, oxo, hydroxy, amino, methylamino, dimethylamino and aminocarbonyl, or a pharmaceutically acceptable salt thereof.

4. A process for preparing a compound of formula (I) according to claim 1, comprising either

[A] reacting 4-aminopyrrolo[2,1-f][1,2,4]triazine of formula (II)

(II)

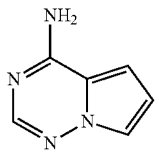

with formaldehyde and an amine of formula (III)

(III)

wherein $R^4$ and $R^5$ are defined in claim 1, in the presence of an acid to give a compound of formula (IV)

(IV)

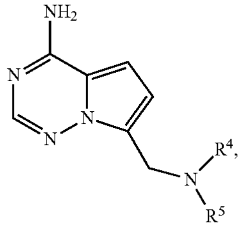

wherein $R^4$ and $R^5$ are defined in claim 1, brominating the compound of formula (IV) to a compound of formula (V)

(V)

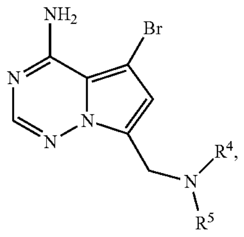

wherein $R^4$ and $R^5$ are defined in claim 1, and coupling the compound of formula (V) with a benzothiophen-2-yl boronate of formula (VI)

(VI)

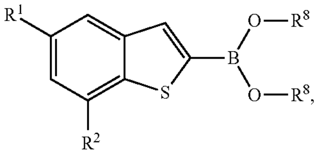

wherein $R^1$ and $R^2$ are defined in claim 1, and $R^8$ represents hydrogen or $(C_1\text{-}C_4)$-alkyl, or both $R^8$ residues are linked together to form a $-(CH_2)_2-$, $-C(CH_3)_2-C(CH_3)_2-$, $-(CH_2)_3-$, $-CH_2-C(CH_3)_2-CH_2-$or $-C(=O)-CH_2-N(CH_3)-CH_2-C(=O)-$bridge, in the presence of a palladium catalyst and a base to yield the target compound of formula (I-A)

(I-A)

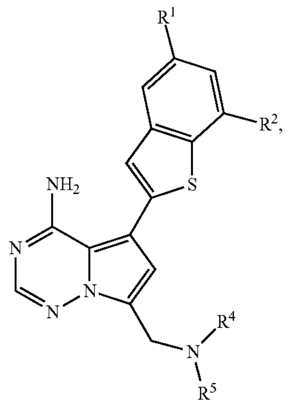

wherein $R^1$, $R^2$, $R^4$ and $R^5$ are defined in claim 1, or

[B] treating 4-aminopyrrolo[2, 1-f][1,2,4]triazine of formula (II)

(II)

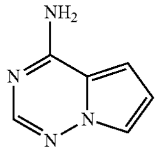

with N,N-dimethylformamide in the presence of phosphoryl chloride to give a formyl compound of formula (VII)

(VII)

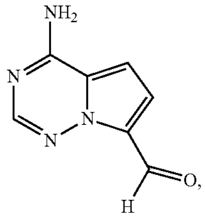

brominating the compound of formula (VII) to a compound of formula (VIII)

(VIII)

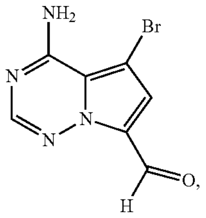

and coupling the compound of formula (VIII) with a benzothiophen-2-yl boronate of formula (VI)

(VI)

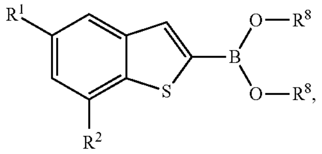

wherein $R^1$, $R^2$ and $R^8$ are defined in claim 1, in the presence of a palladium catalyst and a base to give a compound of formula (IX)

(IX)

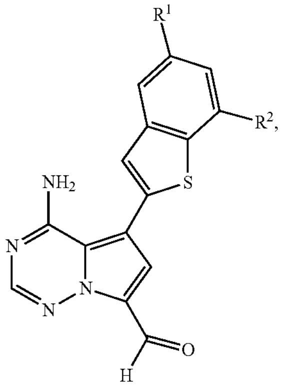

wherein $R^1$ and $R^2$ are defined in claim 1, and either

[B-1] reacting the compound of formula (IX) with an amine of formula (III)

(III)

wherein $R^4$ and $R^5$ are defined in claim 1, in the presence of an acid and a reducing agent to yield the target compound of formula (I-A)

(I-A)

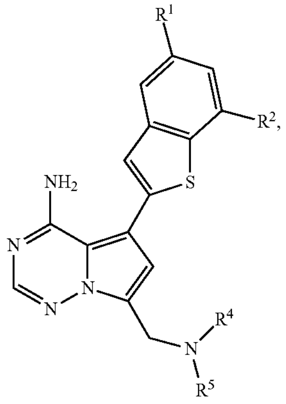

wherein $R^1$, $R^2$, $R^4$ and $R^5$ are defined in claim 1, or

[B-2] oxidizing the compound of formula (IX) to a carboxylic acid of formula (X)

(X)

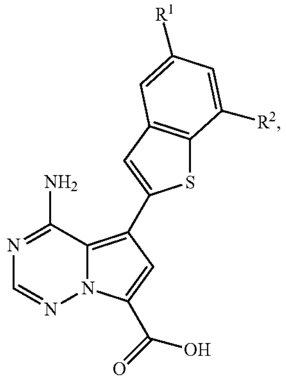

wherein $R^1$ and $R^2$ are defined in claim 1, and coupling the compound of formula (X) with an amine of formula (XI)

(XI)

wherein $R^6$ and $R^7$ are defined in claim 1, in the presence of a condensing agent to yield the target compound of formula (I-B)

(I-B)

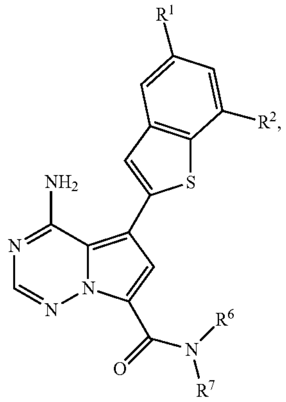

wherein $R^1$, $R^2$, $R^6$ and $R^7$ are defined in claim 1, or

[B-3] reducing the compound of formula (IX) to an alcohol of formula (XII)

(XII)

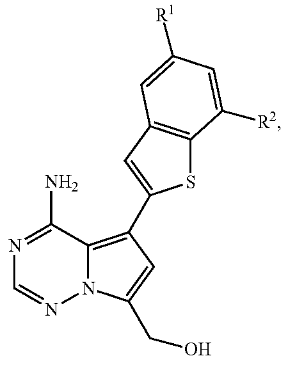

wherein $R^1$ and $R^2$ are defined in claim 1, converting the compound of formula (XII) into the corresponding halomethyl derivative of formula (XIII)

(XIII)

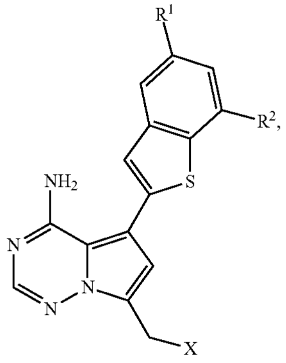

wherein $R^1$ and $R^2$ are defined in claim 1 , and

X is chloro, bromo or iodo, and treating the compound of formula (XIII) with an alcohol of formula (XIV)

$R^3$—OH (XIV), wherein $R^3$ is defined in claim 1, in the optional presence of a base to yield the target compound of formula (I-C)

(I-C)

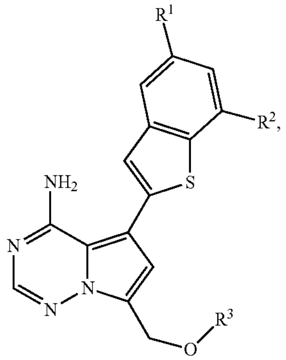

wherein $R^1$, $R^2$ and $R^3$ are defined in claim 1, optionally followed by (i) separating the compound of formula (I) into its enantiomers and/or diastereomers, or (ii) converting the compound of formula (I) into a salt thereof by treatment with a solvent and/or acid or base.

5. A pharmaceutical composition comprising a compound as defined in claim 1 and one or more pharmaceutically acceptable excipients.

6. The pharmaceutical composition of claim 5 further comprising one or more additional therapeutic agents.

* * * * *